(12) United States Patent
Pfister et al.

(10) Patent No.: US 11,787,847 B2
(45) Date of Patent: Oct. 17, 2023

(54) METHOD OF IDENTIFYING MALODOR MODULATING COMPOUNDS

(71) Applicant: FIRMENICH SA, Satigny (CH)

(72) Inventors: Patrick Pfister, Plainsboro, NJ (US); Matthew Rogers, Plainsboro, NJ (US); Huey-Ling Kao, Plainsboro, NJ (US); Claude Ayome Abibi, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/492,115

(22) PCT Filed: Mar. 8, 2018

(86) PCT No.: PCT/EP2018/055753
§ 371 (c)(1),
(2) Date: Sep. 7, 2019

(87) PCT Pub. No.: WO2018/162638
PCT Pub. Date: Sep. 13, 2018

(65) Prior Publication Data
US 2020/0002399 A1 Jan. 2, 2020

Related U.S. Application Data

(60) Provisional application No. 62/469,256, filed on Mar. 9, 2017.

(51) Int. Cl.
*C07K 14/705* (2006.01)
*G01N 33/50* (2006.01)

(52) U.S. Cl.
CPC ....... *C07K 14/705* (2013.01); *G01N 33/5008* (2013.01); *G01N 2500/20* (2013.01)

(58) Field of Classification Search
CPC ............. C07K 14/705; G01N 33/5008; G01N 2500/20
See application file for complete search history.

(56) References Cited

U.S. PATENT DOCUMENTS

| | | | |
|---|---|---|---|
| 10,172,894 B2 | 1/2019 | Ungerechts et al. | |
| 2005/0043513 A1* | 2/2005 | Firestein ............ | C12N 15/1089 530/350 |
| 2017/0128505 A1 | 5/2017 | Ungerechts et al. | |
| 2018/0186968 A1* | 7/2018 | Yoshikawa ............ | C08K 5/101 |
| 2019/0099461 A1 | 4/2019 | Ungerechts et al. | |

FOREIGN PATENT DOCUMENTS

| | | |
|---|---|---|
| JP | 2017042091 A | 3/2017 |
| WO | 2014210585 A2 | 12/2014 |
| WO | 2016201152 A1 | 12/2016 |
| WO | 2016201153 A1 | 12/2016 |
| WO | 2016204211 A1 | 12/2016 |

OTHER PUBLICATIONS

International Search Report and Written Opinion received in International Patent Application No. PCT/EP2018/055753, dated Sep. 13, 2018, 20 pages.
Adipietro et al., "Functional Evolution of Mammalian Odorant Receptors", PLoS Genetics, 2012, vol. 8, No. 7, 14 pages.
Araneda et al., "A pharmacological profile of the aldehyde receptor repertoire in rat olfactory epithelium", Journal of Physiology, 2004, vol. 555, No. 3, pp. 743-756.
Armelin-Correa et al., "Combining In Vivo and In Vitro Approaches To Identify Human Odorant Receptors Responsive to Food Odorants", Journal of Agricultural and Food Chemistry, 2017, Abstract Only, vol. 66, No. 10, 3 pages.
Kyte et al., "A Simple Method for Displaying the Hydropathic Character of a Protein", Journal of Molecular Biology, 1982, vol. 157, pp. 105-132.
Malnic et al., "Combinatorial Receptor Codes for Odors", Cell, 1999, vol. 96, pp. 713-723.
Malnic et al., "The human olfactory receptor gene family", PNAS, 2004, vol. 101, No. 8, pp. 2584-2589.
Marko et al., "A robust method for the amplification of RNA in the sense orientation", BMC Genomics, 2005, vol. 6, No. 27, 13 pages.
Metzker, "Sequencing technologies—the next generation", Nature Reviews Genetics, 2010, vol. 11, pp. 31-46.
Sato-Akuhara et al., "Ligand Specificity and Evolution of Mammalian Musk Odor Receptors: Effect of Single Receptor Deletion on Odor Detection", Journal of Neuroscience, 2016, vol. 36, No. 16, pp. 4482-4491.
Shepard, "A Cleavable N-Terminal Signal Peptide Promotes Widespread Olfactory Receptor Surface Expression in HEK293T Cells", PLoS One, 2013, vol. 8, No. 7, 14 pages.
Young et al., "Different evolutionary processes shaped the mouse and human olfactory receptor gene families", Human Molecular Genetics, 2002, vol. 11, No. 5, pp. 535-546.
Young et al., "Odorant receptor expressed sequence tags demonstrate olfactory expression of over 400 genes, extensive alternate splicing and unequal expression levels", Genome Biology, 2003, vol. 4, No. 11, 15 pages.

(Continued)

*Primary Examiner* — Olga N Chernyshev

(57) ABSTRACT

Provided herein are polypeptides that bind to the malodour-causing substance DMTS. Also provided are nucleic acid sequences that encode for the polypeptides. Further provided herein is a method for identifying a compound that binds, suppresses, blocks, inhibits, and/or modulates the activity of one or more olfactory receptor that is activated by the malodor-causing substance DMTS comprising a) contacting the receptor, or a chimera or fragment thereof with a compound and b) determining whether the compound has an effect on the activity of the receptor. Further provided is an expression vector comprising the nucleic acid encoding the polypeptides described as well as a non-human organism or a host cell modified to express a receptor that is activated by DMTS. Also provided is the use of the polypeptides for identifying malodor modulating compounds.

5 Claims, 5 Drawing Sheets

Specification includes a Sequence Listing.

(56) References Cited

OTHER PUBLICATIONS

Zhang et al., "The olfactory receptor gene superfamily of the mouse", Nature Neuroscience, 2002, vol. 5, No. 2, pp. 124-133.
Zhuang et al., "Synergism of Accessory Factors in Functional Expression of Mammalian Odorant Receptors", Journal of Biological Chemistry, 2007, vol. 282, No. 20, pp. 15284-15293.
UniProtKB Sequence: Q8VGA2, for "olfactory receptor", retrieved from "https://www.uniprot.org/uniprot/Q8VGA2", 2002, 6 pages.
UniProtKB Sequence: Q8N146, for "olfactory receptor 8H3", retrieved from "https://www.uniprot.org/uniprot/Q8N146", 2003, 10 pages.
NCBI Reference Sequence: NP_001011517, for "olfactory receptor 1193 [Mus musculus]", retrieved from "https://www.ncbi.nlm.nih.gov/protein/NP_001011517.2/", 2012, 2 pages.
NCBI Reference Sequence: XP_006997005, for "olfactory receptor 4S2 [Peromyscus maniculatus bairdii]", retrieved from "https://www.ncbi.nlm.nih.gov/protein/XP_006997005.1/", 2016, 2 pages.

\* cited by examiner

METHOD OF IDENTIFYING MALODOR MODULATING COMPOUNDS

CROSS-REFERENCE TO RELATED APPLICATIONS

This application is a U.S. National Phase Application of PCT/EP2018/055753, filed on Mar. 8, 2018, which claims the benefit of priority to U.S. Provisional Application No. 62/469,256, filed Mar. 9, 2017, the entire contents of which are hereby incorporated by reference herein.

FIELD

The technical field is directed to odorant and aroma receptors and assays that can be used to identify odorant and/or aroma compounds more specifically inhibitors, modulators or counteractants of malodor compounds such as dimethyl trisulfide (DMTS).

BACKGROUND

Olfaction is one of the most complex and poorly understood of human sensory systems. From olfactory receptor (OR) activation to perception, there are many steps that still require further investigation. If we can understand how the OR code for individual odorants and mixtures translates into perception then we can exploit this knowledge to bring significant benefit in several areas. These areas include odor modulators like malodor counteractants that block the perception of unpleasant odors, new flavor and fragrance ingredients that replace non-biodegradable or toxic compounds, and odor enhancers that would limit our reliance on difficult to source compounds from natural sources. The 'olfactory code' combinatorial paradigm is centered on the observation that any single OR may be activated by multiple odorants, and conversely most odorants are capable of activating several ORs. In the mouse genome there are ~1,200 distinct intact ORs. Humans, by contrast, have ~400. In both cases, the repertoire of ORs is activated by many thousands of odorants in the world, and it is this combinatorial complexity that allows for the breadth of olfactory sensations we can perceive. However, odorants or ligands for only 82 mouse (~8%) and 17 human ORs (~10%) have been identified as of 2014 using traditional deorphanization methods. In addition, the physiological relevance of most ligands for the human ORs, essentially identified in vitro, has not been tested.

A method that can rapidly and reliably identify a relatively small subset of ORs, within the entire repertoire of ORs that exist in an organism that are specifically activated or inhibited by one or more odorants is described in WO2014/210585. However, using this method, there remains a need to identify odorant receptors and more particularly malodor receptors that are activated by particular malodor-causing substances.

Malodor-causing compounds such as dimethyl trisulfide (DMTS) and other closely related polysulfide compounds such as dimethyl disulfide (DMDS) can generate unpleasant odors that arise, for example, from latrines and other "bathroom" sources that contain fecal matter or from bad breath. Hence, malodor modulators or counteractants that bind, suppress, block, inhibit, and/or modulate the activity of one or more olfactory receptor that is activated by a particular malodor-causing substance such as DMTS or DMDS are desirable. Assays that rely on such new malodor receptors or on malodor receptors newly identified as associated with particular malodors-causing substances to identify new compounds or compounds mixtures that bind to these receptors are further desired.

SUMMARY

Provided herein is a non-human host organism or a host cell that has been modified to express a receptor that is activated by DMTS wherein the receptor is selected from the group consisting of Olfr1193, Olfr1093, Olfr1097, Olfr166, Olfr169, Olfr738, Olfr742, Olfr207, Olfr665, Olfr669, Olfr1211, OR52N5, OR2L13, OR2AJ1, OR4C15, OR5AC2, OR8H3, OR11G2, OR52N2, and OR5T1.

Further provided is a non-human host organism or a host cell transformed to express a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40.

Further provided herein is an expression vector comprising a nucleic acid that encodes a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40.

Also provided herein is an expression vector having a nucleic acid wherein the nucleic acid comprises a nucleotide sequence having at least 70%, 75%, 80%, 85%, 90%, 95%, 96%, 97%, 98%, 99%, or 100% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 39, SEQ ID NO: 31, SEQ ID NO: 33, SEQ ID NO: 35, SEQ ID NO: 37, SEQ ID NO: 39, or the reverse complement thereof.

Provided herein is a nucleic acid comprising a nucleic acid sequence as recited above, and also provided is a polypeptide comprising an amino acid sequence as recited above.

Further provided herein is a method for identifying a compound that binds, suppresses, blocks, inhibits, and/or modulates the activity of at least one olfactory receptor that is activated by a malodor-causing substance such as dimethyl trisulfide (DMTS) or dimethyl disulfide (DMDS), wherein the receptor is a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40, wherein the method comprises:

a) contacting the receptor, or a chimera or fragment thereof with a compound;

b) determining whether the compound has an effect on the activity of the receptor.

Also provided is a method for identifying a compound that binds, suppresses, blocks, inhibits, and/or modulates the activity of at least one olfactory receptor that is activated by a malodor-causing substance comprising:

a. contacting a test substance and a malodor-causing substance to at least one olfactory receptor selected from the group consisting of Olfr1193, Olfr1093, Olfr1097, Olfr166, Olfr169, Olfr738, Olfr742, Olfr207, Olfr665, Olfr669, Olfr1211, OR52N5, OR2L13, OR2AJ1, OR4C15, OR5AC2, OR8H3, OR11G2, OR52N2, and OR5T1;

b. measuring the response of the olfactory receptor to the malodor-causing substance by measuring the response of the olfactory receptor in the presence and absence of the test substance;

c. identifying a test substance that modulates the response of the olfactory receptor on the basis of the response that was measured in the presence and absence of the test substance; and d. selecting the identified test substance as a compound that modulates the response of the olfactory receptor to the malodor-causing substance, wherein the malodor-causing substance is dimethyl trisulfide (DMTS) or dimethyl disulfide (DMDS).

Further provided is a method for identifying a malodor modulator comprising:

a. contacting a test substance and a malodor-causing substance to at least one olfactory receptor, wherein the receptor comprises a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40;

b. measuring the response of the olfactory receptor polypeptide to the malodor-causing substance;

c. identifying, based on the measured response, a test substance that can suppress the response of the olfactory receptor; and d. selecting, as a malodor modulator, the test substance that that binds, suppresses, blocks, inhibits, and/or modulates the response of the olfactory receptor, wherein the malodor-causing substance is dimethyl trisulfide (DMTS) or dimethyl disulfide (DMDS).

Additionally provided is a recombinant nucleic acid molecule comprising: a nucleic acid comprising at least one of a Lucy tag, a FLAG® tag, and/or a Rho tag and a nucleic acid encoding a receptor selected from the group consisting of Olfr1193, Olfr1093, Olfr1097, Olfr166, Olfr169, Olfr738, Olfr742, Olfr207, Olfr665, Olfr669, Olfr1211, OR4S2, OR52N5, OR2L13, OR2AJ1, OR4C15, OR5AC2, OR8H3, OR11G2, OR52N2, and OR5T1 or the reverse complement thereof.

Still yet further provided is a non-human host organism or a host cell that is recombinantly modified to express a nucleic acid or a polypeptide as described above.

DETAILED DESCRIPTION OF THE DRAWINGS

DETAILED DESCRIPTION

Figure 1:
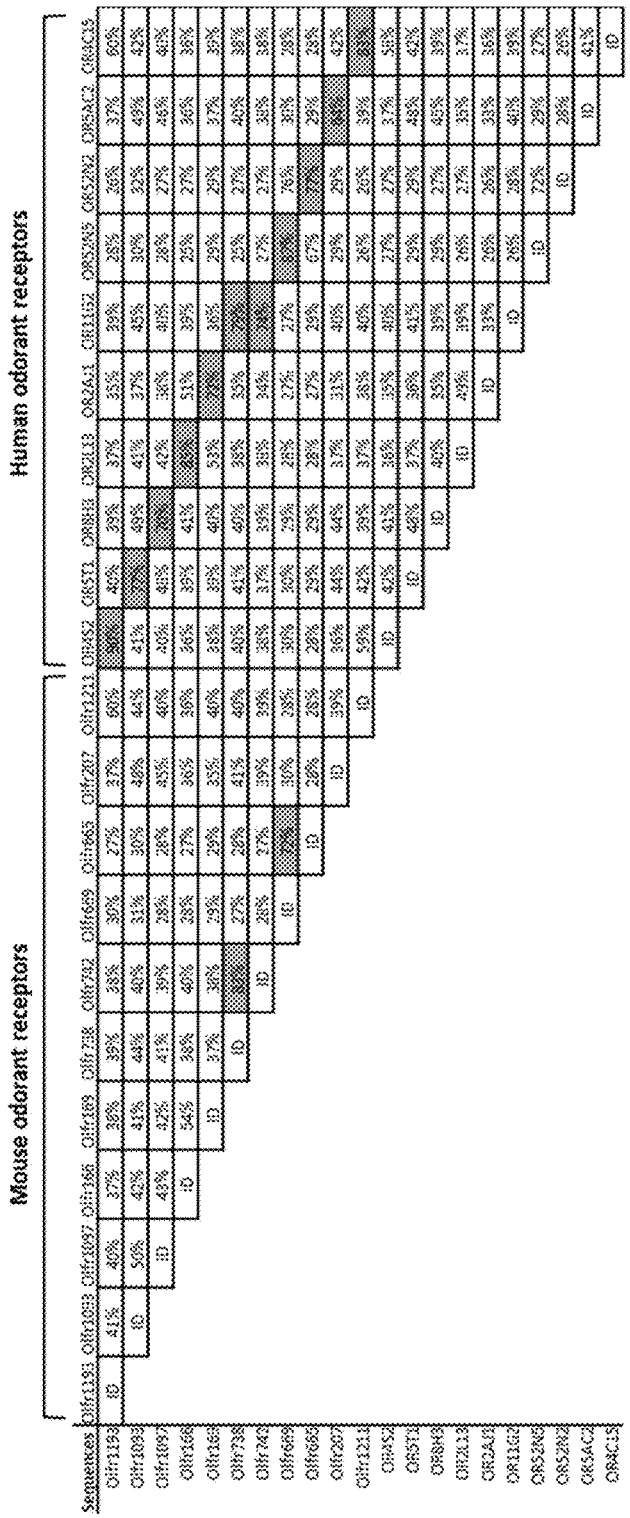
FIG. 1 shows the pairwise amino acid identity levels between the receptors mentioned herein.

For the descriptions herein and the appended claims, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The following terms have the meanings ascribed to them unless specified otherwise.

"OR" refers to one or more members of a family of G protein-coupled receptors (GPCRs) that are expressed in olfactory cells. Olfactory receptor cells can also be identified on the basis of morphology or by the expression of proteins specifically expressed in olfactory cells. OR family members may have the ability to act as receptors for olfactory signal transduction.

"DMTS OR" or "DMDS OR" refers to a member of the family of G protein-coupled receptors that is expressed in an olfactory cell, which receptors bind and/or are activated by DMTS or DMDS in a binding or activity assay for identifying ligands that bind and/or activate GPCRs. Such assays are described below. DMTS or DMDS receptors herein will include fragments, variants, including synthetic and naturally occurring, and chimeras or recombinant nucleic acids or proteins that respond to or bind DMTS or DMDS.

"OR" polypeptides are considered as such if they pertain to the 7-transmembrane-domain G protein-coupled receptor superfamily encoded by a single ~1 kb long exon and exhibit characteristic olfactory receptor-specific amino acid motifs. The seven domains are called "transmembrane" or "TM" domains TM I to TM VII connected by three "internal cellular loop" or "IC" domains IC I to IC III, and three "external cellular loop" or "EC" domains EC I to EC III. The motifs and the variants thereof are defined as, but not restricted to, the MAYDRYVAIC motif (SEQ ID NO: 53) overlapping TM III and IC II, the FSTCSSH motif (SEQ ID NO: 54) overlapping IC III and TM VI, the PMLNPFIY motif (SEQ ID NO: 55) in TM VII as well as three conserved C residues in EC II, and the presence of highly conserved GN residues in TM I [Zhang, X. & Firestein, S. Nat. Neurosci. 5, 124-133 (2002); Malnic, B., et al. Proc. Natl. Acad. Sci. U.S.A. 101, 2584-2589 (2004)].

"OR" nucleic acids encode a family of GPCRs with seven transmembrane regions that have "G protein-coupled receptor activity," e.g., they may bind to G proteins in response to extracellular stimuli and promote production of second messengers such as IP3, cAMP, cGMP, and $Ca^{2+}$ via stimulation of enzymes such as phospholipase C and adenylate cyclase.

"Paralogous" OR genes or "paralogs" are the result of gene duplications and refer to closely related homologous genes within the same species. "Orthologous" OR genes or "orthologs" are defined as phylogenetically linked by a gene present in a common ancestor and refer to closely related homologous genes in other species.

The "N terminal domain" region starts at the N-terminus and extends to a region close to the start of the first transmembrane region. "Transmembrane regions" comprise the seven "transmembrane domains," which refers to the domain of OR polypeptides that lies within the plasma membrane, and may also include the corresponding cytoplasmic (intracellular) and extracellular loops. The seven transmembrane regions and extracellular and cytoplasmic loops can be identified using standard methods such as hydrophobicity profiles, or as described in Kyte & Doolittle, J. Mol. Biol., 157:105-32 (1982), or in Stryer. The general secondary and tertiary structure of transmembrane domains, in particular the seven transmembrane domains of G protein-coupled receptors such as olfactory receptors, are known in the art. Thus, primary structure sequence can be predicted based on known transmembrane domain sequences, as described in detail below. These transmembrane domains are useful for in vitro ligand-binding assays.

The phrase "functional effects" in the context of assays for testing compounds that modulate OR family member mediated olfactory transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction receptor-ligand interactions, second messenger concentrations (e.g., cAMP, cGMP IP3, or intracellular $Ca.^{2+}$), in vitro, in vivo, and ex vivo and also includes other physiologic effects such as increases or decreases of neurotransmitter or hormone release.

By "determining the functional effect" or "confirming the activity" in the context of assays is meant assays for a compound that increases or decreases a parameter that is indirectly or directly under the influence of an OR family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte OR gene expression; tissue culture cell OR expression; transcriptional activation of OR genes or activity induced genes such as egr-1 or c-fos; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Binder," "suppressors," "blockers," "inhibitors," "activators," and/or "modulators" of OR genes or proteins are used interchangeably to refer to binding, suppressing, blocking, suppressing, inhibitory, activating, or modulating molecules identified using in vivo, in vitro and ex vivo assays for olfactory transduction, e.g., ligands, agonists, antagonists, enhancers, and their homologs and mimetics. Inhibitors are compounds that, e.g., bind to, partially or totally block stimulation, decrease, suppress, prevent, delay activation, inactivate, desensitize, or down regulate olfactory transduction, e.g., antagonists. Activators are compounds that, e.g., bind to, stimulate, increase, open activate, facilitate, enhance activation, sensitize, or up regulate olfactory transduction, e.g., agonists. Modulators include compounds that, e.g., alter the interaction of a receptor with: extracellular proteins that bind activators or inhibitor (e.g., odorant-binding proteins, ebnerin and other members of the hydrophobic carrier family, or a member of the lipocalin family); G proteins; kinases (e.g., homologs of rhodopsin kinase and beta adrenergic receptor kinases that are involved in deactivation and desensitization of a receptor); and arrestins, which also deactivate and desensitize receptors. Modulators also include compounds that alter the affinity or the transduction efficacy of an OR altering the effect of an activator on the OR. Modulators can include genetically modified versions of OR family members, e.g., with altered activity, as well as naturally occurring and synthetic ligands, antagonists, agonists, small chemical molecules and the like. Such assays for inhibitors and activators include, e.g., expressing OR family members in cells or cell membranes, applying putative modulator compounds, in the presence or absence of flavor, fragrance or malodour molecules, e.g. a malodour-causing substance such as DMTS, and then determining the functional effects on olfactory transduction, as described above. Samples or assays comprising OR family members that are treated with a potential activator, inhibitor, or modulator are compared to control samples without the inhibitor, activator, or modulator to examine the extent of modulation. Control samples (untreated with modulators) are assigned a relative OR activity value of 100%. Inhibition of an OR is achieved when the OR activity value relative to the control is about 80%, optionally 50% or 25-0%.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated" "isolated," when referring to a nucleic acid or protein, of nucleic acids or proteins, also refers to a state of purification or concentration different than that which occurs naturally in the mammalian, especially human body. Any degree of purification or concentration greater than that which occurs naturally in the mammalian, especially human body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

The term "7-transmembrane receptor" means a polypeptide belonging to a superfamily of transmembrane proteins that have seven domains that span the plasma membrane seven times (thus, the seven domains are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues.

In addition to the gene sequences shown in the sequences disclosed herein, it will be apparent for the person skilled in the art that variants also include DNA sequence polymorphisms that may exist within a given population, which may lead to changes in the amino acid sequence of the polypeptides disclosed herein. Such genetic polymorphisms may exist in cells from different populations or within a population due to natural allelic variation. Allelic variants may also include functional equivalents.

Further embodiments also relate to the molecules derived by such sequence polymorphisms from the concretely disclosed nucleic acids. These natural variations usually bring about a variance of about 1 to 5% in the nucleotide sequence of a gene or in the amino acid sequence of the polypeptides disclosed herein. As mentioned above, the nucleic acid encoding the polypeptide of an embodiment herein is a useful tool to modify non-human host organisms or host cells intended to be used in the methods described herein.

The terms "polypeptide," "peptide" and "protein" are used interchangeably herein to refer to a polymer of amino acid residues, whether comprising naturally occurring amino acids or polymers and non-naturally occurring amino acids or polymers. The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" means also the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence potentially amplified using a primer. "Recombinant" means also modifications obtained by genome editing techniques, such as CRISPR/Cas9, of a cell that leads to stable or transient expression of endogenous genes such as the receptor gene referred to herein.

The term "expression vector" refers to any recombinant expression system for the purpose of expressing a nucleic acid sequence of the invention in vitro, ex vivo, or in vivo, constitutively or inducibly, in any cell, including prokaryotic, yeast, fungal, plant, insect or mammalian cell. The term includes any linear or circular expression systems including but not limited to viral vectors, bacteriophages and plasmids. The skilled person is capable of selecting a suitable vector according to the expression system. The term includes expression systems that remain episomal or integrate into the host cell genome. The expression systems can have the ability to self-replicate or not, i.e., drive transient expression in a cell. The term includes recombinant "expression cassettes" which can contain the minimum elements needed for transcription of the recombinant nucleic acid. The term also covers cassettes or vectors for expression of endogenous genes through, for example, genome editing methods such as CRISPR/Cas9.

By "a non-human organism or a host cell" is meant a non-human organism or a cell that contains a nucleic acid as described herein or an expression vector and supports the replication or expression of the expression vector. Host cells may be prokaryotic cells such as $E.\ coli$, or eukaryotic cells such as yeast, insect, amphibian, or mammalian cells such as CHO, HeLa, HEK-293, and the like, e.g., cultured cells, explants, and cells in vivo.

By "tag" or "tag combination" is meant a short polypeptide sequence that can be added to the odorant receptor protein. Typically, the DNA encoding a "tag" or a "tag combination" is added to the DNA encoding the receptor, eventually resulting in a fusion protein where the "tag" or a "tag combination" is fused to the N-terminus or C-terminus of the receptor. Lucy, FLAG® and/or Rho tags can enhance the receptor trafficking to the cell membrane, hence the can assist in expression of a functional odorant receptor for in vitro cell based assay [Shepard, B. et al. PLoS One 8, e68758-e68758 (2013), and Zhuang, H. & Matsunami, H. J. Biol. Chem. 282, 15284-15293 (2007)].

In one embodiment provided herein is an isolated nucleic acid molecule comprising a nucleic acid sequence having at least 70%, 75%, 80%, 85%, 90%, 95%, 96%, 97%, 98%, 99%, or 100% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 39, SEQ ID NO: 31, SEQ ID NO: 33, SEQ ID NO: 35, SEQ ID NO: 37, SEQ ID NO: 39 or the reverse complement thereof.

In one embodiment provided herein is an isolated nucleic acid sequence as described above which encodes a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40.

In a further embodiment provided herein is an isolated polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40.

In one embodiment, a non-human organism or a host cell is transformed to express a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40.

In one embodiment, a non-human organism or a host cell is transformed to express a polypeptide comprising an amino acid sequence that is identical to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40.

Further provided herein is an expression vector comprising a nucleic acid that encodes a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40.

Also provided herein is an expression vector comprising a nucleic acid that comprises a nucleic acid sequence having at least 70%, 75%, 80%, 85%, 90%, 95%, 96%, 97%, 98%, 99%, or 100% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 39, SEQ ID NO: 31, SEQ ID NO: 33, SEQ ID NO: 35, SEQ ID NO: 37, SEQ ID NO: 39 or the reverse complement thereof.

Also provided herein is an expression vector having a nucleic acid wherein the nucleic acid comprises a nucleotide sequence that is identical to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 39, SEQ ID NO: 31, SEQ ID NO: 33, SEQ ID NO: 35, SEQ ID NO: 37, SEQ ID NO: 39 or the reverse complement thereof.

In one embodiment herein is a method for identifying a compound that binds, suppresses, blocks, inhibits, and/or modulates the activity of an olfactory receptor that is activated by a malodor-causing substance such as dimethyl trisulfide (DMTS) or dimethyl disulfide (DMDS), wherein the receptor is a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40, wherein the method comprises:

a) contacting the receptor, or a chimera or fragment thereof with a compound;
   b) determining whether the compound has an effect on the activity of the receptor.

In one embodiment is a method for identifying a compound that binds, suppresses, blocks, inhibits, and/or modulates the activity of an olfactory receptor that is activated by a malodor-causing substance comprising:

a. contacting a test substance and a malodor-causing substance to at least one olfactory receptor selected from the group consisting of Olfr1193, Olfr1093, Olfr1097, Olfr166, Olfr169, Olfr738, Olfr742, Olfr207, Olfr665, Olfr669, Olfr1211, OR52N5, OR2L13, OR2AJ1, OR4C15, OR5AC2, OR8H3, OR11G2, OR52N2, and OR5T1;
   b. measuring the response of the olfactory receptor to the malodor-causing substance by measuring the response of the olfactory receptor in the presence and absence of the test substance;
   c. identifying a test substance that modulates the response of the olfactory receptor on the basis of the response that was measured in the presence and absence of the test substance; and
   d. selecting the identified test substance as a compound that modulates the response of the olfactory receptor to the malodor-causing substance, wherein the malodor-causing substance is dimethyl trisulfide (DMTS) or dimethyl disulfide (DMDS).

In a further embodiment herein is a method for identifying a malodor modulator comprising:

a. contacting a test substance and a malodor-causing substance to at least one olfactory receptor, wherein the receptor comprises a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40;
b. measuring the response of the olfactory receptor polypeptide to the malodor-causing substance;
c. identifying, based on the measured response, a test substance that can modulate or suppress the response of the olfactory receptor; and
d. selecting, as a malodor modulator, the test substance that that binds, suppresses, blocks, inhibits, and/or modulates the response of the olfactory receptor;

wherein the malodor-causing substance is dimethyl trisulfide (DMTS) or dimethyl disulfide (DMDS).

One embodiment is a method for identifying a malodor inhibitor comprising:
a. contacting a test substance and a malodor-causing substance to at least one olfactory receptor, wherein the receptor comprises a polypeptide comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40;
b. measuring the response of the olfactory receptor polypeptide to the malodor-causing substance;
c. identifying, based on the measured response, a test substance that can suppress the response of the olfactory receptor; and
d. selecting, as a malodor inhibitor, the test substance that suppresses the response of the olfactory receptor, wherein the malodor-causing substance is DMTS and the malodor is a fecal malodor or oral malodor.

One embodiment is a method of identifying a compound that putatively modulates DMTS associated malodor comprising: (i) contacting a cell line that expresses a DMTS receptor polypeptide comprising an amino acid sequence having at least 90% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40 with at least one compound; (ii) screening for compounds that bind, suppress, block, inhibit, and/or modulate the activity of said olfactory receptor polypeptide; and (iii) identifying a compound that putatively modulates DMTS associated malodor if it binds, suppresses, blocks, inhibits, and/or modulates the activity of said DMTS receptor polypeptide.

In a further embodiment, the malodor-causing substance in the methods described herein is dimethyl trisulfide (DMTS).

Additionally provided is a a recombinant nucleic acid molecule comprising
a. a nucleic acid comprising a tag combination that comprises one or more of a Lucy, FLAG®, and/or Rho tag; and
b. a nucleic acid encoding a receptor selected from the group consisting of Olfr1193, Olfr1093, Olfr1097, Olfr166, Olfr169, Olfr738, Olfr742, Olfr207, Olfr665, Olfr669, Olfr1211, OR4S2, OR52N5, OR2L13, OR2AJ1, OR4C15, OR5AC2, OR8H3, OR11G2, OR52N2, and OR5T1 or the complement thereof.

In a further embodiment the Lucy tag comprises SEQ ID NO: 47, the FLAG® tag comprises SEQ ID NO: 43, and the Rho tag comprises SEQ ID NO: 45.

Further provided is any one of a number of malodor modulating compounds that binds, suppresses, blocks, inhibits, and/or modulates the activity of an olfactory receptor that is activated by a malodor-causing substance such as dimethyl trisulfide (DMTS) and that is identified by the methods disclosed herein.

In one embodiment herein is a malodor modulating compound that binds, suppresses, blocks, inhibits, and/or modulates the activity of at least one olfactory receptor selected from the group consisting of Olfr1193, Olfr1093, Olfr1097, Olfr166, Olfr169, Olfr738, Olfr742, Olfr207, Olfr665, Olfr669, Olfr1211, OR52N5, OR2L13, OR2AJ1, OR4C15, OR5AC2, OR8H3, OR11G2, OR52N2, and OR5T1, and that is identified by the methods disclosed herein.

Another embodiment relates to the use of a polypeptide that is or can be activated by DMTS or DMDS comprising an amino acid sequence having at least 70%, 75%, 80%, 85%, 90%, 95%, 96%, 97%, 98%, 99%, or 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40 for identifying a malodor modulating compound that binds, suppresses, blocks, inhibits, and/or modulates the activity of an olfactory receptor.

Still yet further provided is a cell that is recombinantly modified to express a polypeptide described above.

In one embodiment herein is a non-human host organism or a host cell that has been transformed or modified to express a receptor that is activated by DMTS selected from the group consisting of Olfr1193, Olfr1093, Olfr1097, Olfr166, Olfr169, Olfr738, Olfr742, Olfr207, Olfr665, Olfr669, Olfr1211, OR4S2, OR52N5, OR2L13, OR2AJ1 OR4C15, OR5AC2, OR8H3, OR11G2, OR52N2, and OR5T1.

In one embodiment herein is is a non-human host organism or a host cell that has been transformed or modified to express a receptor that is activated by DMTS, wherein the receptor comprises a polypeptide as described herein or a polypeptide encoded by a nucleic acid described herein.

In a further embodiment herein is a non-human host organism or a host cell that comprises a nucleic acid or expression vector as described herein.

In one embodiment provided herein is a cell wherein the cell is a prokaryotic cell. In another embodiment the cell provided herein is a eukaryotic cell. In a particular embodiment, the cell provided herein is selected from a group consisting of a yeast cell and a plant cell. In a more particular embodiment provided herein the cell is selected from the group consisting of HEK293, CHO, *Xenopus oocytes*, COS, yeast, bacteria and cells derived from the olfactory placode.

In order to identify unknown DMTS or DMDS specific receptors, DMTS and DMDS can be used to screen dissociated olfactory sensory neurons (OSNs). DMTS and DMDS can be further used for cell-based dose-response experiments performed on specific DMTS or DMDS receptors to assess both specificity and sensitivity of the receptors.

In one aspect, provided herein are methods to identify mammalian odorant receptors for malodour modulating compounds and the use of the receptors for screening, particularly for high throughput screening (HTS) of malodor modulators (e.g. that bind, suppress, block, inhibit and/or modulate the activity of an OR).

In particular provided herein are mouse receptors, for example, Olfr1193, Olfr1093, Olfr1097, Olfr166, Olfr169, Olfr738, Olfr742, Olfr669, Olfr665, Olfr207, Olfr1211, and their human counterparts OR4S2, OR5T1, OR8H3, OR2L13, OR2AJ1, OR11G2, OR52N5, OR52N2, OR5AC2, and OR4C15, as receptors for the malodour-causing substances DMTS, DMDS or other polysulfide compounds, as shown in Table 1.

TABLE 1

Orthologous mouse and human odorant receptor pairs and their corresponding identity at the amino acid level.

| Mouse ortholog | Human ortholog | Amino acid identity |
| --- | --- | --- |
| Olfr1193 | OR4S2 | 90% |
| Olfr1093 | OR5T1 | 77% |
| Olfr1097 | OR8H3 | 70% |
| Olfr166 | OR2L13 | 85% |
| Olfr169 | OR2AJ1 | 72% |
| Olfr738 | OR11G2 | 79% |
| Olfr742 | OR11G2 | 74% |
| Olfr669 | OR52N5 | 87% |
| Olfr665 | OR52N2 | 77% |
| Olfr207 | OR5AC2 | 64% |
| Olfr1211 | OR4C15 | 83% |

While not wishing to be bound to any theory, mouse receptor Olfr738 is a paralog of receptor Olfr742 and human OR11G2 is the ortholog of these mouse receptors; and mouse receptor Olfr669 is a paralog of receptor Olfr665 and an ortholog of human receptor OR52N5; and mouse receptor Olfr665 is an ortholog of human receptor OR52N2. Several receptors were previously identified as indole and/or skatole responsive odorant receptors in WO2014/210585. However, these receptors had not been previously associated with the malodour-causing substances DMTS or DMDS or other related polysulfide compounds. Indole and skatole are not chemically related to polysufide compounds and therefore approaches based on chemical structure such as structure-activity-relationship (SAR) to identify additional ligands would not define DMTS as a potential agonist of these receptors.

In a further embodiment, indicators for monitoring the activity of olfactory receptors are selected from a fluorescent calcium indicator dye, a calcium indicator protein, a fluorescent cAMP indicator, a cell mobilization assay, a cellular dynamic mass redistribution assay, a label-free cell based assay, a cAMP response element (CRE) mediated reporter protein, a biochemical cAMP HTRF assay, a beta-arrestin assay, or an electrophysiological recording. Particularly, a calcium indicator dye is selected that can be used to monitor the activity of olfactory receptors expressed on the membrane of the olfactory neurons (e.g., Fura-2 AM).

In a particular embodiment, compounds are screened sequentially and the odorant-dependent changes in calcium dye fluorescence are measured using a fluorescent microscope or fluorescent-activated cell sorter (FACS).

In a further embodiment, molecular 3D receptor modeling of olfactory receptors is used to assess the binding potential in silico and to identify compounds that may activate, mimic, block, inhibit, modulate, and/or enhance the activity of an olfactory receptor.

As an example, olfactory neurons activated by DMTS or DMDS are isolated using either a glass microelectrode attached to a micromanipulator or a FACS machine. Mouse olfactory sensory neurons are screened by $Ca^{2+}$ imaging similar to procedures previously described [Malnic, B., et al. Cell 96, 713-723 (1999); Araneda, R. C. et al. J. Physiol. 555, 743-756 (2004); and WO2014/210585 hereby incorporated by reference in its entirety]. Particularly, a motorized movable microscope stage is used to increase the number of cells that can be screened to at least 1,500 per experiment. Since there are approximately 1,200 different olfactory receptors in the mouse and each olfactory sensory neurons expresses only 1 of 1,200 olfactory receptor genes, this screening capacity will cover virtually the entire mouse odorant receptor repertoire. In other words, the combination of calcium imaging for high-throughput olfactory sensory neuron screening leads to the identification of nearly all of the odorant receptors that respond to a particular profile of odorants. In a particular aspect, odorant receptors that respond to DMTS or DMDS can be isolated. For example, at least one neuron is isolated.

For calcium imaging of olfactory neurons, the main olfactory epithelium may be dissected from a mouse before neuronal dissociation. Dissected olfactory epithelium may then be transferred to a dissociation buffer for mechanical and enzymatic dissociation. Dissociated neurons may then be seeded onto a coverslip allowing the screening of thousands of cells by fluorescence microscopy and the cells may be loaded with a calcium sensitive dye (Fura-2 AM) for example for about 30 minutes at 31° C. and transferred onto the microscope ready for screening. Cells are stimulated by perfusing diluted solutions of odorants (in physiological saline) over the dissociated olfactory neurons. The rare cells that respond to the malodor compound are identified by for example stimulating the receptors with 50 μm of the malodor compounds and then by monitoring the intracellular $Ca^{2+}$ flux indicated by changes in Fura-2 fluorescence. After analysis, responding cells may be retrieved from a glass coverslip with a suction micropipette. Isolated cells are then pooled into one sample or treated individually for subsequent identification of the odorant receptor genes expressed as mRNA in the responding cells.

In a particular embodiment, the mRNAs of olfactory neurons are purified and amplified according to the method generally described in Marko, N. F., et al., (2005) A robust method for the amplification of RNA in the sense orientation. *BMC genomics*, 6, 27; doi:10.1186/1471-2164-6-27 (Eberwine method). At least a portion of the transcriptome (up to including the entire transcriptome) is sequenced using Next-Generation Sequencing (NGS) technologies or hybridized to known genes using Microarray technologies. NGS is generally discussed and described in Metzker, M. L. Nat. Rev. Genet. 11, 31-46 (2010). In a particular embodiment, a minimum of 5 neurons presenting the same response profile are pooled. The mRNAs are released by cell lysis immediately after picking; no DNAse and no purification steps are carried out. The mRNA are amplified by two consecutive rounds of in vitro transcription (IVT). The amplification may be done according to MesageAmpII aRNA kit (Ambion, AMA1751) with the following parameters: two rounds of consecutive 14 hour long IVT.

In a further embodiment, the mRNA of a single olfactory neuron is purified and amplified with LD-PCR (Long Distance Polymerase Chain Reaction) based methods such as the one described in NGS-ready kits (e.g., Clontech/Takara, SMARTer® Ultra® Low Input RNA Kit for Sequencing—v3, cat. 634848). Single cell mRNA is first reverse transcribed into the corresponding cDNA, which subsequently is amplified with 18 PCR cycles and serves as NGS sample for transcriptome sequencing.

In yet another embodiment, the identity of a group or gene family of DMTS olfactory receptors is determined (e.g., up to as many as the number of neurons picked) by comparing the results of the NGS reads obtained from the isolated activated olfactory sensory neurons to a reference genome sequence of the same species. Particularly, the putative DMTS receptors will be the most highly abundant olfactory receptor mRNA in the olfactory neuron-derived NGS sample or present in more than one independent biological replicate. Because of the combinatorial nature of the olfactory code (one compound activates many ORs and one OR can be activated by many compounds), pooling several neurons activated by given compounds allows the retrieval of virtually all of the receptors responsible for the perception of these molecules in a single NGS experiment. Pooling functionally similar neurons thus greatly improves the deorphanization throughput and speed.

Standard bioinformatics tools are then used to identify the most closely related human odorant receptor(s) to other putative mammalian (non-human) DMTS receptor(s) under the assumption that homologous sequence receptors retain similar function. Several methods successfully identify human OR-ligand pairs based on this assumption [Armelin-Correa and Malnic (2017)] and up to 80% of mouse-human orthologs appear to maintain similar functional response profiles [Adipietro, K. A, et al. PLoS Genet. 8, e1002821-e1002821 (2012)]. Default parameters of BLASTP and/or BLASTN algorithm, or other ortholog pair identification algorithms such as InParanoid may be used.

The human or non-human mammalian DMTS receptors may be adapted to a functional assay that can be used to identify compounds that bind, suppress, block, inhibit, and/or modulate the activity of the olfactory receptors. In particular, the assay may be a cell-based assay or a binding assay and the method for identifying compounds may be a high-throughput screening assay. More particularly, provided herein are receptor-based assays adaptable for high-throughput screening of receptors with compound libraries for the discovery of modulating compounds (e.g., binding, blocking, inhibiting, suppressing and masking).

In a particular embodiment, DMTS receptor gene sequences are identified from DMTS-sensitive cells as follows: Pooled neurons are heated to 75° C. for 10 minutes to break the cell membrane and render their mRNA available for amplification. This amplification step is important when applying NGS technologies with limited amount of starting material, typically between 1 to 15 cells. A linear amplification according to the Eberwine method (IVT) ensures the maintenance of the relative transcription levels of expressed genes. Two consecutive overnight (14 h) rounds of in vitro transcription are used to yield sufficient amounts of cRNA; Amplified cRNA is then used to generate an Illumina HiSeq cDNA library. The resulting short sequences of typically 75 to 150 base pairs (commonly referred to as "reads") are aligned against the reference genome of the mouse (such as UCSC version mm9 or mm10) in order to build the full transcriptome of these cells. Quantitative analysis of the transcriptome data yields a list of transcribed odorant receptor genes and their respective expression levels. Odorant receptor genes that show the most abundant levels of mRNA (most abundant "reads") or are present in more than one replicate experiment are considered putative DMTS receptors.

The predicted mouse OR genes are then used to mine the latest versions of both the mouse and human genome databases in order to identify the most closely related receptors (i.e. highest sequence similarity) in mouse (paralogous genes) and in human (orthologous genes). This process may be performed using the BLAST search algorithm (publically available at the NCBI website), a sequence similarity search tool, where every putative gene sequence previously obtained from the initial transcriptome analysis is used as a query sequence. The newly identified genes identified from this data mining process are considered to be potential DMTS receptors under the assumption that paralogous and orthologous genes are highly likely to possess similar activities. In a particular embodiment, pairwise comparison of sequence homology is carried out to identify closely related receptors in mouse and humans and the receptors are identified as described in WO2014/210585. Other approaches may also be used such as RT-PCR and microarray approaches.

In a further embodiment, to complete the deorphanization process, the candidate OR genes are further expressed in vitro for confirmation of activity against the compounds used to isolate the olfactory sensory neurons and other structurally-related compounds of interest. The mouse receptors identified from isolated olfactory neurons that respond to DMTS are modified at their N-terminus with short polypeptide sequences (e.g., FLAG® (SEQ ID NO: 44), Rho (SEQ ID NO: 46; 20 first amino acids of the bovine rhodopsin receptor), and/or Lucy (SEQ ID NO: 48; cleavable leucine-rich signal peptide sequence) tags), transiently expressed in HEK 293T cells, and stimulated separately with DMTS to confirm their identity as bona fide DMTS receptors. In a further embodiment, an RTP1 gene can also be expressed in the cell lines whether through activation of the endogenous RTP1 gene or through transformation. Co-expression of the human G alpha subunit $G\alpha_{olf}$ in this cell-based assay activates the Gs transduction pathway that leads to an internal cAMP increase upon binding to the appropriate ligand. Alternatively, co-expression of the human G alpha subunit $G\alpha_{15}$ in the cell based assay activates the Gq transduction pathway that leads to an internal $Ca^{2+}$ increase upon binding to the appropriate ligand. The above process and the results obtained so far serve to validate the process for rapid and reliable identification of mammalian odorant receptors for DMTS or DMDS.

Further provided are assays for identifying compounds that bind to DMTS or DMDS odorant receptors. In a further embodiment provided herein is a malodor modulating compound that binds, suppresses, blocks, inhibits, and/or modulates the activity of at least one olfactory receptor selected from the group consisting of Olfr1193, Olfr1093, Olfr1097, Olfr166, OR52N5, OR2L13, OR4C15, OR5AC2, OR8H3, OR11G2, and OR52N2, and that is identified by the methods described herein, for example, the compounds described in FIG. 4.

In one embodiment the activity of the compound is determined by comparing its binding to that of DMTS or DMDS. In another embodiment, the receptor or a chimera or fragment thereof is contacted with a compound in the presence of DMTS or DMDS under conditions that allow for the binding of the compound along with DMTS or DMDS to the receptor.

In a further embodiment, a compound is contacted to a receptor, or a chimera or fragment thereof that is activated by DMTS or DMDS, wherein the receptor, or a chimera or fragment thereof is expressed in a cell that is recombinantly modified to express the receptor polypeptide.

The activity of the compound can be determined using in vivo, ex vivo, in vitro and synthetic screening systems.

In another embodiment, the contacting is performed with liposomes or virus-induced budding membranes containing the polypeptides described herein.

In another embodiment, the methods for identifying compounds that bind, suppress, block, inhibit, and/or modulate the activity of an olfactory receptor that can be activated by DMTS or DMDS, may be performed on intact cells or a membrane fraction from cells expressing the polypeptides described here or on olfactory sensory neurons in culture modified to express endogenous or exogenous odorant receptors.

The 21 ORs described herein are therefore involved in the perception of malodor elicited by DMTS or DMDS and constitute valuable candidate receptors for the identification of modulators, antagonists and/or blockers that would modulate, reduce, suppress, inhibit and/or block the perception of malodor.

Nucleic acid and amino acid sequences identified and/or used herein are listed below:

```
Olfr1193
DNA -
                                                     SEQ ID NO: 1
atggcctcaaggacttattccatggaagaagtaaataatgtcactgaattcattttcttgggtct ttctcagaaccctgaggttgaaaaagtgtgctttgtggtgttctccttcttttacatggtcattc tgctaggaaacctcctcatcatgttgacagtttgcagtggcaatcttttcaagtttcccatgtat ttttcctcaactttctgtcttttgtggacatttgctactcctcagtcacagcacccaagatgat tattgacctgttagtgaagaaaaagactatatcctatgtgggtgcatgttacaactctttgtgg ttcatttctttggttgcactgagatcttcattcttactgtcatggcctatgatagatatgtggcc atttgtaaacctctccactatatgactatgatggaccgggaaagatgcaataagatgttgctcgg aacatggatcggtggcttcttacattctattatccaagtggctcttgtggtccagctccccttt gtggaccgaatgagattgatcactatttctgtgatgtacatcctgtactgaaacttgcctgcact gacacttacattgttggtattttgtgacagcaaacagtggcaccattgcattgggaagttttgt catcttgctgatctcatacacagtcattctcatgtctctgagaaagcagtcatctgaaggcagac gcaaagctctctccacttgtggatcccacattgctgttgtcatcattttttttggcccctgtact tttatgtatatgcggcctgacactaccttctctgaggacaagatggtagctatattttacaccat tatcactcccatgctgaatcctctaatttacactctaagaaatgcagaagtaaagaatgcaatga gaaaactgtgggctagaaagttttcctgggaaactactgggaaatag Protein -
                                                     SEQ ID NO: 2
MASRTYSMEEVNNVTEFIFLGLSQNPEVEKVCFVVFSFFYMVILLGNLLIMLTVCSGNLFKFPMY

FFLNFLSFVDICYSSVTAPKMIDLLVKKKTISYVGCIVLQLFVVHFFGCTEIFILTVMAYDRYVA

ICKPLHYMTMVDRERCNKIVLLGTWGGFLHSIIQVALVVQLPFCGPNEIDHYFCDVHPVLKLACT

DTYIVGIFVTANSGTIALGSFVILLISYTVILMSLRKQSSEGRRKALSTCGSHIAVVIIFFGPCT

FMYMRPDTTFSEDKMVAIFYTIITPMLNPLIYTLRNAEVKNAMRKLWARKFSWETTGK

Olfr1093
DNA -
                                                     SEQ ID NO: 3
atggaaaagatcacatcagctgtggatgtccacaatattccattaaagaacatgactgaagccac catgtttattctcttaggattcacagatgactttgaactccaagtcttcctgttttactgtttc ttgctatttatctcttcactctggtaggaaactttggactggttgttttggtcattggggattgt cggctacacaaccccatgtactatttcctaagtgttttgtctttcctggatgcttgctattctac agttgttacacccaaaatgttggtcaactttctaagtgaaaataagtccatttcattccttgcat gtgcaacccaaatgcttctctttgtttcgttgggaaccacagaatgctttctcctggcagcaatg gcttatgaccgatatgtagccatctacaacccacttctgtatacagtggccatgtcacccagagt atacctgccactcatcattgcttcctatgctggtggagttgtgcatggtgctatccacacagtgg ccactttcagtctgtccttctgtggatccaatgaaattaagcatgtcttctgtgacatccctgca ttgcttgctctttcttgttctgatacccacacaaatgagcttctagtcttgtacttggtgggctt
```

-continued

```
gattgagattgttaccatcctgattgttctggtctcctatggattcatcctctttgccattctga acatgcattctgctgagggtaggaggaaagtgttctctacatgtggctctcacctcactggagtc tctatttaccatggtacaatccttttcacttatatgaggcctagttccagttatgcttcaaatca tgacatggtagtgtcaatattttacaccattgtgatacccatgttgaatcctatcatctatagtt tgaggaacaaagatgtaaaagtagcatttaataaattgtggagaaaatgtgattcataa
```

Protein -
SEQ ID NO: 4

MEKITSAVDVHNIPLKNMTEATMFILLGFTDDFELQVFLFLLFLAIYLFTLVGNFGLVVLVIGDC
RLHNPMYYFLSVLSFLDACYSTVVTPKMLVNFLSENKSISFLACATQMLLFVSLGTTECFLLAAM
AYDRYVAIYNPLLYTVAMSPRVYLPLIIASYAGGVVHGAIHTVATFSLSFCGSNEIKHVFCDIPA
LLALSCSDTHTNELLVLYLVGLIEIVTILIVLVSYGFILFAILNMHSAEGRRKVFSTCGSHLTGV
SIYHGTILFTYMRPSSSYASNHDMVSIFYTIVIPMLNPIIYSLRNKDVKVAFNKLWRKCDS

Olfr1097
DNA -
SEQ ID NO: 5

```
atgagtgcctgtaatcatacaaatgaacctgagttcacgcttgtgggactgacagactccaagga gattcagctggtcctctctgttttgtttctcctgatatacatgctcactgtcttgggaaacatag gtatgatactgatcattcatctagatgtccagctccacactccaatgtatttttttcctcacccac ttgtcattccttgacctcagttactcaactgtaatcacacctaaaaccttacagaatacgctgac ctccataaaaaatatttccttcatgggatgcttcacccagttgtatttctttgtcctcttggcag cttctgaatgttttatactttcgtcaatggcctatgaccgctatgtagctatctgcaaccctcta cactatccagttattatgtcccctaggcgctcatatactctcatcactgtgtcctacatgattgg agttttggattcttctgtcactgtcttttgcttaagcacactggattctgcaactccaaagtaa ttcatcacttcttttgtgacacattcccaattttagctctgtcctgcagtgatacctataatgca gaagccactatattcgttttagctggttccactctattgctgtcgctcatcacgatatcctcatc ctatgtatctattctctctacaattttgaagataaattcttcttcaggaaagcacaaagccttct ctacatgtgcctcacatcttataggagtcactgttttttatggtacaatgatctttacttattta aaaccaagtacgtcctactccctgggaaaggatcaagtagcctctgttttttatactatagtgat tcccatgctgaacccacttatctatagtctcaggaacaaagaagtgaaaagtgctgttgttagag ttatgaagaagagagagtgcatccagaaactagaataa
```

Protein -
SEQ ID NO: 6

MSACNHTNEPEFTLVGLTDSKEIQLVLSVLFLLIYIVLTVLGNIGMLIIHLDVQLHTPMYFFLTH
LSFLDLSYSTVITPKTLQNTLTSIKNISFMGCFTQLYFFVLLAASECFILSSMAYDRYVAICNPL
HYPVIMSPRRSYTLITVSYMIGVLDSSVTVFCLSTLDFCNSKVIHHFFCDTFPILALSCSDTYNA
EATIFVLAGSTLLLSLITISSSYVSILSTILKINSSSGKHKAFSTCASHLIGVTVFYGTMIFTYL
KPSTSYSLGKDQVASVFYTIVIPMLNPLIYSLRNKEVKSAVVRVMKKRECIQKLE

Olfr166
DNA -
SEQ ID NO: 7

```
atggagaaatggaatcagagctcaagtgatttactctgttaggactgcttccacaaaaccaaac aggcctgctacttttgatgctcatcatctttgtcttctctctggctttgtgtggcaactcaggaa tgatccacctcattcgtgtggatccaaggctccacacccccatgtactttctcctcagtcagctc tctctcatggacctgatgtacatttctaccactgttcccaagatggcatttaacttcctttctgg ccagaaaagcatctcttttctgggctgtggagtgcaatccttcttcttcctgactatggcatgtt
```

-continued

```
ctgagggcttgctcttggcttccatggcttatgatcgttttgtggctatctgccatccccttcac tatcccattcgcatgagcaaaataatgtgtctgaagatgatcataggatcctggatattgggctc aatcaactctttagcacataccgtctatgcccttcatattccttactgccattctaggtccatta accatttcttctgtgatgttccagccatgttgcccctggcctgtatggacacttgggtttatgag tacatggtgtttgtgagcacaagcctgtttctcctactgcctttccttggtatcacagcttccta tggtcgggtcctttttgctgtcttccacatgcgctcaaaagagggaaagaagaaggccttcacca catgctcaactcacttaactgtggtgacattttactatgcaccttttgtctatacctatcttcga cctaggagtcttcgctccccaacagaagataagattctggctgttttctacactatccttacccc catgctcaaccccatcatttatagtctgaggaataaggaggtcctgggggccatgacaagagtcc ttggtacttttccttcaactaaaccgtaa
```

Protein -
SEQ ID NO: 8

MEKWNQSSSDFTLLGLLPQNQTGLLLLMLIIFVFSLALCCNSGMIHLIRVDPRLHTPMYFLLSQL

SLMDLMYISTTVPKMAFNFLSGQKSISFLGCGVQSFFFLTMACSEGLLLASMAYDRFVAICHPLH

YPIRMSKIMCLKMIGSWILGSINSLAHTVYALHIPYCHSRSINHFFCDVPAIVLPLACMDTWVYE

YMVFSTSLFLLLPFLGITASYGRVLFAVFHIVRSKEGKKKAFTTCSTHLTVVTFYYAPFVYTYLR

PRSLRSPTEDKILAVFYTILTPMLNPIIYSLRNKEVLGAMTRVLGTFPSTKP

Olfr169
DNA -
SEQ ID NO: 9

```
atggaatatgagaactacacttttaacagcgacttcatcctcttgggactgttctcttcttcaaa gacaagcttaacttttttctcatttatattttttcattttattatggctataacagaaaatgccc tcatgatcctcctaatccacagggattctcgactccatacccaatgtatttcctgcttagtcat ctctccttcatggatatcttgcacattttccaacattgttcctaaaatgattgctgacttcctctc aggcagcagaactatttcctttgcaggctgtgccttccagatatttctctctcttaccttgctag gtggtgagtgccttctcctggcagccatgtcctatgatcgatatgtggccatctgccacccactt cgctaccctgtgctgatgagggataactccagtaggctcctggctgcaggctcctggctggtggg gatcctcaactccatagtacacacagttttttgcactccactttcccttctgccactcaagagcca ttgatcacttttttctgcgaagtccctgccatgttgaaattgtcatgtatagacacaacacactat gaacgaggcgtttatgtgagtggcattattttttctgctgatcccatttttccatgatctctatatc ttatgtgcaaattctcctcactgtattccaaatgcagtcatcaggggcccggcaaaagtccttttt ccacctgttccttccacatggttgttgtcataatgtactatgggccattcattttttacatatatg agacctcgctcataccacactccagggcaggataaattttttggcaatattctacaccatcctgac acccacactcaaccccataatctacagctttcgtaataaagatgtccttatggctgtgaaaaaca tcgtccaaagtaattttttgaataaaaaatga
```

Protein -
SEQ ID NO: 10

MEYENYTFNSDFILLGLFSSSKTSLTFFSFIFFIFIMAITENALMILLIHRDSRLHTPMYFLLSH

LSFMDILHISNIVPKMIADFLSGSRTISFAGCAFQIFLSLTLLGGECLLLAAMSYDRYVAICHPL

RYPVLMRDNSSRLLAAGSWLVGILNSIVHTVFALHFPFCHSRAIDHFFCEVPAMLKLSCIDTTHY

ERGVYVSGIIFLLIPFSMISISYVQILLTVFCMQSSGARQKSFSTCSFHMVVVIMYYGPFIFTYM

RPRSYHTPGQDKFLAIFYTILTPTLNPIIYSFRNKDVLMAVKNIVQSNFLNKK

Olfr738
DNA - SEQ ID NO: 11 atgaaagcctttagcagccccagcaactccagcatcatcactggcttcatcctcctgggcttccc ctgccccaaggaggggcaaatcctcctctttgtgctcttcttcattatctacatccttaccctca tgggcaatgcttccatcatatgtgctgtgtgctatgataagaaacttcacagccccatgtacctc ctgctggccaacttctccttcctagaaatctggtatgtcacctccacagtccccaacatgttggc caacttcctctctgacacgaaggtcatctcttttctctggatgcttcctgcagttctatttcttct tctccttgggttctacagaatgcttttttcctggcagtcatggcatttgatcgataccttgccatc tgcagacctctacattatccttctctcatgactgggcgcctctgcaacatccttgtgatcagttg ctgggtgcttggtttcctctggttccctgttcccatcatcatcatctcccaaatgtccttctgtg gatccagaattatagaccacttcctgtgtgacccaggccctctgttggccctcacctgtgtgaga aattctttaattgagatgactagctctactttaagttccctgcttttatttgttccattttttt tatcatgggtcttatgctctagtaatgagggctgtgctcagggtccccttcagcagctggacgaa gaaaggccttctccacctgtgggtcacacttgactgtggtttctcttttctatggctcagtgatg gtcatgtatgtgagcccaacatctgaacatgcagctggagtgcaaaaacttgtgactctgtttta ttctgtggttactcccctccttaatcctgtgatatacagtctgaggaacagagatatgaaacatg caatgaaaaagttactgaaaatgtaa Protein - SEQ ID NO: 12

MKAFSSPSNSSIITGFILLGFPCPKEGQILLFVLFFIIYILTLMGNASIICAVCYDKKLHSPMYL

LLANFSFLEIWYVTSTVPNMLANFLSDTKVISFSGCFLQFYFFFSLGSTECFFLAVMAFDRYLAI

CRPLHYPSLMTGRLCNILVISCWVLGFLWFPVPIIIISQMSFCGSRIIDHFLCDPGPLLALTCVR

NSLIEMTSSTLSSLLLFVPFFFIMGSYALVMRAVLRVPSAAGRRKAFSTCGSHLTVVSLFYGSVM

VMYVSPTSEHAAGVQKLVTLFYSVVTPLLNPVIYSLRNRDMKHAMKKLLKM

Olfr742
DNA - SEQ ID NO: 13

Atgaaaaccctcagcagccccagcaactccagcaccatcactggcttcatcctcttgggcttccc ctgccccagggaggggcaaatcctcctctttgtgaccttcttcattgtttacatactcattctta tgggcaatgcttccatcatctgtgctgtgtactgtgatcagagcctccacacccccatgtacttc ctgctggccaacttctccttcctggagatctggtatgtcacctccacagtccccaacatgttggc caacttcctttcagacaccaaggtcatctcttttctctggatgcttcctgcagttctatttcttct tctcctttggttctacagaatgcttttttcctggcagtcatggcatttgatcgataccttgccatc tgtaggccactacattatccttctctcatgactgggcacctctgcaacatccttgtgatcagttg ctgggtgcttggtttcctctggttccctgtacccatcatcatcatctcccagatgtccttctgtg ggtccagaattatagaccacttcctgtgtgacccaggccctcttttggcccttgcctgttccaga gccccattgatggaggttttctggacaattataatgtctatgctcctggttattcctttcctctt catcatgggaacttacatattggtcctaagagctgtgtttagacttccttcaagagatggacaaa aaaaggccttctccacttgcgggtctcatctcacagtagtttcactcttttattgctcagtgatg aaaatgtatttgagcccaacatctgagcatgaagctggaatgcagaagcttgtaactctattta ttctgtgggtactccactacttaatcctgtgatatacagtctgaggaacaaagatatgaaaaatg ccctgcagaagattttaagaacataa

```
Protein -
                                                    SEQ ID NO: 14
MKTLSSPSNSSTITGFILLGFPCPREGQILLFVTFFIVYILILMGNASIICAVYCDCSLHTPMYF

LLANFSFLEIWYVTSTVPNMLANFLSDTKVISFSGCFLQFYFFFSFGSTECFFLAVMAFDRYLAI

CRPLHYPSLMTGHLCNILVISCWVLGFLWFPVPIIIISQMSFCGSRIIDHFLCDPGPLLALACSR

APLMEVFWTIIMSMLLVIPFLFIMGTYILVLRAVFRLPSRCGQKKAFSTCGSHLTVVSLFYCSVM

KMYLSPTSEHEAGMQKLVTLFYSVGTPLLNPVIYSLRNKDMKNALQKILRT

Olfr207
DNA -
                                                    SEQ ID NO: 15
atggaactgaacaggacccagctgactgaatttgttctcagaggaataacagatcgttcagagct gcaagtccccctgttcctggtgttctttctcatctatgttatcaccatggtgggcaaccttggct taatctttgtcatctggaaggaccctcatcttcacacacccatgtaccttttccttggaaatttg gcctttgctgatgcctgtaattcatcctctgtgacaccaaagatgcttatgaaattttttaaataa gaatgacatgatatccatgggtgagtgttttgctcaatttatttcttttgttcaagtgtaactg cagaagccttcattctggtagctatggcctatgaccgctatgtagccatatgcaaacctctgctc tatgtagtggtgatgtccaacagactctgtattcagttcataggtgtatcctatctaattggact tctacatggcttacttcatgtaggattgttatttaggttaacgttttgtagttccaatgtaatag attatttctactgtgacatcctgccactttataggatttcttgcactgacccatcgatcaatgta ctggtagctttcattatgggtattttattacaagtgagtacctttatgagtattatagtctccta tgtccgtgtcctctttgccatcctgagaacaaagtctgagagggcagaaacaaagccttctcta cttgcagttcccacctgtcatctgtgtctttgttctatggcactctcttcatcatatatgtcctc tctggctctgacacagataattatcagggtaaaatgtattcactgttctataccattatcattcc tctgctaaacccccttcatttacagcctaagaaataaagaagtcatcggtgccttgagaaaagtca gaaaatga Protein -
                                                    SEQ ID NO: 16
MELNRTQLTEFVLRGITDRSELQVPLFLVFFLIYVITMVGNLGLIFVIWKDPHLHTPMYLFLGNL

AFADACNSSSVTPKMLMKFLNKNDMISMGECFAQFYFFCSSVTAEAFILVAMAYDRYVAICKPLL

YVVVMSNRLCIQFIGVSYLIGLLHGLLHVGLLFRLTFCSSNVIDYFYCDILPLYRISCTDPSINV

LVAFIMGILLQVSTFMSIIVSYVRVLFAILRTKSERGRNKAFSTCSSHLSSVSLFYGTLFIIYVL

SGSDTDNYQGKMYSLFYTIIIPLLNPFIYSLRNKEVIGALRKVRK

Olfr665
DNA -
                                                    SEQ ID NO: 17
atgcctggggtcaatacctccagcctgacaccaagatactttattctcaatgggattcctgggtt ggaagctgcacacatctggatctctctgccattcttcattatgtacctcattgctgtcacaggta actgtggacttatctacctcatcagtcatgaggaggctctgcaccggcccatgtactactttcta gccatgttgtctgctacagatatttctgggtgtaatacaattgtcccagtatgttatgcatctt ttggttcagtgtcaaggagattgatttcaatgcctgccttgtacagatgttttttcatccacatgt taacaggcatggagtctggtgtgctcatgcttatggctctcgaccgctatgtggctatatgctat ccattacgctatactaccatactcaccaacactatgattaccaagattggattggcagcacttgt tagaagtgtgttactcatggtcccttttgctttcctgatcaagcgtcttccatactgtagaggaa acctcatccaacatacctattgtgatcacatggctgtggctaaactatcctgtggcaatattaag attaatgctatctatggtcttataattgctatatttattgggggttttgatatattctgtatctc
```

```
catgtcttatgccatgattatccatgctgtggtgaagctatcttcggcagatgctcgccataaag ccttcagtacctgtacatcacacatatgtgctattgttattacctatgtcccagcattcttcaac ttctttactcatcgctttgggagaaccactatccccatcatatccacattattatagccaacct gtatctattgctacctcccaccttgaatccaattgtatatggagtaaagaccaagcagattcgtg aaggtgtgatcaaactgtttgctagacaaaaagttgtttga
```

Protein -

SEQ ID NO: 18

```
MPGVNTSSLTPRYFILNGIPGLEAAHIWISLPFFIMYLIAVTGNCGLIYLISHEEALHRPMYYFL

AMLSATDISGCNTIVPSMLCIFWFSVKEIDFNACLVQMFFIHMLTGVESGVLMLMALDRYVAICY

PLRYTTILTNTMITKIGLAALVRSVLLMVPFAFLIKRLPYCRGNLIQHTYCDHMAVAKLSCGNIK

INAIYGLIIAIFIGGFDIFCISMSYAMIIHAVVKLSSADARHKAFSTCTSHICAIVITYVPAFFN

FFTHRFGRTTIPHHIHIIANLYLLLPPTLNPIVYGVKTKQIREGVIKLFARQKVV
```

Olfr669
DNA -

SEQ ID NO: 19

```
atgctgatttccaacaactcatatgaagcccccgcagtcttttcattcttaatggaattcctggtct cgaagcagtgcatatatggatctctcttccactctgtacaatgtacatcatctcccctagtaggca accttggccttgtatatctcatttactatgaggaatccttacatcgcccaatgtatttcttctg gccatgcttctctcatagacctgtttacttgcacaaccactgtccccaatgccctcttcatttt ctggttcaaactcaaggaaattaacttcactgcttgcctagttcagatgttctttgtgcacggat tcacaggtgtggagtctggggtactcatgctcatggccttggaccgctatgtggccatttgctac ccactacgctatgcaaccatacttaccaaccctgtcattgccaaagctgggcttgccaccttctt gagaggtgtgttactgatgattcctttttccattcttggttaaacgtttgcccttctgccgaagca atgtcatctcccatacatattgtgaccacatgtctgtggtaaagttatcctgtgccagcatcaaa atcaatgtcatctatggtctcatggttgcacttctgattggagtgtttgacatatgttgtatatc tgtgtcctacactatgatcctccgggcagtggtcagcctgtcctctgcagatgctcggcagaagg ccttcagcacctgcacagcccacatatctgccatcatcattacttatgttccagccttcttcacc ttctttactcatcgttttggaggtcacaccatccctccttctcttcatatcattgtggctaatct ttatcttcttctccctccaactctaaatcccattgtttatgggatgaagaccaaacagatcagag atagtatcattaaattcttcacggtgaaaaaggttcaaggtga
```

Protein -

SEQ ID NO: 20

```
MLISNNSYEAPC6FILNGIPGLEAVHIWISLPLCTMYIISLVGNLGLVYLIYYEESLHRPMYFFL

AMLSLIDLFTCTTTVPNALFIFWFKLKEINFTACLVQMFFVHGFTGVESGVLMLMALDRYVAICY

PLRYATILTNPVIAKAGLATFLRGVLLMIPFPFLVKRLPFCRSNVISHTYCDHMSVVKLSCASIK

INVIYGLMVALLIGVFDICCISVSYTMILRAVVSLSSADARQKAFSTCTAHISAIIITYVPAFFT

FFTHRFGGHTIPPSLHIIVANLYLLLPPTLNPIVYGMKTKQIRDSIIKFFHGEKGSR
```

Olfr1211
DNA -

SEQ ID NO: 21

```
atgcaaaaccagagttttgtaacagaattcatattccttggacttttcacagaaccctaaagtcca gaaaatagttttttattgtattttatttgtctacattgcaactgttgggggcaacatgataattg tggtgaccattgtctgtagcccagcattgatagactgccccatgtacttcttttttggcattcttg tccctattggatgcatgcttctcttctgtcatcacaccaaagatggttgtggactccctgtatga gaagaaaactatctccttgaaggatgtatgatgcagttatttgctgagcacttccttgcagcag tagaagtgattgtcttgacagccatggcctatgaccgctatgtagcaatttgcaagcccttgcac
```

```
tactcttccatcatgaactggaggctctgtggcacacttatggggatagcatggacaggggctt cttgcattctatcatacaaattatcttcacgttgcaattgcccttctgtggaccaaatgtcatcg atcatttcatgtgtgacttgttcccattactggaacttgcctgcactgatactcatatctttggc cttttagtggttgccaacagtgggtctatctgcatcataatcttctctattttgctggtctccta tggtgtcatcctgttctctctgaaagctcacagttctgaagggcgatggaaagctctctccacat gtggatcccacattgcagttgtggttttgttctttgtcccgtgtatatttatttatgcacgtcct ccatctgctttctcctttgataaaatggtggcgatattttatactatcctaactcccttgctcaa tcctgtgatttatacttttcggaataaggacatgaaaaatgctatgaagaaagtgtggaagaggt tggcagtggtttctgatggaaagtga
```

Protein -
SEQ ID NO: 22
```
MQNQSFVTEFIFLGLSQNPKVQKIVFIVFLFVYIATVGCNMIIVVTIVCSPALIDCPMYFFLAFL

SLLDACFSSVITPKMVVDSLYEKKTISFEGCMVQLFAEHFLAAVEVIVLTAMAYDRYVAICKPLH

YSSIMNWRLCGTLMGIAWTGGFLHSIIQIIFTLQLPFCGPNVIDHFMCDLFPLLELACTDTHIFG

LLVVANSGSICIIIFSILLVSYGVILFSLKAHSSEGRWKALSTCGSHIAVVVLFFVPCIFIYARP

PSAFSFDKMVAIFYTILTPLLNPVIYTFRNKDMKNAMKKVWKRLAVVSDGK
```

OR52N5
DNA -
SEQ ID NO: 23
```
atgcctctatttaattcattatgctggtttccaacaattcatgtgactcctccatcttttattct taatggaataccthe tggtctggaaagagtacatgtatggatctccctcccactctgcacaatgtaca tcatcttccttgtggggaatcttggtcttgtgtacctcatttattatgaggagtccttacatcat ccgatgtattttttttttggccatgctctctcccctcattgacctccttacctgcaccaccactct acccaatgcactctgcatcttctggttcagtctcaaagaaattaacttcaatgcttgcttggccc agatgttctttgttcatgggttcacaggtgtggagtctggggtgctcatgctcatggctctagac cgctatgtagccatttgctacccttt
gcgttatgctaccacactcaccaaccctatcattgccaa ggctgagcttgccaccttcctgaggggtgtattgctgatgattcctttcccattcttggttaagc gtttgcctttctgccaaagcaatattatctcccatacgtactgcgaccacatgtctgtagtaaag ctatcttgtgccagcatcaaggtcaatgtaatctatggtctaatggttgctctcctgattggagt gtttgacatttgttgtatatctttgtcttacactttgatcctcaaggcagcgatcagcctctctt catcagatgctcggcagaaggctttcagcacctgcactgcccatatatctgccatcatcatcacc tatgttccagcattcttcactttcttt gcccaccgttttggggcacacacaattccccctt ctct tcacatcattgtggctaatctttatcttcttcttcccccaactctaaaccctattgtttatggag taaagacaaaacagatacgcaagagtgtcataaagttcttccagggtgataagggtgcaggttga
```

Protein -
SEQ ID NO: 24
```
MPLFNSLCWFPTIHVTPPSFILNGIPGLERVHVWISLPLCTMYIIFLVGNLGLVYLIYYEESLHH

PMYFFFGHALSLIDLLTCTTTLPNALCIFWSLKEINFNACLAQMFFVHGFTGVESGVLMLMALD

RYVAICYPLRYATTLTNPIIAKAELATFLRGVLLMIPFPFLVKRLPFCCSNIISHTYCDHMSVVK
```

-continued

LSCASIKVNVIYGLMVALLIGVFDICCISLSYTLILKAAISLSSSDARQKAFSTCTAHISAIIIT

YVPAFFTFFAHRFGCHTIPPSLHIIVANLYLLLPPTLNPIVYGVKTKQIRKSVIKFFQGDKGAG

OR2L13
DNA -
SEQ ID NO: 25 atggagaaatggaatcacacttcaaatgatttcattttgttgggtctgcttcccccaaatcaaac tggaatatttctcttgtgccttatcatcctcatattctttctggcctcggtgggtaactcggcca tgattcacctcatccacgtggatcctcgtctccacacaccgatgtactttcttctcagccagctc tcccttatggacctgatgtacatctccaccaccgtccccaagatggcgtacaacttcctgtccgg ccagaaaggcatctccttcctgggatgtggtgtgcaaagcttcttcttcctgaccatggcgtgtt ctgaaggcttactcctgacctccatggcctacgaccgttatttggccatctgccactctctctat tatcctatccgcatgagtaaaatgatgtgtgtgaagatgattggaggctcttggacactggggtc catcaactccttggcacacacagtctttgcccttcatattccctactgcaggtctagggctattg accatttcttctgcgatgtcccagccatgttgcttcttgcctgtacagatacttgggtctatgaa tatatggttttgtaagtacaagcctctttctccttttcccttcattggcatcacttcttcctg tggccgagtcctatttgctgtctatcatatgcactcaaaggaggggagaaaaaaggccttcacca ccatttcaacacatttaactgtagtgatcttttactatgcacctttgtctacacctatcttcgg cccaggaatctccgctcaccagctgaagacaagatcctggcagtcttctacaccatccttacccc catgctcaatcccattatctacagcctgaggaataaggaagtcctgggggctatgaggagagtgt ttgggatattctctttcctgaaagaataa Protein -
SEQ ID NO: 26
MEKWNHTSNDFILLGLLPPNQTGIFLLCLIILIFFLASVGNSAMIHLIHVDPRLHTPMYFLLSQL

SLMDLMYISTTVPKMAYNFLSGQKGISFLGCGVQSFFFLTMACSEGLLLTSMAYDRYLAICHSLY

YPIRMSKMMCVKMIGGSWTLGSINSLAHTVFALHIPYCRSRAIDHFFCDVPAMLLLACTDTWVYE

YMVFVSTSLFLLFPFIGITSSCGRVLFAVYHMHSKEGRKKAFTTISTHLTVVIFYYAPFVYTYLR

PRNLRSPAEDKILAVFYTILTPMLNPIIYSLRNKEVLGAMRRVFGIFSFLKE

OR2AJ1
DNA -
SEQ ID NO: 27
atgagtgtaacagaaaatacgctcatgatcctcctcattcgcagtgactcccgactccacactcc aatgtattttctgctcagccatctctccttaatggatatcttgcatgtttccaacatcgttccca aaaatggtcactaactttctgtcaggcagcagaactatttcatttgcaggttgtgggttccaggta tttctgtccctcaccctcctgggtggtgagtgccttctcctggctgcaatgtcctgtgatcgcta tgtggctatctgtcacccgctgcgctatccgattcttatgaaggagtatgccagcgctctcatgg ctggaggctcctggctcattggggttttcaactccacagtccacacagcttatgcactgcagttt cccttctgtggctctagggcaattgatcacttcttctgtgaagtccctgccatgttgaagttgtc ctgtgcagacacaacacgctatgaacgaggggtttgtgtaagtgctgtgatcttcctgctgatcc ctttctccttgatctctgcttcttatggccaaattattcttactgtcctccagatgaaatcatca gaggcaaggaaaaagtcattttccacttgttccttccacatgattgtggtcacgatgtactatgg gccatttattttttacatatatgagacctaaatcataccacactccagggcaggataagttcctgg caatattctatacgatcctcacacccacactcaacccttcatctacagctttaggaataaagat -continued gttctggcggtgatgaaaaatatgctcaaaagtaactttctgcacaaaaaaatgaataggaaaat tcctgaatgtgtgttctgtctatttctatgttaa Protein -

SEQ ID NO: 28

MSVTENTLMILLIRSDSRLHTPMYFLLSHLSLMDILHVSNIVPKMVTNFLSGSRTISFAGCGFQV

FLSLTLLGGECLLLAAMSCDRYVAICHPLRYPILMKEYASALMAGGSWLIGVFNSTVHTAYALQF

PFCGSRAIDHFFCEVPAMLKLSCADTTRYERGVCVSAVIFLLIPFSLISASYGQIILTVLQMKSS

EARKKSFSTCSFHMIVVTMYYGPFIFTYMRPKSYHTPGQDKFLAIFYTILTPTLNPFIYSFRNKD

VLAVMKNMLKSNFLHKKMNRKIPECVFCLFLC

OR4C15
DNA -

SEQ ID NO: 29 atgttctcaatgacaacagaagcactcaataattttgcacttggatgtaccaacttgttaatgac tatgataccacaaattgatctgaagcaaattttcctttgtcctaattgcagactatacatgatcc ctgttggagctttcatcttttccttgggaaacatgcaaaccaaagctttgtaactgagtttgtc ctcctgggactttcacagaatccaaatgttcaggaaatagtatttgttgtattttttgtttgtcta cattgcaactgttgggggcaacatgctaattgtagtaaccattctcagcagccctgctcttctgg tgtctcctatgtacttcttcttgggcttcctgtccttcctggatgcgtgcttctcatctgtcatc accccaaagatgattgtagactccctctatgtgacaaaaaccatctcttttgaaggctgcatgat gcagctctttgctgaacacttctttgctggggtggaggtgattgtcctcacagccatggcctatg atcgttatgtggccatttgcaagcccttgcattactcttctatcatgaacaggaggctctgtggc attctgatgggggtagcctggacagggggcctcttgcattccatgatacaaattctttttactttt ccagcttccccttttgtggccccaatgtcatcaatcactttatgtgtgacttgtacccgttactgg agcttgcctgcactgatactcacatctttggcctcatggtggtcatcaacagtgggtttatctgc atcataaacttctccttgttgcttgtctcctatgctgtcatcttgctctctctgagaacacacag ttctgaagggcgctggaaagctctctccacctgtggatctcacattgctgttgtgattttgttct ttgtcccatgcatatttgtatatacacgacctccatctgcttttttcccttgacaaaatggcggca atattttatatcatcttaaatcccttgctcaatcctttgatttacactttcaggaataaggaagt aaaacaggccatgaggagaatatggaacagactgatggtggtttctgatgagaaagaaaatatta aactttaa Protein -

SEQ ID NO: 30

MFSMTTEALNNFALGCTNLLMTMIPQIDLKQIFLCPNCRLYMIPVGAFIFSLGNMQNQSFVTEFV

LLGLSQNPNVQEIVFVVFLFVYIATVGGNMLIVVTILSSPALLVSPMYFFLGFLSFLDACFSSVI

TPKMIVDSLYVTKTISFEGCMMQLFAEHFFAGVEVIVLTAMAYDRYVAICKPLHYSSIMNRRLCG

ILMGVAWTGGLLHSMIQILFTFQLPFCGPNVINHFMCDLYPLLELACTDTHIFGLMVVINSGFIC

IINFSLLLVSYAVILLSLRTHSSEGRWKALSTCGSHIAVVILFFVPCIFVYTRPPSAFSLDKMAA

IFYIILNPLLNPLIYTFRNKEVKQAMRRIWNRLMVVSDEKENIKL

OR5AC2
DNA -

SEQ ID NO: 31 atggatatatcagagggaaataagactcttgtgacagagtttgttctcacaggacttacagatcg accatggctgcacgtcctcttctttgttgtgttttttggtggtctatctcatcaccatggtgggca accttggactgatagttctaatttggaacgaccccccatcttcatatgcccatgtacttattcctt ggtggtttagccttttcagatgcttgtacttcaacctctataaccctaggatgctggtcaattt cttagacaagactgcaatgatatccctagctgagtgcatcacccagttttactttttttgcttcca

```
gtgcaactacagaatgcttcctcctggtgatgatggcctatgaccgctatgtagccatatgtaat cccttgctttatccagtgatgatgtccaacaaactcagcgctcagttgctaagtatttcatatgt aattggtttcctgcatcctctggttcatgtgagtttactattgcgactaactttctgcaggttta acataatacattatttctactgtgaaattttacaactgttcaaaatttcatgcaatggtccatct attaacgcactaatgatatttattttggtgcttttatacaaatacccactttaatgactatcat aatctcttatactcgtgtgctctttgatattctgaaaaaaaagtctgaaaagggcagaagcaaag ccttctccacatgcggcgcccatctgctttctgtctcattgtactacggaactctgatcttcatg tatgtgcgtcctgcatctggcttagctgaagaccaagacaaagtgtattctctgttttacacgat tataattcccctgctaaacccatttatttacagcttgagaataaaaaagtcatgcatgcattga gaagagttataaggaagtaa
```

Protein -

SEQ ID NO: 32

```
MDISEGNKTLVTEFVLTGLTDRPWLHVLFFVVFLVVYLITMVGNLGLIVLIWNDPHLHMPMYLFL

GGLAFSDACTSTSITPRMLVNFLDKTAMISLAECITQFYFFASSATTECFLLVMMAYDRYVAICN

PLLYPVMMSNKLSAQLLSISYVIGFLHPLVHVSLLLRLTFCRFNIIHYFYCEILQLFKISCNGPS

INALMIFIFGAFIQIPTLMTIIISYTRVLFDILKKKSEKGRSKAFSTCGAHLLSVSLYYGTLIFM

YVRPASGLAEDQDKVYSLFYTIIIPLLNPFIYSLRNKKVMHALRRVIRK
```

OR8H3
DNA -

SEQ ID NO: 33

```
atgatgggtagaaggaatgacacaaatgtggctgacttcatccttacgggactgtcagactctga agaggtccagatggctctgtttatgctatttctcctcatataccatattactatgctggggaatg tggggatgctattgataatccgcctggacctccagcttcacactcccatgtatttttccttact cacctgtcatttattgacctcagttactcaactgtcgtcacacctaaaaaccttagcgaacttact gacttccaactatatttccttcacgggctgctttgcccagatgttctgttttgtcttcttgggta ctgctgaatgttatcttctctcctcaatggcctatgatcgctatgcagcgatctgcagtcctcta cactacacagttattatgcccaaaaggctctgcctcgctctcatcactgggccttatgtgattgg ctttatggactcctttgtcaatgtggtttccatgagcagattgcatttctgtgactcaaacataa ttcatcacttttctgtgacacttccccaattttagctctgtcctgcactgacacagacaacact gaaatgctgatattcattatcgctggttccaccctgatggtgtccccttatcacaatatctgcatc ctatgtgtccattctctctaccatcctgaaaattaattccacttcaggaaagcagaaagctttct ctacttgcgtctctcatctcttgggagtcaccatcttctatggaactatgattttttacttactta aagccaagaaagtcttattccttgggaagagatcaagtggctcctgtgttttatactattgtgat tcccatgctgaatccactcatttatagtcttagaaacagagaagtgaaaaatgctctcattagag tcatgcagagaagacaggactccaggtag
```

Protein -

SEQ ID NO: 34

```
MVGRRNDTNVADFILTGLSDSEEVQMALFMLFLLIYLITMLGNVGMLLIIRLDLQLHTPMYFFLT

HLSFIDLSYSTVVTPKTLANLLTSNYISFTGCFAQVFCFVFLGTAECYLLSSMAYDRYAAICSPL

HYTVIMPKRLCLALITGPYVIGFMDSFVNVVSMSRLHFCDSNIIHHFFCDTSPILALSCTDTDNT
```

EMLIFIIAGSTLMVSLITISASYVSILSTILKINSTSGKQKAFSTCVSHLLGVTIFYGTMIFTYL

KPRKSYSLGRDQVAPVFYTIVIPMLNPLIYSLRNREVKNALIRVMQRRQDSR

OR11G2
DNA - SEQ ID NO: 35 atgaaaatcttcaacagccccagcaactccagcaccttcactggcttcatcctcctgggcttccc
ttgccccagggaggggcagatcctcctctttgtgctcttcactgttgtttacctcctgaccctca
tgggcaatggttccatcatctgtgctgtgcactgggatcagagactccacgcccccatgtacatc
ctgctcgccaacttctccttcttggagatatgttatgtcacctccacagtccccagcatgctggc
caacttcctctctgacaccaagatcatctcgttctctggctgcttcctccagttctacttttttct
tctccttgggctctacagaatgcttttcctggcagttatggcatttgatcgataccttgccatc
tgtcggcctctacgctatccaaccattatgaccagacgtctctgtaccaatcttgtggtcaattg
ctgggtacttggtttcatctggttcttgattcctatcgtcaacatctcccaaatgtccttctgtg
gatctaggattattgaccacttcctatgtgacccagctcctcttctaactctcacttgcaaaaaa
ggccctgtgatagagcttgtcttttctgtcttaagtcctctgcctgtctttatgctctttctctt
cattgtgggtcctatgctctggtcgtgagagctgtgttgagggtcccttcagcagctgggagaa
gaaaggctttctccacctgtgggtctcacctggctgtggtttcactgttctacggctcagtactg
gtcatgtatgggagcccaccatctaagaatgaagctggaaagcagaagactgtgactctgtttta
ttctgttgttaccccactgcttaaccctgtgatatatagtcttaggaacaaagatatgagaaaag
ctctgaagaaatttggggaacataa Protein - SEQ ID NO: 36

MKIFNSPSNSSTFTGFILLGFPCPREGQILLFVLFTVVYLLTLMGNGSIICAVHWDQRLHAPMYI

LLANFSFLEICYVTSTVPSMLANFLSDTKIISFSGCFLQFYFFFSLGSTECFFLAVMAFDRYLAI

CRPLRYPTIMTRRLCTNLVVNCWVLGFIWFLIPIVNISQMSFCGSRIIDHFLCDPAPLLTLTCKK

GPVIELVFSVLSPLPVFMLFLIVGSYALVVRAVLRVPSAAGRRKAFSTCGSHLAVVSLFYGSVL

VMYGSPPSKNEAGKQKTVTLFYSVVTPLLNPVIYSLRNKDMRKALKKFWGT

OR52N2
DNA - SEQ ID NO: 37 atgtctggggacaacagctccagcctgaccccaggattcttatcttgaatggcgttcctgggct
ggaagccacacacatctggatctccctgccattctgctttatgtacatcattgctgtcgtgggga
actgtgggctcatctgcctcatcagccatgaggaggccctgcaccggcccatgtactacttcctg
gccctgctctccttcactgatgtcaccttgtgcaccaccatggtacctaatatgctgtgcatatt
ctggttcaacctcaaggagattgactttaacgcctgcctggcccagatgttttttgtccatatgc
tgacagggatggagtctggggtgctcatgctcatggccctggaccgctatgtggccatctgctac
cccttacgctatgccaccatccttaccaaccctgtcatcgccaaggctggtcttgccaccttctt
gaggaatgtgatgctcatcatcccattcactctcctcaccaagcgcctgccctattgccggggga
acttcatcccccacacctactgtgaccatatgtctgtggccaaggtatcctgtggcaatttcaag
gtcaatgctatttatggtctgatggttgctctcctgattggtgtgtttgatatctgctgtatctc
tgtatcttacactatgattttgcaggctgttatgagcctgtcatcagcagatgctcgtcacaaag
ccttcagcacctgcacatctcacatgtgttccattgtgatcacctatgttgctgctttttcact
tttttcactcatcgttttgtaggacacaatatcccaaaccacatacacatcatcgtggccaacct
ttatctgctactgcctcctaccatgaacccaattgtttatggagtcaagaccaagcagattcagg
aaggtgtaattaaattttttacttggagacaaggttagttttacctatgacaaatga Protein -
SEQ ID NO: 38
MSGDNSSSLTPGFFILNGVPGLEATHIWISLPFCFMYIIAVVGNCGLICLISHEEALHRPMYYFL

ALLSFTDVTLCTTMVPNMLCIFWFNLKEIDFNACLAQMFFVHMLTGMESGVLMLMALDRYVAICY

PLRYATILTNPVIAKAGLATFLRNMMLIIPFTLLTKRLPYCRGNFIPHTYCDHMSVAKVSCGNFK

VNAIYGLMVALLIGVFDICCISVSYTMILQAVMSLSSADARHKAFSTCTSHMCSIVITYVAAFFT

FFTHRFVGHNIPNHIHIIVANLYLLLPPTMNPIVYGVKTKQIQEGVIKFLLGDKVSFTYDK

OR5T1
DNA -
SEQ ID NO: 39
atgtttatattaataagcttcacagaagaatttgatgtgcaagtcttcctattttattattttt agcaatctatctattcactctaataggcaatttagggctggttgtaccgatcattgggatttct ggcttcacagcccaatgtactattttcttggtgttttatcattcttggatgtctgctattctaca gttgtcactccaaaaatgttggtcaatttcctggcaaaaataaatctatttcatttcttggatg tgcaacacagatgttcttgcttgtacttttggaaccacagaatgctttctcttggctgcaatgg cttatgatcgctatgtagccatctacaaccctctcctgtattcagtgagcatgtcacccagagtc tatgtgccactcatcactgcttcctatgttgctagcattttacatgctactatacatacagtggc tacatttagcctgtccttctgtggatccaatgaaattaggcatgtcttttgtaatatgcctcctc tccttgctatttcttgttctgacactcacgtaatccagcttctattcttctactttgtgggctct attgagatagtcactatcctgattgtcctgatctcctatggttttattctgttggccattctgaa gatgcagtctgctgaagggaggagaaaagtcttctctacatgtgagctcacctaactggagtga caatttatcatgggacaatcctcttcatgtatgtgagaccaagttccagctacacttcggacaat gacatgatagtgtcaatattttataccattgtgattcccatgctgaatcccatcatctacagttt gcggaacaaagatgtaaaggaggcaatcaaaagattgcttgtgagaaattggttcataaataagt tatag Protein -
SEQ ID NO: 40
MFILISFTEEFDVQVFLFLLFLAIYLFTLIGNLGLVVPIIGDFWLHSPMYYFLGVLSFLDVCYST

VVTPKMLVNFLAKNKSISFLGCATQMFLACTFGTTECFLLAAMAYDRYVAIYNPLLYSVSMSPRV

YVPLITASYVASILHATIHTVATFSLSFCGSNEIRHVFCNMPPLLAISCSDTHVIQLLFFYFVGS

IEIVTILIVLISYGFILLAILKMQSAEGRRKVFSTCGAHLTGVTIYHGTILFMYVRPSSSYTSDN

DMIVSIFYTIVIPMLNPIIYSLRNKDVKEAIKRLLVRNWFINKL

OR4S2
DNA -
SEQ ID NO: 41
atggaaaaaataaacaacgtaactgaattcattttctggggtcttctcagagcccagagattga gaaagtttgttttgtggtgttttcttcttctacataatcattcttctgggaaatctcctcatca tgctgacagtttgcctgagcaacctgtttaagtcacccatgtatttctttctcagcttcttgtct tttgtggacatttgttactcttcagtcacagctcccaagatgattgttgacctgttagcaagga caaaaccatctcctatgtgggtgcatgttgcaactgtttggagtacatttctttggttgcactg agatcttcatccttactgtaatggcctatgatcgttatgtggctatctgtaaaccctacattat atgaccatcatgaaccgggagacatgcaataaaatgttattagggacgtgggtaggtgggttctt acactccattatccaagtggctctggtagtccaactacccttttgtggacccaatgagatagatc actacttttgtgatgttcaccctgtgttgaaacttgcctgcacagaaacatacattgttggtgtt ggtgtgacagccaacagtggtaccattgctctggggagttttgttatcttgctaatctcctacag -continued catcatcctagtttccctgagaaagcagtcagcagaaggcaggcgcaaagccctctccacctgtg gctcccacattgccatggtcgttatcttttcggccctgtacttttatgtacatgcgccctgat acgaccttttcagaggataagatggtggctgtattttacaccattatcactcccatgttaaatcc tctgatttatacactgagaaatgcagaagtaaagaatgcaatgaagaaactgtggggcagaaatg ttttcttggaggctaaagggaaatag Protein -
SEQ ID NO: 42

MEKINNVTEFIFWGLSQSPEIEKVCFVVFSFFYIIILLGNLLIMLTVCLSNLFKSPMYFFLSFLS

FVDICYSSVTAPKMIVDLLAKDKTISYVGCMLQLFGVHFFGCTEIFILTVMAYDRYVAICKPLHY

MTIMNRETCNKMLLGTWVGGFLHSIIQVALVVQLPFCCPNEIDHYFCDVHPVLKLACTETYIVGV

VVTANSGTIALGSFVILLISYSIILVSLRKQSAEGRRKALSTCGSHIAMVVIFFGPCTFMYMRPD

TTFSEDKMVAVFYTIITPMLNPLIYTLRNAEVKNAMKKLWGRNVFLEAKGK

FLAG ® tag
DNA -
SEQ ID NO: 43 gattacaaggacgacgacgataag

Protein -
SEQ ID NO: 44

DYKDDDDK

Rho tag
DNA -
SEQ ID NO: 45 atgaacgggaccgagggcccaaacttctacgtgcctttctccaacaagacgggcgtggtg

Protein -
SEQ ID NO: 46

MNGTEGPNFYVPFSNKTGVV

Lucy tag
DNA -
SEQ ID NO: 47 atgagaccccagatcctgctgctcctggccctgctgaccctaggcctggct

Protein -
SEQ ID NO: 48

MRPQILLLLALLTLGLA

Human G-protein alpha subunit G$_{olf}$
DNA -
SEQ ID NO: 49 atgggtctgtgctacagtctgcggccgctgcttttcggggggcccaggggacgaccctgcgcggc ctcggagccgccggtggaggacgcgcagccccgccccggccccggccctgccccagtccgggcgg ccgcaagggacacggccccggaccctgctccctcggggcggcgaagggagcccggcatgcgctcgg cccaaagcagacaagccgaaggagaagcggcagcgcaccgagcagcttagtgccgaggagcgcga ggcggccaaggagcgcgaggcggtcaaggaggcgaggaaagtgagcggggcatcgaccgcatgc tgcgcgaccagaagcgcgacctgcagcagacgcaccggctcctgctgctcggggctggtgagtct gggaaaagcactatcgtcaaacagatgaggatcctgcacgtcaatgggtttaatcccgaggaaaa gaaacagaaaattctggacatccggaaaaatgttaaagatgctatcgtgacaattgtttcagcaa tgagtactataatacctccagttccgctggccaaccctgaaaaccaatttcgatcagactacatc aagagcatagccctatcactgactttgaatattcccaggaattctttgaccatgtgaaaaaact ttgggacgatgaaggcgtgaaggcatgctttgagagatccaacgaataccagctgattgactgtg cacaatacttcctggaaagaatcgacagcgtcagcttggttgactacacacccacagaccaggac ctcctcagatgcagagttctgacatctgggattttgagaacgattccaagtggacaaagtaaac ttccacatgtttgatgttggtggcagagggatgagaggagaaaatggatccagtgctttaacga tgtcacagctatcatttacgtcgcagcctgcagtagctacaacatggtgattcgagaagataaca -continued acaccaacaggctgagagagtccctggatcttttttgaaagcatctggaacaacaggtggttacgg accatttctatcatcttgttcttgaacaaacaagatatgctggcagaaaaagtcttggcagggaa atcaaaaattgaagactatttcccagaatatgcaaattatactgttcctgaagacgcaacaccag atgcaggagaagatcccaaagttacaagagccaagttctttatccgggacctgttttttgaggatc agcacggccaccggtgacggcaaacattactgctacccgcacttcacctgcgccgtggacacaga gaacatccgcagggtgttcaacgactgccgcgacatcatccagcggatgcacctcaagcagtatg agctcttgtga Protein -

SEQ ID NO: 50

MGLCYSLRPLLFGGPGDDPCAASEPPVEDAQPAPAPALAPVRAAARDTARTLLPRGGEGSPACAR

PKADKPKEKRQRTEQLSAEEREAAKEREAVKEARKVSRGIDRMLRDQKRDLQQTHRLLLLGAGES

GKSTIVKQMRILHVNGFNPEEKKQKILDIRKNVKDAIVTIVSAMSTIIPPVPLANPENQFRSDYI

KSIAPITDFEYSQEFFDHVKKLWDDEGVKACFERSNEYQLIDCAQYFLERIDSVSLVDYTPTDQD

LLRCRVLTSGIFETRFQVDKVNFHMFDVGGQRDERRKWIQCFNDVTAIIYVAACSSYNMVIREDN

NTNRLRESLDLFESIWNNRWLRTISIILFLNKCDMLAEKVLAGKSKIEDYFPEYANYTVPEDATP

DAGEDPKVTRAKFFIRDLFLRISTATGDGKHYCYPHFTCAVDTENIRRVFNDCRDIIQRMHLKQY

ELL

Human G-protein alpha subunit Gα15
DNA -

SEQ ID NO: 51 atggcccggtcgctgacctggcgctgctgcccctggtgcctgacggaggatgagaaggccgccgc ccgggtggaccaggagatcaacaggatcctcttggagcagaagaagcaggaccgcggggagctga agctgctgcttttgggcccaggcgagagcgggaagagcaccttcatcaagcagatgcggatcatc cacggcgccggctactcggaggaggagcgcaagggcttccggcccctggtctaccagaacatctt cgtgtccatgcgggccatgatcgaggccatggagcggctgcagattccattcagcaggcccgaga gcaagcaccacgccagcctggtcatgagccaggacccctataaagtgaccacgtttgagaagcgc tacgctgcggccatgcagtggctgtggagggatgccggcatccgggcctgctatgagcgtcggcg ggaattccacctgctcgattcagccgtgtactacctgtcccacctggagcgcatcaccgaggagg gctacgtccccacagctcaggacgtgctccgcagccgcatgcccaccactggcatcaacgagtac tgcttctccgtgcagaaaaccaacctgcggatcgtggacgtcgggggccagaagtcagagcgtaa gaaatggatccattgtttcgagaacgtgatcgccctcatctacctggcctcactgagtgaatacg accagtgcctggaggagaacaaccaggagaaccgcatgaaggagagcctcgcattgtttgggact atcctggaactaccctggttcaaaagcacatccgtcatcctctttctcaacaaaaccgacatcct ggaggagaaaatccccacctcccacctggctacctatttccccagtttccagggccctaagcagg atgctgaggcagccaagaggttcatcctggacatgtacacgaggatgtacaccgggtgcgtggac ggccccgagggcagcaagaagggcgcacgatcccgacgcctcttcagccactacacatgtgccac agacacacagaacatccgcaaggtcttcaaggacgtgcgggactcggtgctcgcccgctacctgg acgagatcaacctgctgtgtga Protein -

SEQ ID NO: 52

MARSLTWRCCPWCLTEDEKAAARVDQEINRILLEQKKQDRGELKLLLLGPGESCKSTFIKQMRII

HGAGYSEEERKGFRPLVYQNIFVSMRAMIEAMERLQIPFSRPESKHHASLVMSQDPYKVTTFEKR

YAAAMQWLWRDAGIRACYERRREFHLLDSAVYYLSHLERITEEGYVPTAQDVLRSRMPTTGINEY

CFSVQKTNLRIVDVGGQKSERKKWIHCFENVIALIYLASLSEYDQCLEENNQENRMKESLALFGT

-continued

ILELPWFKSTSVILFLNKTDILEEKIPTSHLATYFPSFQGPKQDAEAAKRFILDMYTRMYTGCVD

GPEGSKKGARSRRLFSHYTCATDTQNIRKVFKDVRDSVLARYLDEINLL

SEQ ID NO: 53

Motif
MAYDRYVAIC

SEQ ID NO: 54

Motif
FSTCSSH

SEQ ID NO: 55

Motif
PMLNPFIY

The following examples are illustrative only and are not meant to limit the scope of invention as set forth in the Summary, Description or in the Claims.

EXAMPLES

Example 1

Identification of Novel Mouse and Human DMTS Activated Odorant Receptors

The identification of new odorant receptors was performed according to the method disclosed in WO2014/210585. Briefly, murine olfactory sensory neurons were exposed to DMTS and screened using a $Ca^{2+}$ imaging technique. Neurons that were activated by DMTS were further isolated for full transcriptome analysis to identify the responsive odorant receptor. The cDNA corresponding to the isolated cell mRNA was generated and amplified by PCR based method (Clontech/Takara, SMARTer® Ultra® Low Input RNA Kit for Sequencing—v3, cat. 634848). Amplified cDNA was then used to generate an Illumina cDNA library for Next-Generation-Sequencing and the generation of 100 base pair single read sequences. Sequences were aligned to a mouse reference genome (such as UCSC version mm10) in order to generate the full transcriptome. Because only a single odorant receptor (OR) is strongly transcribed per olfactory sensory neuron, the subsequent identification of the DMTS responsive OR can be achieved. Phylogenetic relationship evaluation using sequence similarity searches were then used to identify the corresponding human OR. Similar functional response profiles between orthologous OR pairs are often observed [e.g. Adipietro, K. A, et al. PLoS Genet. 8, e1002821-e1002821 (2012), Sato-Akuhara, N. et al. J. Neurosci. 36, 4482-4491 (2016) and WO2016/201152] and can be used for human OR identification [e.g. Armelin-Correa L. M. and Malnic B. J Agric Food Chem. doi: 10.1021/acs.jafc.6b04998 (2017)]. FIG. 1 shows the pairwise identity levels between the receptors mentioned herein. ORs that do not share an orthologous and/or paralogous relationship only share an average of 39%±13.1%. All orthologous and paralogous relationship share an average of 77%±7.5%. All paralogs and orthologs pairs are indicated by a gray shaded cell. They represent the highest identity levels as supported by the amino acid identity levels indicated.

Example 2

Functional Characterization of Mouse and Human DMTS Receptors

Functional dose-response experiments were performed to evaluate the level of DMTS activity of the modified cell line expressing individual putative DMTS receptors. Using a cell-based assay, mouse receptor Olfr1193, Olfr1093, Olfr1097, Olrfl66, Olfr169, Olfr738 and Olfr742, and human receptor OR4S2 and OR52N5 were tested in an HEK293T cell line wherein the endogenous RTP1 gene has been activated and the odorant receptor chaperone protein was expressed (described in WO2016/201153). The mouse receptor genes were tagged with a Lucy-FLAG®-Rho tag combination and the human receptors were tagged with a Rho-FLAG® tag combination resulting in a tag:receptor fusion protein for the cell based assay. Receptor genes were co-transfected with the canonical olfactory human G-protein alpha subunit Golf gene and were exposed to increasing concentrations of the malodor odorant. Co-expression of the human Golf activates the Gs transduction pathway that leads to an internal cAMP increase upon binding to the appropriate ligand. Odorant-induced activity was detected by measuring the cAMP increase in the cytosol using an Homogeneous Time Resolved Fluorescence (HTRF) based kit (CisBio, cAMP dynamic 2 kit, cat. 62AM4PEJ). A dose-dependent increase of the receptor activity is observed specifically for DMTS but not for butyric acid, another known malodor used as a negative control (FIG. 1). The activity levels are reported by the potency of the DMTS induced-response for each receptor as a measure of the EC50 value (the effective concentration at which the receptor responds at its half-maximal activation efficacy level for a given compound).

Example 3

Functional Characterization of Additional Human DMTS Receptors

Figure 2:
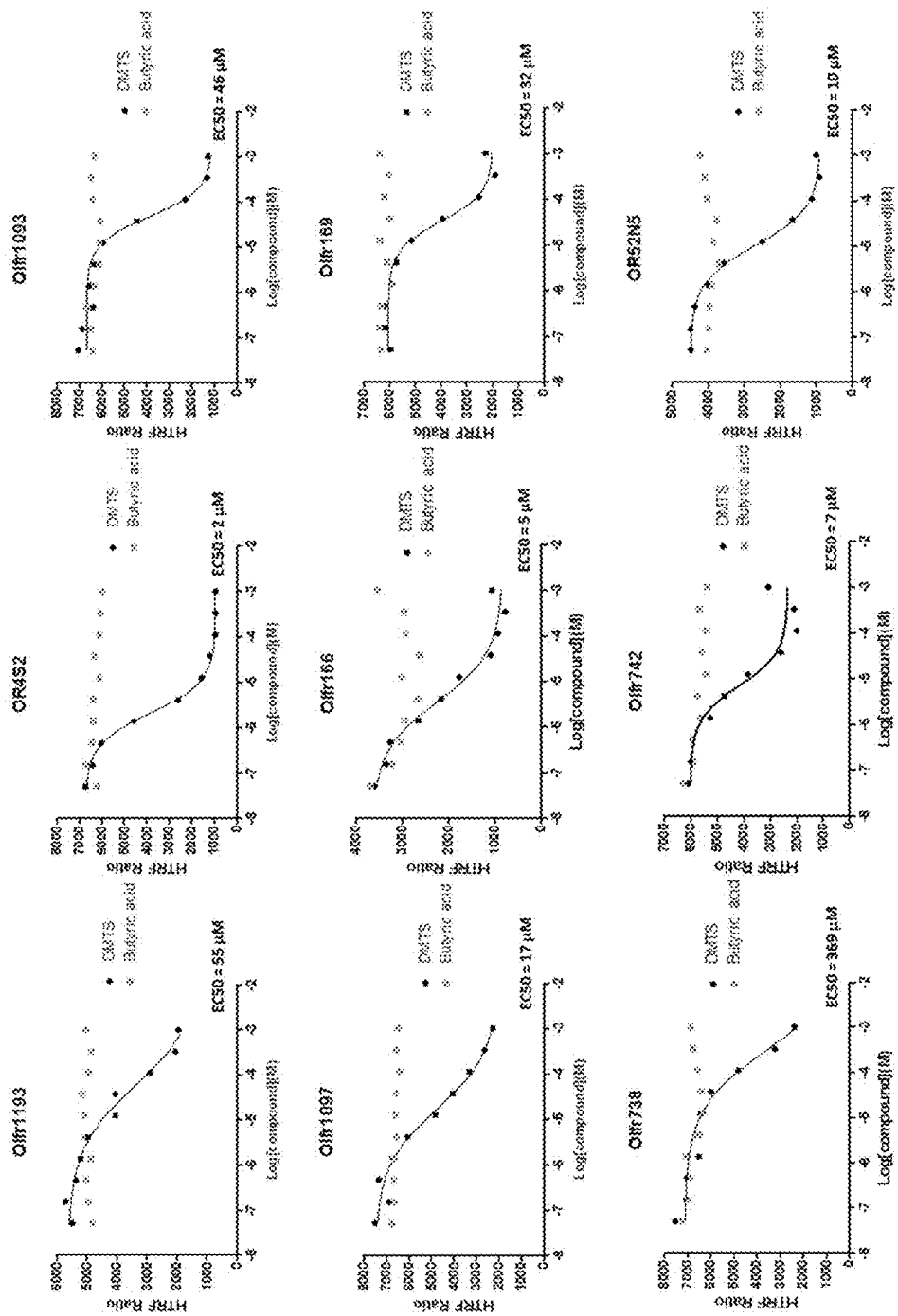
FIG. 2 shows DMTS dose response curves of mouse odorant receptors Olfr1193, Olfr1093, Olfr1097, Olfr166, Olfr169, Olfr738 and Olfr742, and of human odorant receptors OR4S2 and OR52N5.
Figure 3:
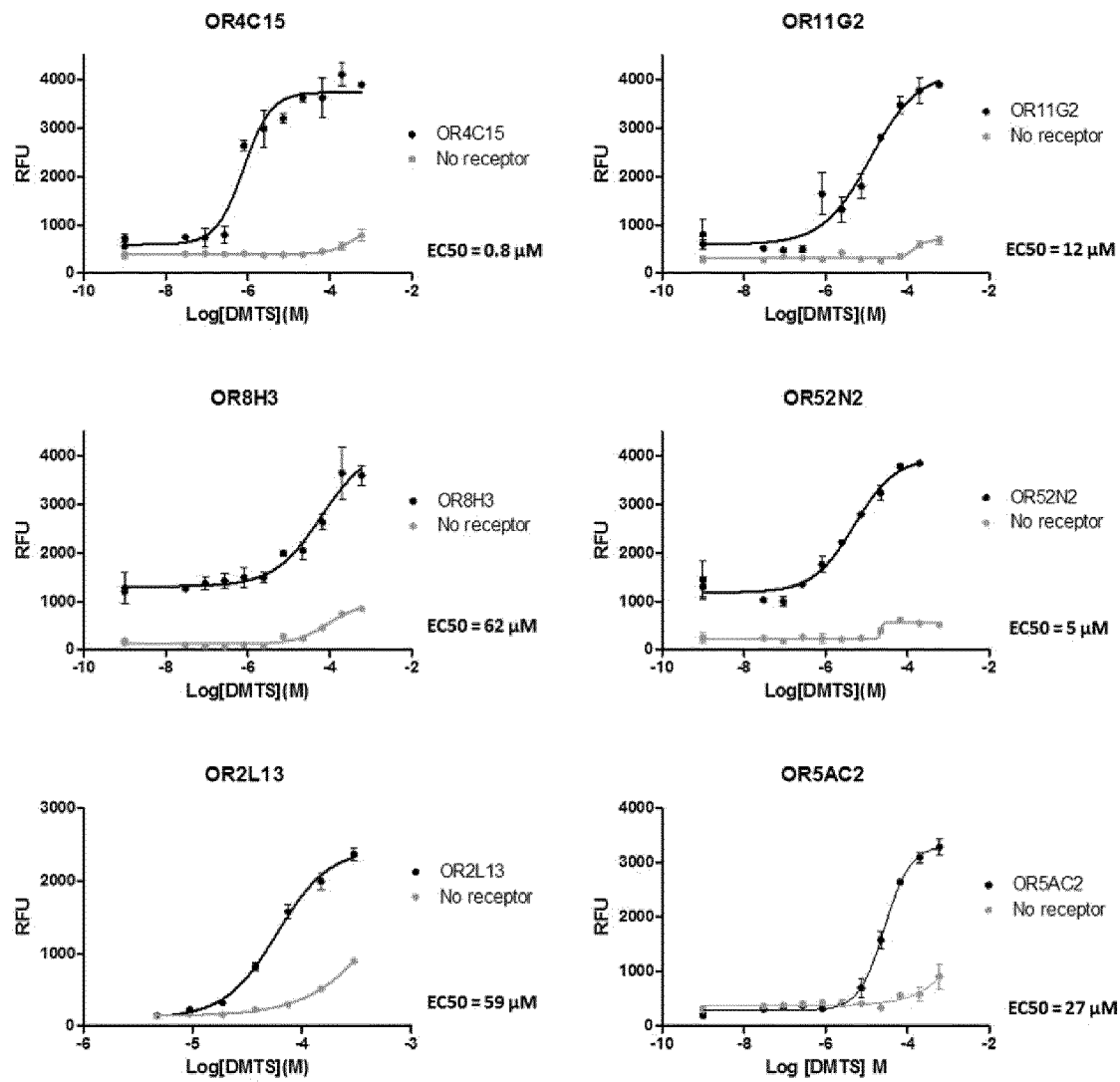
FIG. 3 shows DMTS dose response curves of human odorant receptors OR2L13, OR4C15, OR8H3, OR11G2 and OR52N2.

Functional dose-response experiments were performed to evaluate the level of DMTS activity of the modified cell lines expressing individual putative DMTS receptors. A cell line stably expressing a human receptor was generated in a HEK293T cell line for each of the following human receptors: OR2L13, OR4C15, OR5AC2, OR8H3, OR11G2 or OR52N2. The receptors were tagged with a FLAG®-Rho tag combination and stably co-expressed with the human G-protein alpha subunit Gals for the cell based assay. Co-expression of the human Gals activates the Gq transduction pathway that leads to an internal $Ca^{2+}$ increase upon binding to the appropriate ligand. Receptors were exposed to increasing concentrations of DMTS. Odorant-induced activity was detected by measuring the $Ca^{2+}$ increase in the cytosol using a calcium sensitive fluorescent dye (Molecular Devices, Calcium 5 dye, cat. R8186) and measuring the change in Relative Fluorescence Ratio (RFU) using a fluorometric imaging plate reader (Molecular Devices, FLIPR)

following odorant exposure. A dose-dependent increase of receptor activity was recorded and a corresponding dose-response curve is shown for DMTS (FIG. 2). A cell line lacking a receptor was used as a control for non-specific activity at high compound concentrations ('No receptor'). The activity levels are reported by the potency of the DMTS induced-response for each receptor as a measure of the EC50 value.

Example 4

Identification of DMTS Receptor Inhibitors

The stable cell lines described in Example 3 were used as an antagonist screening platform to identify compounds that have the property to decrease the DMTS induced receptor activity. Each stable cell line expressing a human odorant receptor was screened with a volatile compound library for their inhibitory properties and potential DMTS smell inhibition. First, individual binary mixtures of DMTS with each one of the test compounds were presented to the cells. Single point monitoring of the DMTS induced cell activity in the presence or absence of a test compound allowed for the identification of compounds with a putative suppression or inhibitory effect. These hits were further confirmed in an inhibitory dose-response curve assay to evaluate the potency of activity inhibition as a measure of the IC50 (the inhibitor concentration at which the receptor activity is inhibited by the half-maximal inhibition efficacy level of a given test compound). A dose-dependent decrease of receptor activity was recorded with increasing concentrations of test compounds in the presence of a single activating concentration of DMTS (EC80) and corresponding dose-response inhibition curves were obtained. The compounds in the following table are examples of compounds that decreased the DMTS induced activity of at least one receptor as depicted in FIG. 4.

| | |
|---|---|
| Cyclemone A | 1,2,3,4,5,6,7,8-octahydro-8,8-dimethyl-2-naphthalenecarbaldehyde (A) + (B,C,D) + octahydro-5,5-dimethyl-2-naphthalenecarbaldehyde |
| Geonol | (+-)-perhydro-4alpha,8abeta-dimethyl-4a-naphthalenol |
| Hivernal | 3-(3,3-dimethyl-2,3-dihydro-1H-inden-5-yl)propanal |
| Neo ® | (A) + 3-(1,1-dimethyl-2,3-dihydro-1H-inden-4-yl)propanal (B) + 3-(1,1-dimethyl-2,3-dihydro-1H-inden-5-yl)propanal (C) |
| Lilyflore ® | (+-)-2,5-dimethyl-2-indanmethanol |
| Patchouli alcohol | (-)- (3R,6S ,8S)-2,2,6,8-tetramethyltricyclo[5.3.1.0~3,8~]undecan-3-ol |
| Patchouli Oil | patchouli oil |
| Rosinol Cryst | (+-)-2,2,2-trichloro-1-phenylethyl acetate |
| Spiranol ® | 5RS,6RS)-2,6,10,10-tetramethyl-1-oxaspiro[4.5]decan-6-ol |
| Terranol | 2,2,7,7-tetramethyltricyclo[6.2.1.0~1,6~]undecan-6-ol |
| Wolfwood ® | (+)-(1S,2S,3S,5R)-2,6,6-trimethylspiro[bicyclo[3.1.1]heptane-3,1'-cyclohexane]-2'-en-4'-one |

Figure 4:
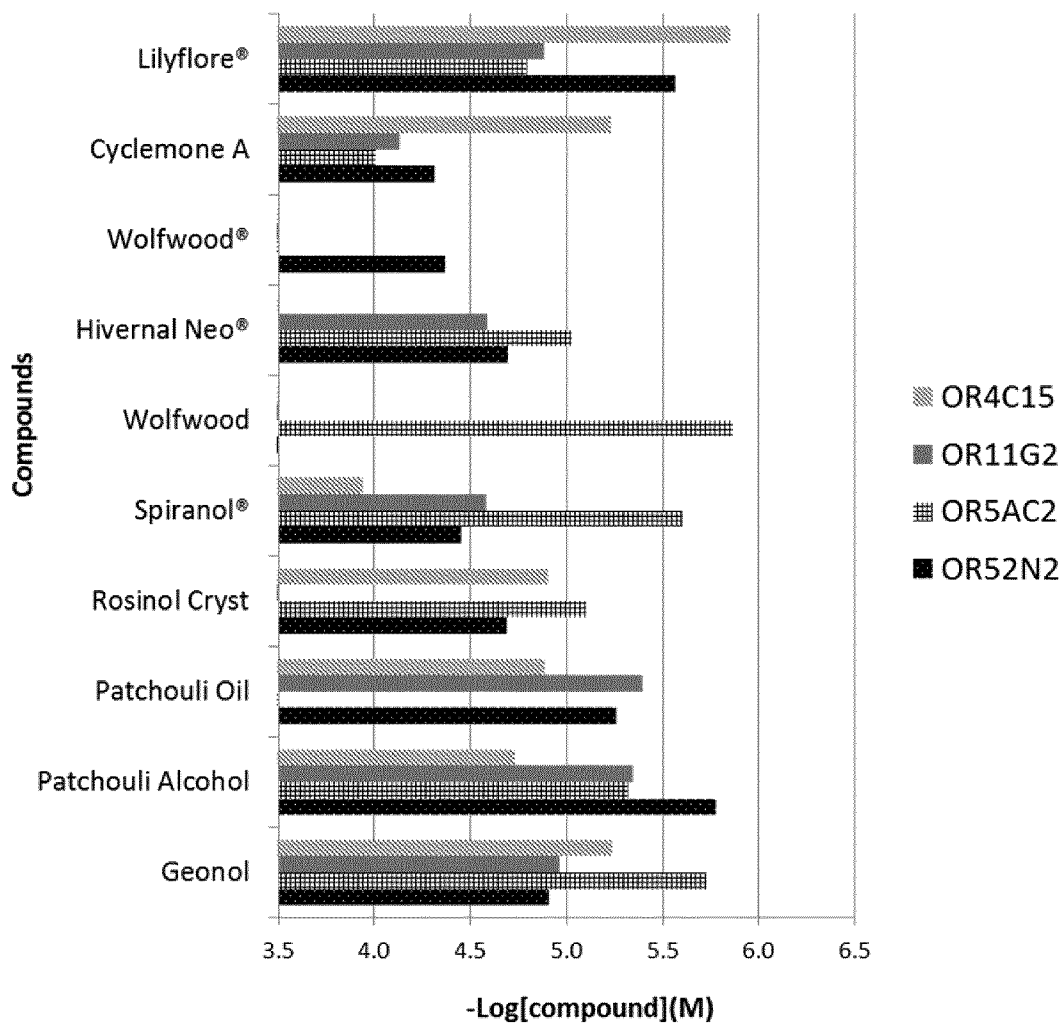
FIG. 4 shows a ranking of volatile compounds with specific inhibitory effects on DMTS receptor activity.
Figure 5:
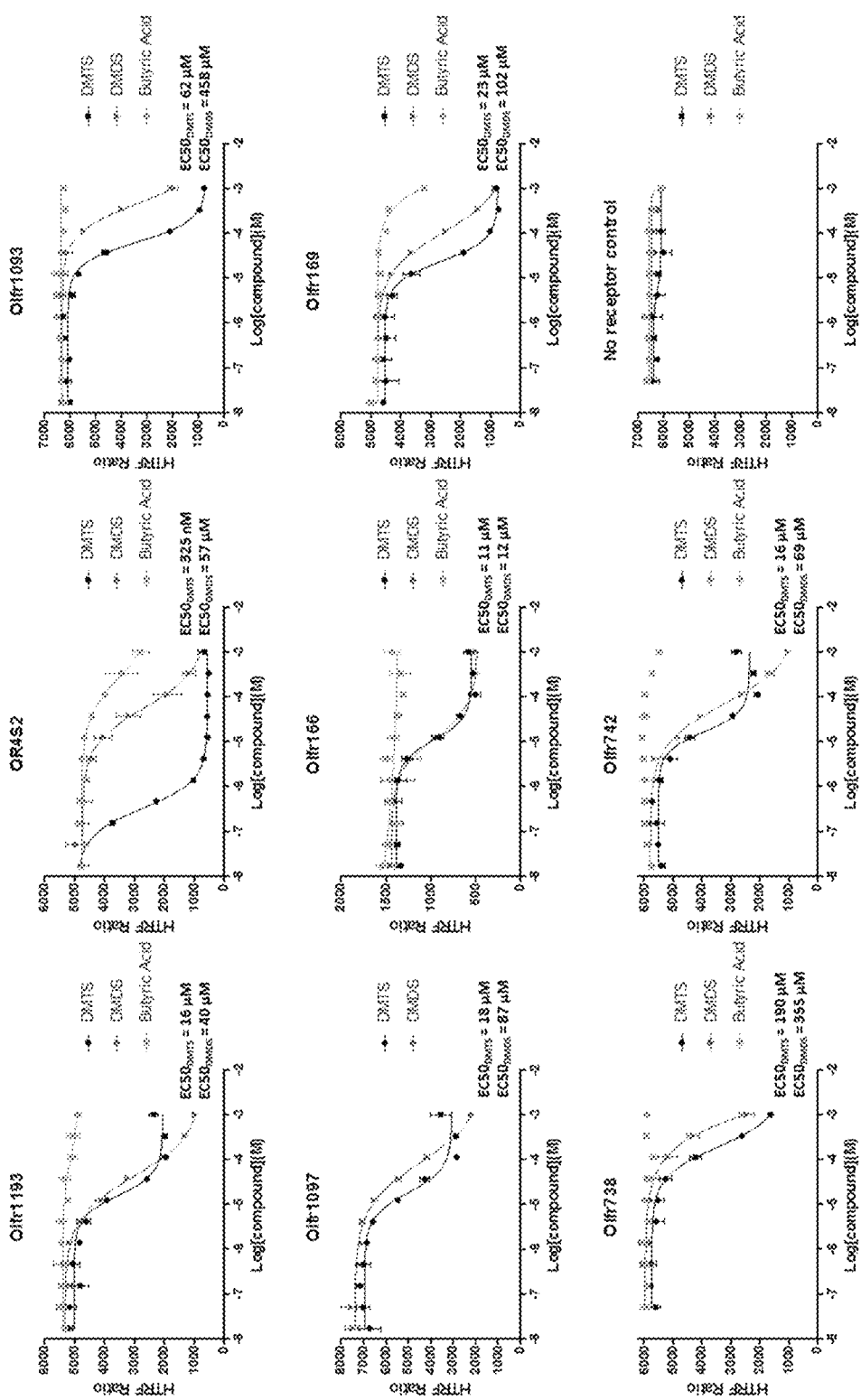
FIG. 5 shows DMTS and DMDS dose response curves of mouse odorant receptors Olfr1193, Olfr1093, Olfr1097, Olfr166, Olfr169, Olfr738, Olfr742 and of human odorant receptor OR4S2.

In FIG. 4, the length of the bars indicate the potency of activity inhibition (IC50, expressed in negative log molar concentration) of the select compounds for each receptor. The absence of a bar indicates absence of inhibition for the corresponding receptor compound pair. These compounds can specifically bind and block the activity of DMTS or DMDS receptors, and thus may suppress or inhibit the smell of DMTS or DMDS. Such compounds may therefore be used as malodour counteractants for latrine or oral odor control applications.

Example 5

Response Profiles of Mouse and Human DMTS Receptors to DMDS

Functional dose-response experiments were performed to confirm the DMTS activity on the DMTS receptors identified in Example 2 and to further characterize their response to DMDS. Using the same cell-based assay described in Example 2, mouse receptors Olfr1193, Olfr1093, Olfr1097, Olfr166, Olfr169, Olfr738, Olfr742 and of human odorant receptor OR4S2 were tested with increasing concentration of DMTS, DMDS or butyric acid (control). A strong dose-dependent increase of the receptor activity is observed for DMTS and DMDS relative to the butyric acid control compound. A weak response for OR4S2 and Olfr169 to butyric acid was visible but was too weak to consider butyric acid as a representative ligand for these receptors. The activity levels are reported by the potency of DMTS or DMDS induced-response for each receptor as a measure of the EC50 value, $EC50_{DMTS}$ and $EC50_{DMDS}$ respectively. A mock transfection control experiment in which the cells do not express the odorant receptors did not show activity upon DMTS or DMDS exposure. Competitive antagonists at the malodor binding site of these receptors have the potential to reduce the unpleasant perception of both DMTS and DMDS.

The invention claimed is:

1. A method for identifying a compound that binds, suppresses, blocks, inhibits, and/or modulates the activity of an olfactory receptor that is activated by a malodor-causing substance comprising:
   a. contacting a test substance and a malodor-causing substance to at least one olfactory receptor that is activated by DMTS or DMDS selected from the group consisting of Olfr1097, and OR8H3;
   b. measuring the response of the olfactory receptor to the malodor-causing substance by measuring the response of the olfactory receptor in the presence and absence of the test sub stance;
   c. identifying a test substance that modulates the response of the olfactory receptor on the basis of an increase or decrease of the response that was measured in the presence and of the test substance relative to the response that was measured in the absence of the test substance; and
   d. selecting the identified test substance as a compound that modulates the response of the olfactory receptor to the malodor-causing substance, wherein the malodor-causing substance is dimethyl trisulfide (DMTS) or dimethyl disulfide (DMDS).

2. A method for identifying a malodor inhibitor comprising:
   a. contacting a test substance and a malodor-causing substance to at least one olfactory receptor, wherein the receptor is activated by dimethyl trisulfide (DMTS) or dimethyl disulfide (DMDS) and comprises a polypeptide comprising an amino acid sequence having 100% sequence identity to SEQ ID NO: 6 or SEQ ID NO: 34;

b. measuring the response of the olfactory receptor polypeptide to the malodor-causing substance;

c. identifying, based on a decrease in the measured olfactory receptor response, a test substance that suppresses the response of the olfactory receptor; and d. selecting, as a malodor inhibitor, the test substance that suppresses the response of the olfactory receptor, wherein the malodor-causing substance is DMTS or DMDS.

3. A method for identifying a compound that binds, suppresses, blocks, inhibits, and/or modulates the activity of at least one olfactory receptor that is activated by a malodor-causing substance, the method comprising:

a. contacting the receptor, or a chimera or fragment thereof with a compound; and b. determining whether the compound increases or decreases the activity of the receptor;

wherein the receptor is activated by DMTS or DMDS and is a polypeptide i) comprising an amino acid sequence having 100% sequence identity to SEQ ID NO: 6 or SEQ ID NO: 34; or ii) encoded by a nucleic acid molecule comprising a nucleic acid sequence having 100% sequence identity to SEQ ID NO: 5 or SEQ ID NO: 33, or the reverse complement thereof;

wherein the malodor-causing substance is dimethyl trisulfide (DMTS) or dimethyl disulfide (DMDS).

4. A method of identifying a compound that modulates dimethyl trisulfide (DMTS) or dimethyl disulfide (DMDS) associated malodor comprising: (i) contacting a cell line that expresses a DMTS or DMDS receptor polypeptide with at least one compound; (ii) screening for compounds that bind, suppress, block, inhibit, and/or modulate the activity of said olfactory receptor polypeptide; and (iii) identifying a compound that modulates DMTS or DMDS associated malodor if it binds, suppresses, blocks, inhibits, and/or modulates the activity of said DMTS or DMDS receptor polypeptide, wherein the receptor polypeptide is activated by DMTS or DMDS and a. comprises an amino acid sequence having 100% sequence identity to SEQ ID NO: 6 or SEQ ID NO: 34; or b. is encoded by a nucleic acid molecule comprising a nucleic acid sequence having 100% sequence identity to SEQ ID NO: 5 or SEQ ID NO: 33, or the reverse complement thereof.

5. A method for identifying a malodor modulating compound, the method comprising:

a. contacting a polypeptide that is activated by dimethyl trisulfide (DMTS) or dimethyl disulfide (DMDS) with a compound;

b. determining whether the compound has an effect on the activity of the polypeptide; and c. identifying, based on the compound's increasing or decreasing the activity of the polypeptide, the compound as a malodor modulating compound, wherein the polypeptide comprises an amino acid sequence having 100% sequence identity to SEQ ID NO: 6 or SEQ ID NO: 34.

* * * * *

SEQUENCE LISTING

```
<160> NUMBER OF SEQ ID NOS: 55

<210> SEQ ID NO 1
<211> LENGTH: 957
<212> TYPE: DNA
<213> ORGANISM: Mus musculus

<400> SEQUENCE: 1
atggcctcaa ggacttattc catggaagaa gtaaataatg tcactgaatt cattttcttg     60
ggtctttctc agaaccctga ggttgaaaaa gtgtgctttg tggtgttctc cttctttac    120 atggtcattc tgctaggaaa cctcctcatc atgttgacag tttgcagtgg caatcttttc    180
aagtttccca tgtatttttt cctcaacttt ctgtcttttg tggacatttg ctactcctca    240
gtcacagcac ccaagatgat tattgacctg ttagtgaaga aaaagactat atcctatgtg    300
```

```
gggtgcatgt tacaactctt tgtggttcat ttctttggtt gcactgagat cttcattctt    360
actgtcatgg cctatgatag atatgtggcc atttgtaaac ctctccacta tatgactatg    420
atggaccggg aaagatgcaa taagatgttg ctcggaacat ggatcggtgg cttcttacat    480
tctattatcc aagtggctct tgtggtccag ctcccctttt gtggaccgaa tgagattgat    540
cactatttct gtgatgtaca tcctgtactg aaacttgcct gcactgacac ttacattgtt    600 ggtattttg tgacagcaaa cagtggcacc attgcattgg aagttttgt catcttgctg      660 atctcataca cagtcattct catgtctctg agaaagcagt catctgaagg cagacgcaaa    720
gctctctcca cttgtggatc ccacattgct gttgtcatca ttttttttgg ccctgtact    780 tttatgtata tgcggcctga cactaccttc tctgaggaca agatggtagc tatattttac    840
accattatca ctcccatgct gaatcctcta atttacactc taagaaatgc agaagtaaag    900
aatgcaatga gaaaactgtg ggctagaaag ttttcctggg aaactactgg gaaatag      957
```

<210> SEQ ID NO 2
<211> LENGTH: 318
<212> TYPE: PRT
<213> ORGANISM: Mus musculus

<400> SEQUENCE: 2

```
Met Ala Ser Arg Thr Tyr Ser Met Glu Glu Val Asn Asn Val Thr Glu
1               5                  10                  15

Phe Ile Phe Leu Gly Leu Ser Gln Asn Pro Glu Val Glu Lys Val Cys
            20                  25                  30

Phe Val Val Phe Ser Phe Phe Tyr Met Val Ile Leu Leu Gly Asn Leu
        35                  40                  45

Leu Ile Met Leu Thr Val Cys Ser Gly Asn Leu Phe Lys Phe Pro Met
    50                  55                  60

Tyr Phe Phe Leu Asn Phe Leu Ser Phe Val Asp Ile Cys Tyr Ser Ser
65                  70                  75                  80

Val Thr Ala Pro Lys Met Ile Ile Asp Leu Leu Val Lys Lys Lys Thr
                85                  90                  95

Ile Ser Tyr Val Gly Cys Met Leu Gln Leu Phe Val Val His Phe Phe
            100                 105                 110

Gly Cys Thr Glu Ile Phe Ile Leu Thr Val Met Ala Tyr Asp Arg Tyr
        115                 120                 125

Val Ala Ile Cys Lys Pro Leu His Tyr Met Thr Met Met Asp Arg Glu
    130                 135                 140

Arg Cys Asn Lys Met Leu Leu Gly Thr Trp Ile Gly Gly Phe Leu His
145                 150                 155                 160

Ser Ile Ile Gln Val Ala Leu Val Val Gln Leu Pro Phe Cys Gly Pro
                165                 170                 175

Asn Glu Ile Asp His Tyr Phe Cys Asp Val His Pro Val Leu Lys Leu
            180                 185                 190

Ala Cys Thr Asp Thr Tyr Ile Val Gly Ile Phe Val Thr Ala Asn Ser
        195                 200                 205

Gly Thr Ile Ala Leu Gly Ser Phe Val Ile Leu Ile Ser Tyr Thr
    210                 215                 220

Val Ile Leu Met Ser Leu Arg Lys Gln Ser Glu Gly Arg Arg Lys
225                 230                 235                 240

Ala Leu Ser Thr Cys Gly Ser His Ile Ala Val Val Ile Ile Phe Phe
                245                 250                 255

Gly Pro Cys Thr Phe Met Tyr Met Arg Pro Asp Thr Thr Phe Ser Glu
```

```
                    260                 265                 270
Asp Lys Met Val Ala Ile Phe Tyr Thr Ile Ile Thr Pro Met Leu Asn
            275                 280                 285

Pro Leu Ile Tyr Thr Leu Arg Asn Ala Glu Val Lys Asn Ala Met Arg
        290                 295                 300

Lys Leu Trp Ala Arg Lys Phe Ser Trp Glu Thr Thr Gly Lys
305                 310                 315
```

```
<210> SEQ ID NO 3
<211> LENGTH: 969
<212> TYPE: DNA
<213> ORGANISM: Mus musculus

<400> SEQUENCE: 3
atggaaaaga tcacatcagc tgtggatgtc cacaatattc cattaaagaa catgactgaa    60
gccaccatgt ttattctctt aggattcaca gatgactttg aactccaagt cttcctgttt   120
ttactgtttc ttgctattta tctcttcact ctggtaggaa actttggact ggttgttttg   180
gtcattgggg attgtcggct acacaacccc atgtactatt tcctaagtgt tttgtctttc   240
ctggatgctt gctattctac agttgttaca cccaaaatgt tggtcaactt ctaagtgaa    300
aataagtcca tttcattcct tgcatgtgca acccaaaatgc ttctctttgt tcgttggga   360
accacagaat gctttctcct ggcagcaatg gcttatgacc gatatgtagc catctacaac   420
ccacttctgt atacagtggc catgtcaccc agagtatacc tgccactcat cattgcttcc   480
tatgctggtg gagttgtgca tggtgctatc cacacagtgg ccactttcag tctgtccttc   540
tgtggatcca atgaaattaa gcatgtcttc tgtgacatcc ctgcattgct tgctctttct   600
tgttctgata cccacacaaa tgagcttcta gtcttgtact tggtgggctt gattgagatt   660
gttaccatcc tgattgttct ggtctcctat ggattcatcc tctttgccat tctgaacatg   720
cattctgctg agggtaggag gaaagtgttc tctacatgtg gctctcacct cactggagtc   780
tctatttacc atggtacaat ccttttcact tatatgaggc ctagttccag ttatgcttca   840
aatcatgaca tggtagtgtc aatattttac accattgtga tacccatgtt gaatcctatc   900
atctatagtt tgaggaacaa agatgtaaaa gtagcattta ataaattgtg agaaaatgt    960
gattcataa                                                           969
```

```
<210> SEQ ID NO 4
<211> LENGTH: 322
<212> TYPE: PRT
<213> ORGANISM: Mus musculus

<400> SEQUENCE: 4

Met Glu Lys Ile Thr Ser Ala Val Asp Val His Asn Ile Pro Leu Lys
1               5                   10                  15

Asn Met Thr Glu Ala Thr Met Phe Ile Leu Leu Gly Phe Thr Asp Asp
            20                  25                  30

Phe Glu Leu Gln Val Phe Leu Phe Leu Phe Leu Ala Ile Tyr Leu
        35                  40                  45

Phe Thr Leu Val Gly Asn Phe Gly Leu Val Val Leu Ile Gly Asp
    50                  55                  60

Cys Arg Leu His Asn Pro Met Tyr Tyr Phe Leu Ser Val Leu Ser Phe
65                  70                  75                  80

Leu Asp Ala Cys Tyr Ser Thr Val Val Thr Pro Lys Met Leu Val Asn
                85                  90                  95
```

```
Phe Leu Ser Glu Asn Lys Ser Ile Ser Phe Leu Ala Cys Ala Thr Gln
                100                 105                 110
Met Leu Leu Phe Val Ser Leu Gly Thr Thr Glu Cys Phe Leu Leu Ala
            115                 120                 125
Ala Met Ala Tyr Asp Arg Tyr Val Ala Ile Tyr Asn Pro Leu Leu Tyr
130                 135                 140
Thr Val Ala Met Ser Pro Arg Val Tyr Leu Pro Leu Ile Ile Ala Ser
145                 150                 155                 160
Tyr Ala Gly Gly Val His Gly Ala Ile His Thr Val Ala Thr Phe
                165                 170                 175
Ser Leu Ser Phe Cys Gly Ser Asn Glu Ile Lys His Val Phe Cys Asp
            180                 185                 190
Ile Pro Ala Leu Leu Ala Leu Ser Cys Ser Asp Thr His Thr Asn Glu
            195                 200                 205
Leu Leu Val Leu Tyr Leu Val Gly Leu Ile Glu Ile Val Thr Ile Leu
        210                 215                 220
Ile Val Leu Val Ser Tyr Gly Phe Ile Leu Phe Ala Ile Leu Asn Met
225                 230                 235                 240
His Ser Ala Glu Gly Arg Arg Lys Val Phe Ser Thr Cys Gly Ser His
                245                 250                 255
Leu Thr Gly Val Ser Ile Tyr His Gly Thr Ile Leu Phe Thr Tyr Met
            260                 265                 270
Arg Pro Ser Ser Ser Tyr Ala Ser Asn His Asp Met Val Val Ser Ile
                275                 280                 285
Phe Tyr Thr Ile Val Ile Pro Met Leu Asn Pro Ile Ile Tyr Ser Leu
            290                 295                 300
Arg Asn Lys Asp Val Lys Val Ala Phe Asn Lys Leu Trp Arg Lys Cys
305                 310                 315                 320
Asp Ser

<210> SEQ ID NO 5
<211> LENGTH: 948
<212> TYPE: DNA
<213> ORGANISM: Mus musculus

<400> SEQUENCE: 5
atgagtgcct gtaatcatac aaatgaacct gagttcacgc ttgtgggact gacagactcc     60
aaggagattc agctggtcct ctctgttttg tttctcctga tatacatgct cactgtcttg    120
ggaaacatag gtatgatact gatcattcat ctagatgtcc agctccacac tccaatgtat    180
ttttcctca cccacttgtc attccttgac ctcagttact caactgtaat cacacctaaa    240
accttacaga atacgctgac ctccataaaa aatatttcct tcatgggatg cttcacccag    300
ttgtatttct ttgtcctctt ggcagcttct gaatgtttta ctttcgtc aatggcctat    360
gaccgctatg tagctatctg caaccctcta cactatccag ttattatgtc cctaggcgc    420
tcatatactc tcatcactgt gtcctacatg attggagttt ggattcttc tgtcactgtc    480
ttttgcttaa gcacactgga tttctgcaac tccaaagtaa ttcatcactt cttttgtgac    540
acattcccaa tttagctct gtcctgcagt gataccctat atgcagaagc cactatattc    600
gttttagctg gttccactct attgctgtcg ctcatcacga tatcctcatc ctatgtatct    660
attctctcta caattttgaa gataaattct tcttcaggaa agcacaaagc cttctctaca    720
tgtgcctcac atcttatagg agtcactgtt tttatggta caatgatctt tacttattta    780
aaaccaagta cgtcctactc cctgggaaag gatcaagtag cctctgtttt ttatactata    840
```

```
gtgattccca tgctgaaccc acttatctat agtctcagga acaaagaagt gaaaagtgct      900
gttgttagag ttatgaagaa gagagagtgc atccagaaac tagaataa                   948
```

<210> SEQ ID NO 6
<211> LENGTH: 315
<212> TYPE: PRT
<213> ORGANISM: Mus musculus

<400> SEQUENCE: 6

```
Met Ser Ala Cys Asn His Thr Asn Glu Pro Glu Phe Thr Leu Val Gly
1               5                   10                  15

Leu Thr Asp Ser Lys Glu Ile Gln Leu Val Leu Ser Val Leu Phe Leu
            20                  25                  30

Leu Ile Tyr Met Leu Thr Val Leu Gly Asn Ile Gly Met Ile Leu Ile
        35                  40                  45

Ile His Leu Asp Val Gln Leu His Thr Pro Met Tyr Phe Phe Leu Thr
50                  55                  60

His Leu Ser Phe Leu Asp Leu Ser Tyr Ser Thr Val Ile Thr Pro Lys
65                  70                  75                  80

Thr Leu Gln Asn Thr Leu Thr Ser Ile Lys Asn Ile Ser Phe Met Gly
                85                  90                  95

Cys Phe Thr Gln Leu Tyr Phe Phe Val Leu Leu Ala Ala Ser Glu Cys
            100                 105                 110

Phe Ile Leu Ser Ser Met Ala Tyr Asp Arg Tyr Val Ala Ile Cys Asn
        115                 120                 125

Pro Leu His Tyr Pro Val Ile Met Ser Pro Arg Arg Ser Tyr Thr Leu
130                 135                 140

Ile Thr Val Ser Tyr Met Ile Gly Val Leu Asp Ser Ser Val Thr Val
145                 150                 155                 160

Phe Cys Leu Ser Thr Leu Asp Phe Cys Asn Ser Lys Val Ile His His
                165                 170                 175

Phe Phe Cys Asp Thr Phe Pro Ile Leu Ala Leu Ser Cys Ser Asp Thr
            180                 185                 190

Tyr Asn Ala Glu Ala Thr Ile Phe Val Leu Ala Gly Ser Thr Leu Leu
        195                 200                 205

Leu Ser Leu Ile Thr Ile Ser Ser Ser Tyr Val Ser Ile Leu Ser Thr
210                 215                 220

Ile Leu Lys Ile Asn Ser Ser Ser Gly Lys His Lys Ala Phe Ser Thr
225                 230                 235                 240

Cys Ala Ser His Leu Ile Gly Val Thr Val Phe Tyr Gly Thr Met Ile
                245                 250                 255

Phe Thr Tyr Leu Lys Pro Ser Thr Ser Tyr Ser Leu Gly Lys Asp Gln
            260                 265                 270

Val Ala Ser Val Phe Tyr Thr Ile Val Pro Met Leu Asn Pro Leu
        275                 280                 285

Ile Tyr Ser Leu Arg Asn Lys Glu Val Lys Ser Ala Val Val Arg Val
290                 295                 300

Met Lys Lys Arg Glu Cys Ile Gln Lys Leu Glu
305                 310                 315
```

<210> SEQ ID NO 7
<211> LENGTH: 939
<212> TYPE: DNA
<213> ORGANISM: Mus musculus

<400> SEQUENCE: 7

```
atggagaaat ggaatcagag ctcaagtgat tttactctgt taggactgct tccacaaaac    60
caaacaggcc tgctactttt gatgctcatc atctttgtct tctctctggc tttgtgtggc   120
aactcaggaa tgatccacct cattcgtgtg gatccaaggc tccacacccc catgtacttt   180
ctcctcagtc agctctctct catggacctg atgtacattt ctaccactgt tcccaagatg   240
gcatttaact tcctttctgg ccagaaaagc atctctttc tgggctgtgg agtgcaatcc    300
ttcttcttcc tgactatggc atgttctgag ggcttgctct ggcttccat ggcttatgat    360
cgttttgtgg ctatctgcca tcccttcac tatcccattc gcatgagcaa aataatgtgt    420
ctgaagatga tcataggatc ctggatattg ggctcaatca actctttagc acataccgtc   480
tatgccttc atattcctta ctgccattct aggtccatta accatttctt ctgtgatgtt    540
ccagccatgt tgcccctggc ctgtatggac acttgggttt atgagtacat ggtgtttgtg    600
agcacaagcc tgtttctcct actgcctttc cttggtatca cagcttccta tggtcgggtc   660
cttttgctg tcttccacat gcgctcaaaa gagggaaaga agaaggcctt caccacatgc    720
tcaactcact taactgtggt gacattttac tatgcacctt ttgtctatac ctatcttcga    780
cctaggagtc ttcgctcccc aacagaagat aagattctgg ctgttttcta cactatcctt   840
accccccatgc tcaaccccat catttatagt ctgaggaata aggaggtcct ggggggccatg   900
acaagagtcc ttggtacttt tccttcaact aaaccgtaa                            939
```

<210> SEQ ID NO 8
<211> LENGTH: 312
<212> TYPE: PRT
<213> ORGANISM: Mus musculus

<400> SEQUENCE: 8

```
Met Glu Lys Trp Asn Gln Ser Ser Asp Phe Thr Leu Leu Gly Leu
1               5                   10                  15

Leu Pro Gln Asn Gln Thr Gly Leu Leu Leu Met Leu Ile Ile Phe
                20                  25                  30

Val Phe Ser Leu Ala Leu Cys Gly Asn Ser Gly Met Ile His Leu Ile
            35                  40                  45

Arg Val Asp Pro Arg Leu His Thr Pro Met Tyr Phe Leu Leu Ser Gln
        50                  55                  60

Leu Ser Leu Met Asp Leu Met Tyr Ile Ser Thr Thr Val Pro Lys Met
65                  70                  75                  80

Ala Phe Asn Phe Leu Ser Gly Gln Lys Ser Ile Ser Phe Leu Gly Cys
                85                  90                  95

Gly Val Gln Ser Phe Phe Phe Leu Thr Met Ala Cys Ser Glu Gly Leu
            100                 105                 110

Leu Leu Ala Ser Met Ala Tyr Asp Arg Phe Val Ala Ile Cys His Pro
        115                 120                 125

Leu His Tyr Pro Ile Arg Met Ser Lys Ile Met Cys Leu Lys Met Ile
    130                 135                 140

Ile Gly Ser Trp Ile Leu Gly Ser Ile Asn Ser Leu Ala His Thr Val
145                 150                 155                 160

Tyr Ala Leu His Ile Pro Tyr Cys His Ser Arg Ser Ile Asn His Phe
                165                 170                 175

Phe Cys Asp Val Pro Ala Met Leu Pro Leu Ala Cys Met Asp Thr Trp
            180                 185                 190

Val Tyr Glu Tyr Met Val Phe Val Ser Thr Ser Leu Phe Leu Leu Leu
```

```
            195                 200                 205
Pro Phe Leu Gly Ile Thr Ala Ser Tyr Gly Arg Val Leu Phe Ala Val
    210                 215                 220

Phe His Met Arg Ser Lys Glu Gly Lys Lys Ala Phe Thr Thr Cys
225                 230                 235                 240

Ser Thr His Leu Thr Val Val Thr Phe Tyr Ala Pro Phe Val Tyr
                245                 250                 255

Thr Tyr Leu Arg Pro Arg Ser Leu Arg Ser Pro Thr Glu Asp Lys Ile
            260                 265                 270

Leu Ala Val Phe Tyr Thr Ile Leu Thr Pro Met Leu Asn Pro Ile Ile
                275                 280                 285

Tyr Ser Leu Arg Asn Lys Glu Val Leu Gly Ala Met Thr Arg Val Leu
    290                 295                 300

Gly Thr Phe Pro Ser Thr Lys Pro
305                 310

<210> SEQ ID NO 9
<211> LENGTH: 942
<212> TYPE: DNA
<213> ORGANISM: Mus musculus

<400> SEQUENCE: 9
atggaatatg agaactacac ttttaacagc gacttcatcc tcttgggact gttctcttct      60
tcaaagacaa gcttaacttt ttctcattt atatttttca tttttattat ggctataaca     120
gaaaatgccc tcatgatcct cctaatccac agggattctc gactccatac cccaatgtat     180
ttcctgctta gtcatctctc cttcatggat atcttgcaca tttccaacat tgttcctaaa     240
atgattgctg acttcctctc aggcagcaga actatttcct tgcaggctg tgccttccag     300 atatttctct ctcttacctt gctaggtggt gagtgccttc cctggcagc catgtcctat     360 gatcgatatg tggccatctg ccacccactt cgctaccctg tgctgatgag ggataactcc     420
agtaggctcc tggctgcagg ctcctggctg gtggggatcc tcaactccat agtacacaca     480
gtttttgcac tccactttcc cttctgccac tcaagagcca ttgatcactt tttctgcgaa     540
gtccctgcca tgttgaaatt gtcatgtata gacacaacac actatgaacg aggcgtttat     600
gtgagtggca ttatttttct gctgatccca ttttccatga tctctatatc ttatgtgcaa     660
attctcctca ctgtattcca aatgcagtca tcaggggccc ggcaaaagtc cttttccacc     720
tgttccttcc acatggttgt tgtcataatg tactatgggc cattcatttt tacatatatg     780
agacctcgct cataccacac tccagggcag gataaatttt tggcaatatt ctacaccatc     840
ctgacaccca cactcaaccc cataatctac agctttcgta taaagatgt ccttatggct     900 gtgaaaaaca tcgtccaaag taattttttg aataaaaaat ga                        942

<210> SEQ ID NO 10
<211> LENGTH: 313
<212> TYPE: PRT
<213> ORGANISM: Mus musculus

<400> SEQUENCE: 10

Met Glu Tyr Glu Asn Tyr Thr Phe Asn Ser Asp Phe Ile Leu Leu Gly
1               5                   10                  15

Leu Phe Ser Ser Ser Lys Thr Ser Leu Thr Phe Phe Ser Phe Ile Phe
                20                  25                  30

Phe Ile Phe Ile Met Ala Ile Thr Glu Asn Ala Leu Met Ile Leu Leu
            35                  40                  45
```

Ile His Arg Asp Ser Arg Leu His Thr Pro Met Tyr Phe Leu Leu Ser
   50                  55                  60

His Leu Ser Phe Met Asp Ile Leu His Ile Ser Asn Ile Val Pro Lys
 65                  70                  75                  80

Met Ile Ala Asp Phe Leu Ser Gly Ser Arg Thr Ile Ser Phe Ala Gly
                 85                  90                  95

Cys Ala Phe Gln Ile Phe Leu Ser Leu Thr Leu Leu Gly Gly Glu Cys
                100                 105                 110

Leu Leu Leu Ala Ala Met Ser Tyr Asp Arg Tyr Val Ala Ile Cys His
            115                 120                 125

Pro Leu Arg Tyr Pro Val Leu Met Arg Asp Asn Ser Ser Arg Leu Leu
        130                 135                 140

Ala Ala Gly Ser Trp Leu Val Gly Ile Leu Asn Ser Ile Val His Thr
145                 150                 155                 160

Val Phe Ala Leu His Phe Pro Phe Cys His Ser Arg Ala Ile Asp His
                165                 170                 175

Phe Phe Cys Glu Val Pro Ala Met Leu Lys Leu Ser Cys Ile Asp Thr
            180                 185                 190

Thr His Tyr Glu Arg Gly Val Tyr Val Ser Gly Ile Ile Phe Leu Leu
        195                 200                 205

Ile Pro Phe Ser Met Ile Ser Ile Ser Tyr Val Gln Ile Leu Leu Thr
    210                 215                 220

Val Phe Gln Met Gln Ser Ser Gly Ala Arg Gln Lys Ser Phe Ser Thr
225                 230                 235                 240

Cys Ser Phe His Met Val Val Ile Met Tyr Tyr Gly Pro Phe Ile
                245                 250                 255

Phe Thr Tyr Met Arg Pro Arg Ser Tyr His Thr Pro Gly Gln Asp Lys
            260                 265                 270

Phe Leu Ala Ile Phe Tyr Thr Ile Leu Thr Pro Thr Leu Asn Pro Ile
        275                 280                 285

Ile Tyr Ser Phe Arg Asn Lys Asp Val Leu Met Ala Val Lys Asn Ile
    290                 295                 300

Val Gln Ser Asn Phe Leu Asn Lys Lys
305                 310

<210> SEQ ID NO 11
<211> LENGTH: 936
<212> TYPE: DNA
<213> ORGANISM: Mus musculus

<400> SEQUENCE: 11
atgaaagcct ttagcagccc cagcaactcc agcatcatca ctggcttcat cctcctgggc      60
ttcccctgcc ccaaggaggg gcaaatcctc ctctttgtgc tcttcttcat tatctacatc     120
cttaccctca tgggcaatgc ttccatcata tgtgctgtgt gctatgataa gaaacttcac     180
agccccatgt acctcctgct ggccaacttc tccttcctag aaatctggta tgtcacctcc     240
acagtcccca catgttggc caacttcctc tctgacacga aggtcatctc tttctctgga     300
tgcttcctgc agttctattt cttcttctcc ttgggttcta cagaatgctt tttcctggca     360
gtcatggcat ttgatcgata ccttgccatc tgcagacctc tacattatcc ttctctcatg     420
actgggcgcc tctgcaacat ccttgtgatc agttgctggg tgcttggttt cctctggttc     480
cctgttccca tcatcatcat ctcccaaatg tccttctgtg atccagaat tatagaccac     540 ttcctgtgtg acccaggccc tctgttggcc ctcacctgtg tgagaaattc tttaattgag     600

```
atgactagct ctactttaag ttccctgctt ttatttgttc cattttttt tatcatgggg      660 tcttatgctc tagtaatgag ggctgtgctc agggtcccct cagcagctgg acgaagaaag      720
gccttctcca cctgtgggtc acacttgact gtggtttctc ttttctatgg ctcagtgatg      780
gtcatgtatg tgagcccaac atctgaacat gcagctggag tgcaaaaact tgtgactctg      840
ttttattctg tggttactcc cctccttaat cctgtgatat acagtctgag gaacagagat      900
atgaaacatg caatgaaaaa gttactgaaa atgtaa                                936
```

<210> SEQ ID NO 12
<211> LENGTH: 311
<212> TYPE: PRT
<213> ORGANISM: Mus musculus
<400> SEQUENCE: 12

```
Met Lys Ala Phe Ser Ser Pro Ser Asn Ser Ile Ile Thr Gly Phe
1               5                   10                  15

Ile Leu Leu Gly Phe Pro Cys Pro Lys Glu Gly Gln Ile Leu Phe
                20                  25                  30

Val Leu Phe Phe Ile Ile Tyr Ile Leu Thr Leu Met Gly Asn Ala Ser
            35                  40                      45

Ile Ile Cys Ala Val Cys Tyr Asp Lys Lys Leu His Ser Pro Met Tyr
50                  55                  60

Leu Leu Leu Ala Asn Phe Ser Phe Leu Glu Ile Trp Tyr Val Thr Ser
65                  70                  75                  80

Thr Val Pro Asn Met Leu Ala Asn Phe Leu Ser Asp Thr Lys Val Ile
                85                  90                  95

Ser Phe Ser Gly Cys Phe Leu Gln Phe Tyr Phe Phe Ser Leu Gly
                100                 105                 110

Ser Thr Glu Cys Phe Phe Leu Ala Val Met Ala Phe Asp Arg Tyr Leu
            115                 120                 125

Ala Ile Cys Arg Pro Leu His Tyr Pro Ser Leu Met Thr Gly Arg Leu
            130                 135                 140

Cys Asn Ile Leu Val Ile Ser Cys Trp Val Leu Gly Phe Leu Trp Phe
145                 150                 155                 160

Pro Val Pro Ile Ile Ile Ser Gln Met Ser Phe Cys Gly Ser Arg
                165                 170                 175

Ile Ile Asp His Phe Leu Cys Asp Pro Gly Pro Leu Leu Ala Leu Thr
                180                 185                 190

Cys Val Arg Asn Ser Leu Ile Glu Met Thr Ser Ser Thr Leu Ser Ser
            195                 200                 205

Leu Leu Leu Phe Val Pro Phe Phe Ile Met Gly Ser Tyr Ala Leu
210                 215                 220

Val Met Arg Ala Val Leu Arg Val Pro Ser Ala Ala Gly Arg Arg Lys
225                 230                 235                 240

Ala Phe Ser Thr Cys Gly Ser His Leu Thr Val Val Ser Leu Phe Tyr
                245                 250                 255

Gly Ser Val Met Val Met Tyr Val Ser Pro Thr Ser Glu His Ala Ala
            260                 265                 270

Gly Val Gln Lys Leu Val Thr Leu Phe Tyr Ser Val Val Thr Pro Leu
            275                 280                 285

Leu Asn Pro Val Ile Tyr Ser Leu Arg Asn Arg Asp Met Lys His Ala
290                 295                 300

Met Lys Lys Leu Leu Lys Met
```

<210> SEQ ID NO 13
<211> LENGTH: 936
<212> TYPE: DNA
<213> ORGANISM: Mus musculus

<400> SEQUENCE: 13

```
atgaaaaccc tcagcagccc agcaactcc agcaccatca ctggcttcat cctcttgggc      60
ttcccctgcc ccagggaggg gcaaatcctc ctctttgtga ccttcttcat tgtttacata    120
ctcattctta tgggcaatgc ttccatcatc tgtgctgtgt actgtgatca gagcctccac    180
accccatgt acttcctgct ggccaacttc tccttcctgg gatctggta tgtcacctcc      240
acagtcccca acatgttggc caacttcctt cagacacca aggtcatctc tttctctgga    300
tgcttcctgc agttctattt cttcttctcc tttggttcta cagaatgctt tttcctggca    360
gtcatggcat ttgatcgata ccttgccatc tgtaggccac tacattatcc ttctctcatg    420
actgggcacc tctgcaacat ccttgtgatc agttgctggg tgcttggttt cctctggttc    480
cctgtaccca tcatcatcat ctcccagatg tccttctgtg ggtccagaat tatagaccac    540
ttcctgtgtg acccaggccc tcttttggcc cttgcctgtt ccagagcccc attgatggag    600
gtttctgga caattataat gtctatgctc ctggttattc ctttcctctt catcatggga    660
acttacatat tggtcctaag agctgtgttt agacttcctt caagagatgg acaaaaaaag    720
gccttctcca cttgcgggtc tcatctcaca gtagtttcac tctttttattg ctcagtgatg    780
aaaatgtatt tgagcccaac atctgagcat gaagctggaa tgcagaagct tgtaactcta    840
ttttattctg tgggtactcc actacttaat cctgtgatat acagtctgag gaacaaagat    900
atgaaaaatg ccctgcagaa gattttaaga acataa                              936
```

<210> SEQ ID NO 14
<211> LENGTH: 311
<212> TYPE: PRT
<213> ORGANISM: Mus musculus

<400> SEQUENCE: 14

```
Met Lys Thr Leu Ser Ser Pro Ser Asn Ser Ser Thr Ile Thr Gly Phe
1               5                   10                  15

Ile Leu Leu Gly Phe Pro Cys Pro Arg Glu Gly Gln Ile Leu Leu Phe
            20                  25                  30

Val Thr Phe Phe Ile Val Tyr Ile Leu Ile Leu Met Gly Asn Ala Ser
        35                  40                  45

Ile Ile Cys Ala Val Tyr Cys Asp Gln Ser Leu His Thr Pro Met Tyr
    50                  55                  60

Phe Leu Leu Ala Asn Phe Ser Phe Leu Glu Ile Trp Tyr Val Thr Ser
65                  70                  75                  80

Thr Val Pro Asn Met Leu Ala Asn Phe Leu Ser Asp Thr Lys Val Ile
                85                  90                  95

Ser Phe Ser Gly Cys Phe Leu Gln Phe Tyr Phe Phe Ser Phe Gly
            100                 105                 110

Ser Thr Glu Cys Phe Phe Leu Ala Val Met Ala Phe Asp Arg Tyr Leu
        115                 120                 125

Ala Ile Cys Arg Pro Leu His Tyr Pro Ser Leu Met Thr Gly His Leu
    130                 135                 140

Cys Asn Ile Leu Val Ile Ser Cys Trp Val Leu Gly Phe Leu Trp Phe
145                 150                 155                 160
```

```
Pro Val Pro Ile Ile Ile Ser Gln Met Ser Phe Cys Gly Ser Arg
                165                 170                 175

Ile Ile Asp His Phe Leu Cys Asp Pro Gly Pro Leu Leu Ala Leu Ala
            180                 185                 190

Cys Ser Arg Ala Pro Leu Met Glu Val Phe Trp Thr Ile Ile Met Ser
        195                 200                 205

Met Leu Leu Val Ile Pro Phe Leu Phe Ile Met Gly Thr Tyr Ile Leu
    210                 215                 220

Val Leu Arg Ala Val Phe Arg Leu Pro Ser Arg Asp Gly Gln Lys Lys
225                 230                 235                 240

Ala Phe Ser Thr Cys Gly Ser His Leu Thr Val Val Ser Leu Phe Tyr
                245                 250                 255

Cys Ser Val Met Lys Met Tyr Leu Ser Pro Thr Ser Glu His Glu Ala
            260                 265                 270

Gly Met Gln Lys Leu Val Thr Leu Phe Tyr Ser Val Gly Thr Pro Leu
        275                 280                 285

Leu Asn Pro Val Ile Tyr Ser Leu Arg Asn Lys Asp Met Lys Asn Ala
    290                 295                 300

Leu Gln Lys Ile Leu Arg Thr
305                 310

<210> SEQ ID NO 15
<211> LENGTH: 918
<212> TYPE: DNA
<213> ORGANISM: Mus musculus

<400> SEQUENCE: 15
atggaactga acaggaccca gctgactgaa tttgttctca gaggaataac agatcgttca      60
gagctgcaag tcccctgtt  cctggtgttc tttctcatct atgttatcac catggtgggc     120
aaccttggct taatctttgt catctggaag gaccctcatc ttcacacacc catgtacctt     180
ttccttggaa atttggcctt tgctgatgcc tgtaattcat cctctgtgac accaaagatg     240
cttatgaaat ttttaaataa gaatgacatg atatccatgg gtgagtgttt tgctcaattt     300
tatttctttt gttcaagtgt aactgcagaa gccttcattc tggtagctat ggcctatgac     360
cgctatgtag ccatatgcaa acctctgctc tatgtagtgg tgatgtccaa cagactctgt     420
attcagttca taggtgtatc ctatctaatt ggacttctac atggcttact tcatgtagga     480
ttgttattta ggttaacgtt ttgtagttcc aatgtaatag attatttcta ctgtgacatc     540
ctgccacttt ataggatttc ttgcactgac ccatcgatca atgtactggt agctttcatt     600
atgggtattt tattacaagt gagtaccttt atgagtatta tagtctccta tgtccgtgtc     660
ctctttgcca tcctgagaac aaagtctgag aggggcagaa acaaagcctt ctctacttgc     720
agttcccacc tgtcatctgt gtctttgttc tatggcactc tcttcatcat atatgtcctc     780
tctggctctg acacagataa ttatcagggt aaaatgtatt cactgttcta taccattatc     840
attcctctgc taaacccctt catttacagc ctaagaaata agaagtcat cggtgccttg     900 agaaaagtca gaaaatga                                                   918

<210> SEQ ID NO 16
<211> LENGTH: 305
<212> TYPE: PRT
<213> ORGANISM: Mus musculus

<400> SEQUENCE: 16
```

```
Met Glu Leu Asn Arg Thr Gln Leu Thr Glu Phe Val Leu Arg Gly Ile
1               5                   10                  15

Thr Asp Arg Ser Glu Leu Gln Val Pro Leu Phe Leu Val Phe Phe Leu
            20                  25                  30

Ile Tyr Val Ile Thr Met Val Gly Asn Leu Gly Leu Ile Phe Val Ile
            35                  40                  45

Trp Lys Asp Pro His Leu His Thr Pro Met Tyr Leu Phe Leu Gly Asn
50                  55                  60

Leu Ala Phe Ala Asp Ala Cys Asn Ser Ser Val Thr Pro Lys Met
65                  70                  75                  80

Leu Met Lys Phe Leu Asn Lys Asn Asp Met Ile Ser Met Gly Glu Cys
            85                  90                  95

Phe Ala Gln Phe Tyr Phe Phe Cys Ser Ser Val Thr Ala Glu Ala Phe
            100                 105                 110

Ile Leu Val Ala Met Ala Tyr Asp Arg Tyr Val Ala Ile Cys Lys Pro
            115                 120                 125

Leu Leu Tyr Val Val Met Ser Asn Arg Leu Cys Ile Gln Phe Ile
130                 135                 140

Gly Val Ser Tyr Leu Ile Gly Leu Leu His Gly Leu His Val Gly
145                 150                 155                 160

Leu Leu Phe Arg Leu Thr Phe Cys Ser Ser Asn Val Ile Asp Tyr Phe
            165                 170                 175

Tyr Cys Asp Ile Leu Pro Leu Tyr Arg Ile Ser Cys Thr Asp Pro Ser
            180                 185                 190

Ile Asn Val Leu Val Ala Phe Ile Met Gly Ile Leu Leu Gln Val Ser
            195                 200                 205

Thr Phe Met Ser Ile Ile Val Ser Tyr Val Arg Val Leu Phe Ala Ile
            210                 215                 220

Leu Arg Thr Lys Ser Glu Arg Gly Arg Asn Lys Ala Phe Ser Thr Cys
225                 230                 235                 240

Ser Ser His Leu Ser Ser Val Ser Leu Phe Tyr Gly Thr Leu Phe Ile
            245                 250                 255

Ile Tyr Val Leu Ser Gly Ser Asp Thr Asp Asn Tyr Gln Gly Lys Met
            260                 265                 270

Tyr Ser Leu Phe Tyr Thr Ile Ile Pro Leu Leu Asn Pro Phe Ile
            275                 280                 285

Tyr Ser Leu Arg Asn Lys Glu Val Ile Gly Ala Leu Arg Lys Val Arg
            290                 295                 300

Lys
305

<210> SEQ ID NO 17
<211> LENGTH: 951
<212> TYPE: DNA
<213> ORGANISM: Mus musculus

<400> SEQUENCE: 17
atgcctgggg tcaataccct cagcctgaca ccaagatact ttattctcaa tgggattcct    60
gggttggaag ctgcacacat ctggatctct ctgccattct tcattatgta cctcattgct   120
gtcacaggta actgtggact tatctacctc atcagtcatg aggaggctct gcaccggccc   180
atgtactact tctagccat gttgtctgct acagatattt ctgggtgtaa tacaattgtc   240
cccagtatgt tatgcatctt ttggttcagt gtcaaggaga ttgatttcaa tgcctgcctt   300
gtacagatgt ttttcatcca catgttaaca ggcatggagt ctggtgtgct catgcttatg   360
```

```
gctctcgacc gctatgtggc tatatgctat ccattacgct atactaccat actcaccaac    420
actatgatta ccaagattgg attggcagca cttgttagaa gtgtgttact catggtccct    480
tttgctttcc tgatcaagcg tcttccatac tgtagaggaa acctcatcca acatacctat    540
tgtgatcaca tggctgtggc taaactatcc tgtggcaata ttaagattaa tgctatctat    600
ggtcttataa ttgctatatt tattgggggt tttgatatat tctgtatctc catgtcttat    660
gccatgatta tccatgctgt ggtgaagcta tcttcggcag atgctcgcca taaagccttc    720
agtacctgta catcacacat atgtgctatt gttattacct atgtcccagc attcttcaac    780
ttctttactc atcgctttgg gagaaccact atacccatc atatccacat tattatagcc    840
aacctgtatc tattgctacc tcccaccttg aatccaattg tatatggagt aaagaccaag    900
cagattcgtg aaggtgtgat caaactgttt gctagacaaa aagttgtttg a            951
```

<210> SEQ ID NO 18
<211> LENGTH: 316
<212> TYPE: PRT
<213> ORGANISM: Mus musculus

<400> SEQUENCE: 18

```
Met Pro Gly Val Asn Thr Ser Ser Leu Thr Pro Arg Tyr Phe Ile Leu
1               5                   10                  15

Asn Gly Ile Pro Gly Leu Glu Ala Ala His Ile Trp Ile Ser Leu Pro
            20                  25                  30

Phe Phe Ile Met Tyr Leu Ile Ala Val Thr Gly Asn Cys Gly Leu Ile
        35                  40                  45

Tyr Leu Ile Ser His Glu Glu Ala Leu His Arg Pro Met Tyr Tyr Phe
    50                  55                  60

Leu Ala Met Leu Ser Ala Thr Asp Ile Ser Gly Cys Asn Thr Ile Val
65                  70                  75                  80

Pro Ser Met Leu Cys Ile Phe Trp Phe Ser Val Lys Glu Ile Asp Phe
                85                  90                  95

Asn Ala Cys Leu Val Gln Met Phe Phe Ile His Met Leu Thr Gly Met
            100                 105                 110

Glu Ser Gly Val Leu Met Leu Met Ala Leu Asp Arg Tyr Val Ala Ile
        115                 120                 125

Cys Tyr Pro Leu Arg Tyr Thr Thr Ile Leu Thr Asn Thr Met Ile Thr
    130                 135                 140

Lys Ile Gly Leu Ala Ala Leu Val Arg Ser Val Leu Leu Met Val Pro
145                 150                 155                 160

Phe Ala Phe Leu Ile Lys Arg Leu Pro Tyr Cys Arg Gly Asn Leu Ile
                165                 170                 175

Gln His Thr Tyr Cys Asp His Met Ala Val Ala Lys Leu Ser Cys Gly
            180                 185                 190

Asn Ile Lys Ile Asn Ala Ile Tyr Gly Leu Ile Ile Ala Ile Phe Ile
        195                 200                 205

Gly Gly Phe Asp Ile Phe Cys Ile Ser Met Ser Tyr Ala Met Ile Ile
    210                 215                 220

His Ala Val Val Lys Leu Ser Ser Ala Asp Ala Arg His Lys Ala Phe
225                 230                 235                 240

Ser Thr Cys Thr Ser His Ile Cys Ala Ile Val Ile Thr Tyr Val Pro
                245                 250                 255

Ala Phe Phe Asn Phe Phe Thr His Arg Phe Gly Arg Thr Thr Ile Pro
            260                 265                 270
```

His His Ile His Ile Ile Ala Asn Leu Tyr Leu Leu Pro Pro
        275                 280                 285

Thr Leu Asn Pro Ile Val Tyr Gly Val Lys Thr Lys Gln Ile Arg Glu
        290                 295                 300

Gly Val Ile Lys Leu Phe Ala Arg Gln Lys Val Val
305                 310                 315

<210> SEQ ID NO 19
<211> LENGTH: 954
<212> TYPE: DNA
<213> ORGANISM: Mus musculus

<400> SEQUENCE: 19

```
atgctgattt ccaacaactc atatgaagcc ccgcagtctt tcattcttaa tggaattcct       60
ggtctcgaag cagtgcatat atggatctct cttccactct gtacaatgta catcatctcc      120
ctagtaggca accttggcct tgtatatctc atttactatg aggaatcctt acatcgccca      180
atgtatttct ttctggccat gctttctctc atagacctgt ttacttgcac aaccactgtc      240
cccaatgccc tcttcatttt ctggttcaaa ctcaaggaaa ttaacttcac tgcttgccta      300
gttcagatgt tctttgtgca cggattcaca ggtgtgagt ctggggtact catgctcatg       360
gccttggacc gctatgtggc catttgctac ccactacgct atgcaaccat acttaccaac      420
cctgtcattg ccaaagctgg gcttgccacc ttcttgagag gtgtgttact gatgattcct      480
tttccattct tggttaaacg tttgcccttc tgccgaagca atgtcatctc catacatat      540
tgtgaccaca tgtctgtggt aaagttatcc tgtgccagca tcaaaatcaa tgtcatctat      600
ggtctcatgg ttgcacttct gattggagtg tttgacatat gttgtatatc tgtgtcctac      660
actatgatcc tccgggcagt ggtcagcctg tcctctgcag atgctcggca gaaggccttc      720
agcacctgca cagcccacat atctgccatc atcattactt atgttccagc cttcttcacc      780
ttctttactc atcgttttgg aggtcacacc atccctcctt ctcttcatat cattgtggct      840
aatctttatc ttcttctccc tccaactcta aatcccattg tttatgggat gaagaccaaa      900
cagatcagag atagtatcat taaattcttt cacggtgaaa aaggttcaag gtga            954
```

<210> SEQ ID NO 20
<211> LENGTH: 317
<212> TYPE: PRT
<213> ORGANISM: Mus musculus

<400> SEQUENCE: 20

Met Leu Ile Ser Asn Asn Ser Tyr Glu Ala Pro Gln Ser Phe Ile Leu
1               5                   10                  15

Asn Gly Ile Pro Gly Leu Glu Ala Val His Ile Trp Ile Ser Leu Pro
            20                  25                  30

Leu Cys Thr Met Tyr Ile Ile Ser Leu Val Gly Asn Leu Gly Leu Val
        35                  40                  45

Tyr Leu Ile Tyr Tyr Glu Glu Ser Leu His Arg Pro Met Tyr Phe Phe
    50                  55                  60

Leu Ala Met Leu Ser Leu Ile Asp Leu Phe Thr Cys Thr Thr Thr Val
65                  70                  75                  80

Pro Asn Ala Leu Phe Ile Phe Trp Phe Lys Leu Lys Glu Ile Asn Phe
                85                  90                  95

Thr Ala Cys Leu Val Gln Met Phe Phe Val His Gly Phe Thr Gly Val
            100                 105                 110

```
Glu Ser Gly Val Leu Met Leu Met Ala Leu Asp Arg Tyr Val Ala Ile
            115                 120                 125

Cys Tyr Pro Leu Arg Tyr Ala Thr Ile Leu Thr Asn Pro Val Ile Ala
        130                 135                 140

Lys Ala Gly Leu Ala Thr Phe Leu Arg Gly Val Leu Leu Met Ile Pro
145                 150                 155                 160

Phe Pro Phe Leu Val Lys Arg Leu Pro Phe Cys Arg Ser Asn Val Ile
                165                 170                 175

Ser His Thr Tyr Cys Asp His Met Ser Val Val Lys Leu Ser Cys Ala
            180                 185                 190

Ser Ile Lys Ile Asn Val Ile Tyr Gly Leu Met Val Ala Leu Leu Ile
        195                 200                 205

Gly Val Phe Asp Ile Cys Cys Ile Ser Val Ser Tyr Thr Met Ile Leu
    210                 215                 220

Arg Ala Val Val Ser Leu Ser Ser Ala Asp Ala Arg Gln Lys Ala Phe
225                 230                 235                 240

Ser Thr Cys Thr Ala His Ile Ser Ala Ile Ile Thr Tyr Val Pro
                245                 250                 255

Ala Phe Phe Thr Phe Phe Thr His Arg Phe Gly His Thr Ile Pro
                260                 265                 270

Pro Ser Leu His Ile Ile Val Ala Asn Leu Tyr Leu Leu Leu Pro Pro
            275                 280                 285

Thr Leu Asn Pro Ile Val Tyr Gly Met Lys Thr Lys Gln Ile Arg Asp
        290                 295                 300

Ser Ile Ile Lys Phe Phe His Gly Glu Lys Gly Ser Arg
305                 310                 315

<210> SEQ ID NO 21
<211> LENGTH: 936
<212> TYPE: DNA
<213> ORGANISM: Mus musculus

<400> SEQUENCE: 21
atgcaaaacc agagttttgt aacagaattc atattccttg gactttcaca gaaccctaaa      60
gtccagaaaa tagttttat tgtatttta tttgtctaca ttgcaactgt tgggggcaac      120
atgataattg tggtgaccat tgtctgtagc ccagcattga tagactgccc catgtacttc      180 ttttttggcat tcttgtccct attggatgca tgcttctctt ctgtcatcac accaaagatg      240
gttgtggact ccctgtatga aagaaaact atctcctttg aaggatgtat gatgcagtta      300
tttgctgagc acttccttgc agcagtagaa gtgattgtct tgacagccat ggcctatgac      360
cgctatgtag caatttgcaa gcccttgcac tactcttcca tcatgaactg gaggctctgt      420
ggcacactta tggggatagc atggacaggg ggcttcttgc attctatcat acaaattatc      480
ttcacgttgc aattgcccct ctgtggacca atgtcatcg atcatttcat gtgtgacttg      540
ttcccattac tggaacttgc ctgcactgat actcatatct ttggcctttt agtggttgcc      600
aacagtgggt ctatctgcat cataatcttc tctatttgc tggtctccta tggtgtcatc      660
ctgttctctc tgaaagctca cagttctgaa gggcgatgga agctctctc cacatgtgga      720 tcccacattg cagttgtggt tttgttcttt gtcccgtgta tatttattta tgcacgtcct      780
ccatctgctt tctccttga taaaatggtg gcgatatttt atactatcct aactcccttg      840
ctcaatcctg tgattatac ttttcggaat aaggacatga aaatgctat gaagaaagtg      900 tggaagaggt tggcagtggt ttctgatgga aagtga                                936
```

<210> SEQ ID NO 22
<211> LENGTH: 311
<212> TYPE: PRT
<213> ORGANISM: Mus musculus

<400> SEQUENCE: 22

```
Met Gln Asn Gln Ser Phe Val Thr Glu Phe Ile Phe Leu Gly Leu Ser
1               5                   10                  15

Gln Asn Pro Lys Val Gln Lys Ile Val Phe Ile Val Phe Leu Phe Val
            20                  25                  30

Tyr Ile Ala Thr Val Gly Gly Asn Met Ile Ile Val Thr Ile Val
        35                  40                  45

Cys Ser Pro Ala Leu Ile Asp Cys Pro Met Tyr Phe Phe Leu Ala Phe
    50                  55                  60

Leu Ser Leu Leu Asp Ala Cys Phe Ser Ser Val Ile Thr Pro Lys Met
65                  70                  75                  80

Val Val Asp Ser Leu Tyr Glu Lys Lys Thr Ile Ser Phe Glu Gly Cys
                85                  90                  95

Met Met Gln Leu Phe Ala Glu His Phe Leu Ala Ala Val Glu Val Ile
            100                 105                 110

Val Leu Thr Ala Met Ala Tyr Asp Arg Tyr Val Ala Ile Cys Lys Pro
        115                 120                 125

Leu His Tyr Ser Ser Ile Met Asn Trp Arg Leu Cys Gly Thr Leu Met
    130                 135                 140

Gly Ile Ala Trp Thr Gly Gly Phe Leu His Ser Ile Ile Gln Ile Ile
145                 150                 155                 160

Phe Thr Leu Gln Leu Pro Phe Cys Gly Pro Asn Val Ile Asp His Phe
                165                 170                 175

Met Cys Asp Leu Phe Pro Leu Leu Glu Leu Ala Cys Thr Asp Thr His
            180                 185                 190

Ile Phe Gly Leu Leu Val Val Ala Asn Ser Gly Ser Ile Cys Ile Ile
        195                 200                 205

Ile Phe Ser Ile Leu Leu Val Ser Tyr Gly Val Ile Leu Phe Ser Leu
    210                 215                 220

Lys Ala His Ser Ser Glu Gly Arg Trp Lys Ala Leu Ser Thr Cys Gly
225                 230                 235                 240

Ser His Ile Ala Val Val Leu Phe Phe Val Pro Cys Ile Phe Ile
                245                 250                 255

Tyr Ala Arg Pro Pro Ser Ala Phe Ser Phe Asp Lys Met Val Ala Ile
            260                 265                 270

Phe Tyr Thr Ile Leu Thr Pro Leu Leu Asn Pro Val Ile Tyr Thr Phe
        275                 280                 285

Arg Asn Lys Asp Met Lys Asn Ala Met Lys Lys Val Trp Lys Arg Leu
    290                 295                 300

Ala Val Val Ser Asp Gly Lys
305                 310
```

<210> SEQ ID NO 23
<211> LENGTH: 975
<212> TYPE: DNA
<213> ORGANISM: Homo sapiens

<400> SEQUENCE: 23

```
atgcctctat ttaattcatt atgctggttt ccaacaattc atgtgactcc tccatctttt      60
attcttaatg gaatacctgg tctggaaaga gtacatgtat ggatctccct cccactctgc     120
```

```
acaatgtaca tcatcttcct tgtggggaat cttggtcttg tgtacctcat ttattatgag      180
gagtccttac atcatccgat gtattttttt tttggccatg ctctctccct cattgacctc      240
cttacctgca ccaccactct acccaatgca ctctgcatct tctggttcag tctcaaagaa      300
attaacttca atgcttgctt ggcccagatg ttctttgttc atgggttcac aggtgtggag      360
tctggggtgc tcatgctcat ggctctagac cgctatgtag ccatttgcta cccttttgcgt     420 tatgctacca cactcaccaa ccctatcatt gccaaggctg agcttgccac cttcctgagg      480
ggtgtattgc tgatgattcc tttcccattc ttggttaagc gtttgccttt ctgccaaagc      540
aatattatct cccatacgta ctgcgaccac atgtctgtag taaagctatc ttgtgccagc      600
atcaaggtca atgtaatcta tggtctaatg gttgctctcc tgattggagt gtttgacatt      660
tgttgtatat ctttgtctta cactttgatc ctcaaggcag cgatcagcct ctcttcatca      720
gatgctcggc agaaggcttt cagcacctgc actgcccata tatctgccat catcatcacc      780
tatgttccag cattcttcac tttctttgcc accgttttg ggggacacac aattcccct      840 tctcttcaca tcattgtggc taatctttat cttcttcttc ccccaactct aaaccctatt      900
gtttatggag taaagacaaa acagatacgc aagagtgtca taaagttctt ccagggtgat      960
aagggtgcag gttga                                                       975
```

<210> SEQ ID NO 24
<211> LENGTH: 324
<212> TYPE: PRT
<213> ORGANISM: Homo sapiens

<400> SEQUENCE: 24

Met Pro Leu Phe Asn Ser Leu Cys Trp Phe Pro Thr Ile His Val Thr
1               5                   10                  15

Pro Pro Ser Phe Ile Leu Asn Gly Ile Pro Gly Leu Glu Arg Val His
                20                  25                  30

Val Trp Ile Ser Leu Pro Leu Cys Thr Met Tyr Ile Ile Phe Leu Val
            35                  40                  45

Gly Asn Leu Gly Leu Val Tyr Leu Ile Tyr Tyr Glu Glu Ser Leu His
        50                  55                  60

His Pro Met Tyr Phe Phe Phe Gly His Ala Leu Ser Leu Ile Asp Leu
65                  70                  75                  80

Leu Thr Cys Thr Thr Thr Leu Pro Asn Ala Leu Cys Ile Phe Trp Phe
                85                  90                  95

Ser Leu Lys Glu Ile Asn Phe Asn Ala Cys Leu Ala Gln Met Phe Phe
                100                 105                 110

Val His Gly Phe Thr Gly Val Glu Ser Gly Val Leu Met Leu Met Ala
            115                 120                 125

Leu Asp Arg Tyr Val Ala Ile Cys Tyr Pro Leu Arg Tyr Ala Thr Thr
        130                 135                 140

Leu Thr Asn Pro Ile Ile Ala Lys Ala Glu Leu Ala Thr Phe Leu Arg
145                 150                 155                 160

Gly Val Leu Leu Met Ile Pro Phe Pro Phe Leu Val Lys Arg Leu Pro
                165                 170                 175

Phe Cys Gln Ser Asn Ile Ile Ser His Thr Tyr Cys Asp His Met Ser
                180                 185                 190

Val Val Lys Leu Ser Cys Ala Ser Ile Lys Val Asn Val Ile Tyr Gly
            195                 200                 205

Leu Met Val Ala Leu Leu Ile Gly Val Phe Asp Ile Cys Cys Ile Ser

Leu Ser Tyr Thr Leu Ile Leu Lys Ala Ala Ile Ser Leu Ser Ser
225                 230                 235                 240

Asp Ala Arg Gln Lys Ala Phe Ser Thr Cys Thr Ala His Ile Ser Ala
            245                 250                 255

Ile Ile Ile Thr Tyr Val Pro Ala Phe Phe Thr Phe Ala His Arg
            260                 265                 270

Phe Gly Gly His Thr Ile Pro Pro Ser Leu His Ile Ile Val Ala Asn
            275                 280                 285

Leu Tyr Leu Leu Leu Pro Pro Thr Leu Asn Pro Ile Val Tyr Gly Val
            290                 295                 300

Lys Thr Lys Gln Ile Arg Lys Ser Val Ile Lys Phe Phe Gln Gly Asp
305                 310                 315                 320

Lys Gly Ala Gly

<210> SEQ ID NO 25
<211> LENGTH: 939
<212> TYPE: DNA
<213> ORGANISM: Homo sapiens

<400> SEQUENCE: 25
atggagaaat ggaatcacac ttcaaatgat ttcattttgt tgggtctgct tccccccaaat    60
caaactggaa tatttctctt gtgccttatc atcctctatat tctttctggc ctcggtgggt   120
aactcggcca tgattcacct catccacgtg gatcctcgtc tccacacacc gatgtacttt   180
cttctcagcc agctctccct tatggacctg atgtacatct ccaccaccgt ccccaagatg   240
gcgtacaact tcctgtccgg ccagaaaggc atctccttcc tgggatgtgg tgtgcaaagc   300
ttcttcttcc tgaccatggc gtgttctgaa ggcttactcc tgacctccat ggcctacgac   360
cgttatttgg ccatctgcca ctctctctat tatcctatcc gcatgagtaa aatgatgtgt   420
gtgaagatga ttggaggctc ttggacactg ggtccatca actccttggc acacacagtc   480
tttgcccttc atattcccta ctgcaggtct agggctattg accatttctt ctgcgatgtc   540
ccagccatgt tgcttcttgc ctgtacagat acttgggtct atgaatatat ggttttttgta   600
agtacaagcc tctttctcct tttcccttc attggcatca cttcttcctg tggccgagtc   660
ctatttgctg tctatcatat gcactcaaag gaggggagaa aaaaggcctt caccaccatt   720
tcaacacatt taactgtagt gatctttttac tatgcacctt ttgtctacac ctatcttcgg   780
cccaggaatc tccgctcacc agctgaagac aagatcctgg cagtcttcta ccaccatcctt   840
acccccatgc tcaatcccat tatctacagc ctgaggaata aggaagtcct ggggggctatg   900
aggagagtgt ttgggatatt ctctttcctg aaagaataa                           939

<210> SEQ ID NO 26
<211> LENGTH: 312
<212> TYPE: PRT
<213> ORGANISM: Homo sapiens

<400> SEQUENCE: 26

Met Glu Lys Trp Asn His Thr Ser Asn Asp Phe Ile Leu Leu Gly Leu
1               5                   10                  15

Leu Pro Pro Asn Gln Thr Gly Ile Phe Leu Leu Cys Leu Ile Ile Leu
            20                  25                  30

Ile Phe Phe Leu Ala Ser Val Gly Asn Ser Ala Met Ile His Leu Ile
            35                  40                  45

His Val Asp Pro Arg Leu His Thr Pro Met Tyr Phe Leu Leu Ser Gln
            50                  55                  60

Leu Ser Leu Met Asp Leu Met Tyr Ile Ser Thr Thr Val Pro Lys Met
 65                  70                  75                  80

Ala Tyr Asn Phe Leu Ser Gly Gln Lys Gly Ile Ser Phe Leu Gly Cys
                 85                  90                  95

Gly Val Gln Ser Phe Phe Leu Thr Met Ala Cys Ser Glu Gly Leu
            100                 105                 110

Leu Leu Thr Ser Met Ala Tyr Asp Arg Tyr Leu Ala Ile Cys His Ser
            115                 120                 125

Leu Tyr Tyr Pro Ile Arg Met Ser Lys Met Met Cys Val Lys Met Ile
130                 135                 140

Gly Gly Ser Trp Thr Leu Gly Ser Ile Asn Ser Leu Ala His Thr Val
145                 150                 155                 160

Phe Ala Leu His Ile Pro Tyr Cys Arg Ser Arg Ala Ile Asp His Phe
                165                 170                 175

Phe Cys Asp Val Pro Ala Met Leu Leu Leu Ala Cys Thr Asp Thr Trp
            180                 185                 190

Val Tyr Glu Tyr Met Val Phe Val Ser Thr Ser Leu Phe Leu Leu Phe
            195                 200                 205

Pro Phe Ile Gly Ile Thr Ser Ser Cys Gly Arg Val Leu Phe Ala Val
210                 215                 220

Tyr His Met His Ser Lys Glu Gly Arg Lys Lys Ala Phe Thr Thr Ile
225                 230                 235                 240

Ser Thr His Leu Thr Val Val Ile Phe Tyr Tyr Ala Pro Phe Val Tyr
                245                 250                 255

Thr Tyr Leu Arg Pro Arg Asn Leu Arg Ser Pro Ala Glu Asp Lys Ile
            260                 265                 270

Leu Ala Val Phe Tyr Thr Ile Leu Thr Pro Met Leu Asn Pro Ile Ile
            275                 280                 285

Tyr Ser Leu Arg Asn Lys Glu Val Leu Gly Ala Met Arg Arg Val Phe
290                 295                 300

Gly Ile Phe Ser Phe Leu Lys Glu
305                 310

<210> SEQ ID NO 27
<211> LENGTH: 879
<212> TYPE: DNA
<213> ORGANISM: Homo sapiens

<400> SEQUENCE: 27
atgagtgtaa cagaaaatac gctcatgatc ctcctcattc gcagtgactc ccgactccac      60
actccaatgt attttctgct cagccatctc tccttaatgg atatcttgca tgtttccaac     120
atcgttccca aaatggtcac taactttctg tcaggcagca gaactatttc atttgcaggt     180
tgtgggttcc aggtatttct gtccctcacc ctcctgggtg gtgagtgcct tctcctggct     240
gcaatgtcct gtgatcgcta tgtggctatc tgtcacccgc tgcgctatcc gattcttatg     300
aaggagtatg ccagcgctct catggctgga ggctcctggc tcattggggt tttcaactcc     360
acagtccaca cagcttatgc actgcagttt cccttctgtg ctctagggc aattgatcac     420 ttcttctgtg aagtccctgc catgttgaag ttgtcctgtg cagacacaac acgctatgaa     480 cgagggggttt gtgtaagtgc tgtgatcttc ctgctgatcc ctttctcctt gatctctgct     540
tcttatggcc aaattattct tactgtcctc cagatgaaat catcagaggc aaggaaaaag     600

```
tcattttcca cttgttcctt ccacatgatt gtggtcacga gtactatgg gccatttatt      660 tttacatata tgagacctaa atcataccac actccagggc aggataagtt cctggcaata      720
ttctatacga tcctcacacc cacactcaac cctttcatct acagctttag gaataaagat      780
gttctggcgg tgatgaaaaa tatgctcaaa gtaactttc tgcacaaaaa aatgaatagg       840
aaaattcctg aatgtgtgtt ctgtctattt ctatgttaa                             879
```

<210> SEQ ID NO 28
<211> LENGTH: 292
<212> TYPE: PRT
<213> ORGANISM: Homo sapiens

<400> SEQUENCE: 28

```
Met Ser Val Thr Glu Asn Thr Leu Met Ile Leu Leu Ile Arg Ser Asp
1               5                   10                  15

Ser Arg Leu His Thr Pro Met Tyr Phe Leu Ser His Leu Ser Leu
                20                  25                  30

Met Asp Ile Leu His Val Ser Asn Ile Val Pro Lys Met Val Thr Asn
            35                  40                  45

Phe Leu Ser Gly Ser Arg Thr Ile Ser Phe Ala Gly Cys Gly Phe Gln
    50                  55                  60

Val Phe Leu Ser Leu Thr Leu Leu Gly Gly Glu Cys Leu Leu Leu Ala
65                  70                  75                  80

Ala Met Ser Cys Asp Arg Tyr Val Ala Ile Cys His Pro Leu Arg Tyr
                85                  90                  95

Pro Ile Leu Met Lys Glu Tyr Ala Ser Ala Leu Met Ala Gly Gly Ser
                100                 105                 110

Trp Leu Ile Gly Val Phe Asn Ser Thr Val His Thr Ala Tyr Ala Leu
            115                 120                 125

Gln Phe Pro Phe Cys Gly Ser Arg Ala Ile Asp His Phe Phe Cys Glu
    130                 135                 140

Val Pro Ala Met Leu Lys Leu Ser Cys Ala Asp Thr Thr Arg Tyr Glu
145                 150                 155                 160

Arg Gly Val Cys Val Ser Ala Val Ile Phe Leu Leu Ile Pro Phe Ser
                165                 170                 175

Leu Ile Ser Ala Ser Tyr Gly Gln Ile Ile Leu Thr Val Leu Gln Met
                180                 185                 190

Lys Ser Ser Glu Ala Arg Lys Lys Ser Phe Ser Thr Cys Ser Phe His
            195                 200                 205

Met Ile Val Val Thr Met Tyr Tyr Gly Pro Phe Ile Phe Thr Tyr Met
    210                 215                 220

Arg Pro Lys Ser Tyr His Thr Pro Gly Gln Asp Lys Phe Leu Ala Ile
225                 230                 235                 240

Phe Tyr Thr Ile Leu Thr Pro Thr Leu Asn Pro Phe Ile Tyr Ser Phe
                245                 250                 255

Arg Asn Lys Asp Val Leu Ala Val Met Lys Asn Met Leu Lys Ser Asn
                260                 265                 270

Phe Leu His Lys Lys Met Asn Arg Lys Ile Pro Glu Cys Val Phe Cys
            275                 280                 285

Leu Phe Leu Cys
    290
```

<210> SEQ ID NO 29
<211> LENGTH: 1113
<212> TYPE: DNA

<213> ORGANISM: Homo sapiens

<400> SEQUENCE: 29

```
atgttctcaa tgacaacaga agcactcaat aattttgcac ttggatgtac caacttgtta      60
atgactatga taccacaaat tgatctgaag caaattttcc tttgtcctaa ttgcagacta     120
tacatgatcc ctgttggagc tttcatcttt tccttgggaa acatgcaaaa ccaaagcttt     180
gtaactgagt ttgtcctcct gggactttca cagaatccaa atgttcagga atagtatttt    240
gttgtatttt tgtttgtcta cattgcaact gttgggggca acatgctaat tgtagtaacc     300
attctcagca gccctgctct tctggtgtct cctatgtact tcttcttggg cttcctgtcc     360
ttcctggatg cgtgcttctc atctgtcatc accccaaaga tgattgtaga ctccctctat     420
gtgacaaaaa ccatctcttt tgaaggctgc atgatgcagc tctttgctga acacttcttt     480
gctggggtgg aggtgattgt cctcacagcc atggcctatg atcgttatgt ggccatttgc     540
aagcccttgc attactcttc tatcatgaac aggaggctct gtggcattct gatggggta     600
gcctggacag ggggcctctt gcattccatg atacaaattc tttttacttt ccagcttccc     660
ttttgtggcc ccaatgtcat caatcacttt atgtgtgact tgtacccgtt actggagctt     720
gcctgcactg atactcacat ctttggcctc atggtggtca tcaacagtgg gtttatctgc     780
atcataaact tctccttgtt gcttgtctcc tatgctgtca tcttgctctc tctgagaaca     840
cacagttctg aagggcgctg gaaagctctc tccacctgtg gatctcacat tgctgttgtg     900
attttgttct tgtcccatg catatttgta tatacgac ctccatctgc ttttccctt      960
gacaaaatgg cggcaatatt ttatatcatc ttaaatccct tgctcaatcc tttgatttac    1020
acttcagga ataaggaagt aaaacaggcc atgaggagaa tatggaacag actgatggtg     1080
gtttctgatg agaagaaaa tattaaactt taa                                  1113
```

<210> SEQ ID NO 30
<211> LENGTH: 370
<212> TYPE: PRT
<213> ORGANISM: Homo sapiens

<400> SEQUENCE: 30

```
Met Phe Ser Met Thr Thr Glu Ala Leu Asn Asn Phe Ala Leu Gly Cys
1               5                   10                  15

Thr Asn Leu Leu Met Thr Met Ile Pro Gln Ile Asp Leu Lys Gln Ile
            20                  25                  30

Phe Leu Cys Pro Asn Cys Arg Leu Tyr Met Ile Pro Val Gly Ala Phe
        35                  40                  45

Ile Phe Ser Leu Gly Asn Met Gln Asn Gln Ser Phe Val Thr Glu Phe
    50                  55                  60

Val Leu Leu Gly Leu Ser Gln Asn Pro Asn Val Gln Glu Ile Val Phe
65                  70                  75                  80

Val Val Phe Leu Phe Val Tyr Ile Ala Thr Val Gly Gly Asn Met Leu
                85                  90                  95

Ile Val Val Thr Ile Leu Ser Ser Pro Ala Leu Leu Val Ser Pro Met
            100                 105                 110

Tyr Phe Phe Leu Gly Phe Leu Ser Phe Leu Asp Ala Cys Phe Ser Ser
        115                 120                 125

Val Ile Thr Pro Lys Met Ile Val Asp Ser Leu Tyr Val Thr Lys Thr
    130                 135                 140

Ile Ser Phe Glu Gly Cys Met Met Gln Leu Phe Ala Glu His Phe Phe
145                 150                 155                 160
```

Ala Gly Val Glu Val Ile Val Leu Thr Ala Met Ala Tyr Asp Arg Tyr
            165                 170                 175

Val Ala Ile Cys Lys Pro Leu His Tyr Ser Ser Ile Met Asn Arg Arg
            180                 185                 190

Leu Cys Gly Ile Leu Met Gly Val Ala Trp Thr Gly Gly Leu Leu His
            195                 200                 205

Ser Met Ile Gln Ile Leu Phe Thr Phe Gln Leu Pro Phe Cys Gly Pro
        210                 215                 220

Asn Val Ile Asn His Phe Met Cys Asp Leu Tyr Pro Leu Leu Glu Leu
225                 230                 235                 240

Ala Cys Thr Asp Thr His Ile Phe Gly Leu Met Val Val Ile Asn Ser
            245                 250                 255

Gly Phe Ile Cys Ile Ile Asn Phe Ser Leu Leu Leu Val Ser Tyr Ala
        260                 265                 270

Val Ile Leu Leu Ser Leu Arg Thr His Ser Ser Glu Gly Arg Trp Lys
            275                 280                 285

Ala Leu Ser Thr Cys Gly Ser His Ile Ala Val Val Ile Leu Phe Phe
            290                 295                 300

Val Pro Cys Ile Phe Val Tyr Thr Arg Pro Pro Ser Ala Phe Ser Leu
305                 310                 315                 320

Asp Lys Met Ala Ala Ile Phe Tyr Ile Ile Leu Asn Pro Leu Leu Asn
            325                 330                 335

Pro Leu Ile Tyr Thr Phe Arg Asn Lys Glu Val Lys Gln Ala Met Arg
            340                 345                 350

Arg Ile Trp Asn Arg Leu Met Val Val Ser Asp Glu Lys Glu Asn Ile
            355                 360                 365

Lys Leu
    370

<210> SEQ ID NO 31
<211> LENGTH: 930
<212> TYPE: DNA
<213> ORGANISM: Homo sapiens

<400> SEQUENCE: 31
atggatatat cagagggaaa taagactctt gtgacagagt ttgttctcac aggacttaca      60
gatcgaccat ggctgcacgt cctcttcttt gttgtgtttt tggtggtcta tctcatcacc     120
atggtgggca accttggact gatagttcta atttggaacg accccatct tcatatgccc      180
atgtacttat ccttggtgg tttagccttt tcagatgctt gtacttcaac ctctataacc      240
cctaggatgc tggtcaattt cttagacaag actgcaatga tatccctagc tgagtgcatc      300
acccagtttt actttttgc ttccagtgca actacagaat gcttcctcct ggtgatgatg      360
gcctatgacc gctatgtagc catatgtaat cccttgcttt atccagtgat gatgtccaac      420
aaactcagcg ctcagttgct aagtatttca tatgtaattg gtttcctgca tcctctggtt      480
catgtgagtt actattgcg actaactttc tgcaggttta acataataca ttatttctac      540
tgtgaaattt tacaactgtt caaaatttca tgcaatggtc catctattaa cgcactaatg      600
atatttattt ttggtgcttt tatacaaata cccactttaa tgactatcat aatctcttat      660
actcgtgtgc tctttgatat tctgaaaaaa aagtctgaaa agggcagaag caaagccttc      720
tccacatgcg gcgcccatct gctttctgtc tcattgtact acggaactct gatcttcatg      780
tatgtgcgtc ctgcatctgg cttagctgaa gaccaagaca aagtgtattc tctgttttac      840

```
acgattataa ttcccctgct aaacccattt atttacagct tgagaaataa aaaagtcatg       900
catgcattga aagagttat aaggaagtaa                                         930
```

<210> SEQ ID NO 32
<211> LENGTH: 309
<212> TYPE: PRT
<213> ORGANISM: Homo sapiens

<400> SEQUENCE: 32

```
Met Asp Ile Ser Glu Gly Asn Lys Thr Leu Val Thr Glu Phe Val Leu
1               5                   10                  15

Thr Gly Leu Thr Asp Arg Pro Trp Leu His Val Leu Phe Phe Val Val
            20                  25                  30

Phe Leu Val Val Tyr Leu Ile Thr Met Val Gly Asn Leu Gly Leu Ile
        35                  40                  45

Val Leu Ile Trp Asn Asp Pro His Leu His Met Pro Met Tyr Leu Phe
    50                  55                  60

Leu Gly Gly Leu Ala Phe Ser Asp Ala Cys Thr Ser Thr Ser Ile Thr
65                  70                  75                  80

Pro Arg Met Leu Val Asn Phe Leu Asp Lys Thr Ala Met Ile Ser Leu
                85                  90                  95

Ala Glu Cys Ile Thr Gln Phe Tyr Phe Phe Ala Ser Ser Ala Thr Thr
            100                 105                 110

Glu Cys Phe Leu Leu Val Met Met Ala Tyr Asp Arg Tyr Val Ala Ile
        115                 120                 125

Cys Asn Pro Leu Leu Tyr Pro Val Met Met Ser Asn Lys Leu Ser Ala
    130                 135                 140

Gln Leu Leu Ser Ile Ser Tyr Val Ile Gly Phe Leu His Pro Leu Val
145                 150                 155                 160

His Val Ser Leu Leu Leu Arg Leu Thr Phe Cys Arg Phe Asn Ile Ile
                165                 170                 175

His Tyr Phe Tyr Cys Glu Ile Leu Gln Leu Phe Lys Ile Ser Cys Asn
            180                 185                 190

Gly Pro Ser Ile Asn Ala Leu Met Ile Phe Ile Phe Gly Ala Phe Ile
        195                 200                 205

Gln Ile Pro Thr Leu Met Thr Ile Ile Ser Tyr Thr Arg Val Leu
    210                 215                 220

Phe Asp Ile Leu Lys Lys Lys Ser Glu Lys Gly Arg Ser Lys Ala Phe
225                 230                 235                 240

Ser Thr Cys Gly Ala His Leu Leu Ser Val Ser Leu Tyr Tyr Gly Thr
                245                 250                 255

Leu Ile Phe Met Tyr Val Arg Pro Ala Ser Gly Leu Ala Glu Asp Gln
            260                 265                 270

Asp Lys Val Tyr Ser Leu Phe Tyr Thr Ile Ile Ile Pro Leu Leu Asn
        275                 280                 285

Pro Phe Ile Tyr Ser Leu Arg Asn Lys Lys Val Met His Ala Leu Arg
    290                 295                 300

Arg Val Ile Arg Lys
305
```

<210> SEQ ID NO 33
<211> LENGTH: 939
<212> TYPE: DNA
<213> ORGANISM: Homo sapiens

<400> SEQUENCE: 33

```
atgatgggta gaaggaatga cacaaatgtg gctgacttca tccttacggg actgtcagac    60
tctgaagagg tccagatggc tctgtttatg ctatttctcc tcatatacct aattactatg   120
ctggggaatg tggggatgct attgataatc cgcctggacc tccagcttca cactcccatg   180 tatttttcc ttactcacct gtcatttatt gacctcagtt actcaactgt cgtcacacct    240
aaaaccttag cgaacttact gacttccaac tatatttcct tcacgggctg ctttgcccag   300
atgttctgtt ttgtcttctt gggtactgct gaatgttatc ttctctcctc aatgcctat    360 gatcgctatg cagcgatctg cagtcctcta cactacacag ttattatgcc caaaaggctc   420
tgcctcgctc tcatcactgg gccttatgtg attggctta tggactcctt tgtcaatgtg    480
gtttccatga gcagattgca tttctgtgac tcaaacataa ttcatcactt tttctgtgac   540
acttccccaa ttttagctct gtcctgcact gacacagaca cactgaaat gctgatattc    600 attatcgctg gttccaccct gatggtgtcc cttatcacaa tatctgcatc ctatgtgtcc   660
attctctcta ccatcctgaa aattaattcc acttcaggaa agcagaaagc tttctctact   720
tgcgtctctc atctcttggg agtcaccatc ttctatgaa ctatgatttt tacttactta    780
aagccaagaa agtcttattc cttgggaaga gatcaagtgg ctcctgtgtt ttatactatt    840
gtgattccca tgctgaatcc actcatttat agtcttagaa acagagaagt gaaaaatgct   900
ctcattagag tcatgcagag aagacaggac tccaggtag                          939
```

<210> SEQ ID NO 34
<211> LENGTH: 312
<212> TYPE: PRT
<213> ORGANISM: Homo sapiens

<400> SEQUENCE: 34

```
Met Met Gly Arg Arg Asn Asp Thr Asn Val Ala Asp Phe Ile Leu Thr
1               5                   10                  15

Gly Leu Ser Asp Ser Glu Glu Val Gln Met Ala Leu Phe Met Leu Phe
            20                  25                  30

Leu Leu Ile Tyr Leu Ile Thr Met Leu Gly Asn Val Gly Met Leu Leu
        35                  40                  45

Ile Ile Arg Leu Asp Leu Gln Leu His Thr Pro Met Tyr Phe Phe Leu
    50                  55                  60

Thr His Leu Ser Phe Ile Asp Leu Ser Tyr Ser Thr Val Val Thr Pro
65                  70                  75                  80

Lys Thr Leu Ala Asn Leu Leu Thr Ser Asn Tyr Ile Ser Phe Thr Gly
                85                  90                  95

Cys Phe Ala Gln Met Phe Cys Phe Val Phe Leu Gly Thr Ala Glu Cys
            100                 105                 110

Tyr Leu Leu Ser Ser Met Ala Tyr Asp Arg Tyr Ala Ala Ile Cys Ser
        115                 120                 125

Pro Leu His Tyr Thr Val Ile Met Pro Lys Arg Leu Cys Leu Ala Leu
    130                 135                 140

Ile Thr Gly Pro Tyr Val Ile Gly Phe Met Asp Ser Phe Val Asn Val
145                 150                 155                 160

Val Ser Met Ser Arg Leu His Phe Cys Asp Ser Asn Ile Ile His His
                165                 170                 175

Phe Phe Cys Asp Thr Ser Pro Ile Leu Ala Leu Ser Cys Thr Asp Thr
            180                 185                 190

Asp Asn Thr Glu Met Leu Ile Phe Ile Ile Ala Gly Ser Thr Leu Met
        195                 200                 205
```

Val Ser Leu Ile Thr Ile Ser Ala Ser Tyr Val Ser Ile Leu Ser Thr
        210                 215                 220

Ile Leu Lys Ile Asn Ser Thr Ser Gly Lys Gln Lys Ala Phe Ser Thr
225                 230                 235                 240

Cys Val Ser His Leu Leu Gly Val Thr Ile Phe Tyr Gly Thr Met Ile
                245                 250                 255

Phe Thr Tyr Leu Lys Pro Arg Lys Ser Tyr Ser Leu Gly Arg Asp Gln
                260                 265                 270

Val Ala Pro Val Phe Tyr Thr Ile Val Ile Pro Met Leu Asn Pro Leu
            275                 280                 285

Ile Tyr Ser Leu Arg Asn Arg Glu Val Lys Asn Ala Leu Ile Arg Val
        290                 295                 300

Met Gln Arg Arg Gln Asp Ser Arg
305                 310

<210> SEQ ID NO 35
<211> LENGTH: 936
<212> TYPE: DNA
<213> ORGANISM: Homo sapiens

<400> SEQUENCE: 35

| | | | | | | |
|---|---|---|---|---|---|---|
| atgaaaatct | tcaacagccc | cagcaactcc | agcaccttca | ctggcttcat | cctcctgggc | 60 |
| ttcccttgcc | ccagggaggg | gcagatcctc | ctctttgtgc | tcttcactgt | tgtttacctc | 120 |
| ctgaccctca | tgggcaatgg | ttccatcatc | tgtgctgtgc | actgggatca | gagactccac | 180 |
| gcccccatgt | acatcctgct | cgccaacttc | tccttcttgg | agatatgtta | tgtcacctcc | 240 |
| acagtcccca | gcatgctggc | caacttcctc | tctgacacca | agatcatctc | gttctctggc | 300 |
| tgcttcctcc | agttctactt | tttcttctcc | ttgggctcta | cagaatgctt | tttcctggca | 360 |
| gttatggcat | tgatcgata | ccttgccatc | tgtcggcctc | tacgctatcc | aaccattatg | 420 |
| accagacgtc | tctgtaccaa | tcttgtggtc | aattgctggg | tacttggttt | catctggttc | 480 |
| ttgattccta | tcgtcaacat | ctcccaaatg | tccttctgtg | gatctaggat | tattgaccac | 540 |
| ttcctatgtg | acccagctcc | tcttctaact | ctcacttgca | aaaaaggccc | tgtgatagag | 600 |
| cttgtctttt | ctgtcttaag | tcctctgcct | gtctttatgc | tctttctctt | cattgtgggg | 660 |
| tcctatgctc | tggtcgtgag | agctgtgttg | agggtcccctt | cagcagctgg | agaagaaaag | 720 |
| gctttctcca | cctgtgggtc | tcacctggct | gtggtttcac | tgttctacgg | ctcagtactg | 780 |
| gtcatgtatg | ggagcccacc | atctaagaat | gaagctggaa | agcagaagac | tgtgactctg | 840 |
| ttttattctg | ttgttacccc | actgcttaac | cctgtgatat | atagtcttag | gaacaaagat | 900 |
| atgagaaaag | ctctgaagaa | attttgggga | acataa | | | 936 |

<210> SEQ ID NO 36
<211> LENGTH: 311
<212> TYPE: PRT
<213> ORGANISM: Homo sapiens

<400> SEQUENCE: 36

Met Lys Ile Phe Asn Ser Pro Ser Asn Ser Ser Thr Phe Thr Gly Phe
1               5                   10                  15

Ile Leu Leu Gly Phe Pro Cys Pro Arg Glu Gly Gln Ile Leu Leu Phe
            20                  25                  30

Val Leu Phe Thr Val Val Tyr Leu Leu Thr Leu Met Gly Asn Gly Ser
        35                  40                  45

Ile Ile Cys Ala Val His Trp Asp Gln Arg Leu His Ala Pro Met Tyr
50                  55                      60

Ile Leu Leu Ala Asn Phe Ser Phe Leu Glu Ile Cys Tyr Val Thr Ser
65                  70                  75                  80

Thr Val Pro Ser Met Leu Ala Asn Phe Leu Ser Asp Thr Lys Ile Ile
            85                  90                  95

Ser Phe Ser Gly Cys Phe Leu Gln Tyr Phe Phe Ser Leu Gly
            100                 105                 110

Ser Thr Glu Cys Phe Phe Leu Ala Val Met Ala Phe Asp Arg Tyr Leu
            115                 120                 125

Ala Ile Cys Arg Pro Leu Arg Tyr Pro Thr Ile Met Thr Arg Arg Leu
130                 135                     140

Cys Thr Asn Leu Val Val Asn Cys Trp Val Leu Gly Phe Ile Trp Phe
145                 150                 155                 160

Leu Ile Pro Ile Val Asn Ile Ser Gln Met Ser Phe Cys Gly Ser Arg
                165                 170                 175

Ile Ile Asp His Phe Leu Cys Asp Pro Ala Pro Leu Leu Thr Leu Thr
            180                 185                 190

Cys Lys Lys Gly Pro Val Ile Glu Leu Val Phe Ser Val Leu Ser Pro
195                 200                 205

Leu Pro Val Phe Met Leu Phe Leu Phe Ile Val Gly Ser Tyr Ala Leu
210                 215                 220

Val Val Arg Ala Val Leu Arg Val Pro Ser Ala Ala Gly Arg Arg Lys
225                 230                 235                 240

Ala Phe Ser Thr Cys Gly Ser His Leu Ala Val Val Ser Leu Phe Tyr
                245                 250                 255

Gly Ser Val Leu Val Met Tyr Gly Ser Pro Pro Ser Lys Asn Glu Ala
            260                 265                 270

Gly Lys Gln Lys Thr Val Thr Leu Phe Tyr Ser Val Val Thr Pro Leu
            275                 280                 285

Leu Asn Pro Val Ile Tyr Ser Leu Arg Asn Lys Asp Met Arg Lys Ala
            290                 295                 300

Leu Lys Lys Phe Trp Gly Thr
305                 310

<210> SEQ ID NO 37
<211> LENGTH: 966
<212> TYPE: DNA
<213> ORGANISM: Homo sapiens

<400> SEQUENCE: 37
atgtctgggg acaacagctc agcctgacc ccaggattct ttatcttgaa tggcgttcct      60
gggctggaag ccacacacat ctggatctcc ctgccattct gctttatgta catcattgct     120
gtcgtgggga actgtgggct catctgcctc atcagccatg aggaggccct gcaccggccc     180
atgtactact tcctggccct gctctccttc actgatgtca ccttgtgcac caccatggta     240
cctaatatgc tgtgcatatt ctggttcaac ctcaaggaga ttgactttaa cgcctgcctg     300
gcccagatgt tttttgtcca tatgctgaca gggatggagt ctggggtgct catgctcatg     360
gccctggacc gctatgtggc catctgctac cccttacgct atgccaccat ccttaccaac     420
cctgtcatcg ccaaggctgg tcttgccacc ttcttgagga atgtgatgct catcatccca     480
ttcactctcc tcaccaagcg cctgcccttat gccggggga acttcatccc ccacacctac     540
tgtgaccata tgtctgtggc caaggtatcc tgtggcaatt tcaaggtcaa tgctatttat     600

```
ggtctgatgg ttgctctcct gattggtgtg tttgatatct gctgtatctc tgtatcttac      660
actatgattt tgcaggctgt tatgagcctg tcatcagcag atgctcgtca caaagccttc      720
agcacctgca catctcacat gtgttccatt gtgatcacct atgttgctgc ttttttcact      780
tttttcactc atcgttttgt aggacacaat atcccaaacc acatacacat catcgtggcc      840
aacctttatc tgctactgcc tcctaccatg aacccaattg tttatggagt caagaccaag      900
cagattcagg aagtgtaat taaattttta cttggagaca aggttagttt tacctatgac      960
aaatga                                                                 966

<210> SEQ ID NO 38
<211> LENGTH: 321
<212> TYPE: PRT
<213> ORGANISM: Homo sapiens

<400> SEQUENCE: 38
```

Met Ser Gly Asp Asn Ser Ser Leu Thr Pro Gly Phe Phe Ile Leu
1               5                   10                  15

Asn Gly Val Pro Gly Leu Glu Ala Thr His Ile Trp Ile Ser Leu Pro
            20                  25                  30

Phe Cys Phe Met Tyr Ile Ile Ala Val Val Gly Asn Cys Gly Leu Ile
        35                  40                  45

Cys Leu Ile Ser His Glu Glu Ala Leu His Arg Pro Met Tyr Tyr Phe
    50                  55                  60

Leu Ala Leu Leu Ser Phe Thr Asp Val Thr Leu Cys Thr Thr Met Val
65                  70                  75                  80

Pro Asn Met Leu Cys Ile Phe Trp Phe Asn Leu Lys Glu Ile Asp Phe
                85                  90                  95

Asn Ala Cys Leu Ala Gln Met Phe Phe Val His Met Leu Thr Gly Met
            100                 105                 110

Glu Ser Gly Val Leu Met Leu Met Ala Leu Asp Arg Tyr Val Ala Ile
        115                 120                 125

Cys Tyr Pro Leu Arg Tyr Ala Thr Ile Leu Thr Asn Pro Val Ile Ala
    130                 135                 140

Lys Ala Gly Leu Ala Thr Phe Leu Arg Asn Val Met Leu Ile Ile Pro
145                 150                 155                 160

Phe Thr Leu Leu Thr Lys Arg Leu Pro Tyr Cys Arg Gly Asn Phe Ile
                165                 170                 175

Pro His Thr Tyr Cys Asp His Met Ser Val Ala Lys Val Ser Cys Gly
            180                 185                 190

Asn Phe Lys Val Asn Ala Ile Tyr Gly Leu Met Val Ala Leu Leu Ile
        195                 200                 205

Gly Val Phe Asp Ile Cys Cys Ile Ser Val Ser Tyr Thr Met Ile Leu
    210                 215                 220

Gln Ala Val Met Ser Leu Ser Ser Ala Asp Ala Arg His Lys Ala Phe
225                 230                 235                 240

Ser Thr Cys Thr Ser His Met Cys Ser Ile Val Ile Thr Tyr Val Ala
                245                 250                 255

Ala Phe Phe Thr Phe Phe Thr His Arg Phe Val Gly His Asn Ile Pro
            260                 265                 270

Asn His Ile His Ile Ile Val Ala Asn Leu Tyr Leu Leu Pro Pro
        275                 280                 285

Thr Met Asn Pro Ile Val Tyr Gly Val Lys Thr Lys Gln Ile Gln Glu
    290                 295                 300

Gly Val Ile Lys Phe Leu Leu Gly Asp Lys Val Ser Phe Thr Tyr Asp
305                 310                 315                 320

Lys

<210> SEQ ID NO 39
<211> LENGTH: 915
<212> TYPE: DNA
<213> ORGANISM: Homo sapiens

<400> SEQUENCE: 39

```
atgtttatat taataagctt cacagaagaa tttgatgtgc aagtcttcct attttttatta      60
tttttagcaa tctatctatt cactctaata ggcaatttag gctggttgt accgatcatt      120
ggggatttct ggcttcacag cccaatgtac tattttcttg gtgttttatc attcttggat     180
gtctgctatt ctacagttgt cactccaaaa atgttggtca atttcctggc aaaaaataaa     240
tctatttcat ttcttggatg tgcaacacag atgtttcttg cttgtacttt tggaaccaca    300
gaatgctttc tcttggctgc aatggcttat gatcgctatg tagccatcta caaccctctc    360
ctgtattcag tgagcatgtc acccagagtc tatgtgccac tcatcactgc ttcctatgtt   420
gctagcattt tacatgctac tatacataca gtggctacat ttagcctgtc cttctgtgga  480
tccaatgaaa ttaggcatgt cttttgtaat atgcctcctc tccttgctat tcttgttct  540
gacactcacg taatccagct tctattcttc tactttgtgg gctctattga atagtcact  600
atcctgattg tcctgatctc ctatggtttt attctgttgg ccattctgaa gatgcagtct  660
gctgaaggga ggagaaaagt cttctctaca tgtggagctc acctaactgg agtgacaatt  720
tatcatggga caatcctctt catgtatgtg agaccaagtt ccagctacac ttcggacaat  780
gacatgatag tgtcaatatt ttataccatt gtgattccca tgctgaatcc catcatctac  840
agtttgcgga acaaagatgt aaaggaggca atcaaaagat tgcttgtgag aaattggttc   900
ataaataagt tatag                                                    915
```

<210> SEQ ID NO 40
<211> LENGTH: 304
<212> TYPE: PRT
<213> ORGANISM: Homo sapiens

<400> SEQUENCE: 40

Met Phe Ile Leu Ile Ser Phe Thr Glu Glu Phe Asp Val Gln Val Phe
1               5                   10                  15

Leu Phe Leu Leu Phe Leu Ala Ile Tyr Leu Phe Thr Leu Ile Gly Asn
                20                  25                  30

Leu Gly Leu Val Val Pro Ile Ile Gly Asp Phe Trp Leu His Ser Pro
            35                  40                  45

Met Tyr Tyr Phe Leu Gly Val Leu Ser Phe Leu Asp Val Cys Tyr Ser
        50                  55                  60

Thr Val Thr Pro Lys Met Leu Val Asn Phe Leu Ala Lys Asn Lys
65                  70                  75                  80

Ser Ile Ser Phe Leu Gly Cys Ala Thr Gln Met Phe Leu Ala Cys Thr
                85                  90                  95

Phe Gly Thr Thr Glu Cys Phe Leu Leu Ala Ala Met Ala Tyr Asp Arg
            100                 105                 110

Tyr Val Ala Ile Tyr Asn Pro Leu Leu Tyr Ser Val Ser Met Ser Pro
        115                 120                 125

Arg Val Tyr Val Pro Leu Ile Thr Ala Ser Tyr Val Ala Ser Ile Leu
    130                 135                 140

His Ala Thr Ile His Thr Val Ala Thr Phe Ser Leu Ser Phe Cys Gly
145                 150                 155                 160

Ser Asn Glu Ile Arg His Val Phe Cys Asn Met Pro Pro Leu Leu Ala
            165                 170                 175

Ile Ser Cys Ser Asp Thr His Val Ile Gln Leu Leu Phe Phe Tyr Phe
        180                 185                 190

Val Gly Ser Ile Glu Ile Val Thr Ile Leu Ile Val Leu Ile Ser Tyr
    195                 200                 205

Gly Phe Ile Leu Leu Ala Ile Leu Lys Met Gln Ser Ala Glu Gly Arg
210                 215                 220

Arg Lys Val Phe Ser Thr Cys Gly Ala His Leu Thr Gly Val Thr Ile
225                 230                 235                 240

Tyr His Gly Thr Ile Leu Phe Met Tyr Val Arg Pro Ser Ser Ser Tyr
                245                 250                 255

Thr Ser Asp Asn Asp Met Ile Val Ser Ile Phe Tyr Thr Ile Val Ile
            260                 265                 270

Pro Met Leu Asn Pro Ile Ile Tyr Ser Leu Arg Asn Lys Asp Val Lys
        275                 280                 285

Glu Ala Ile Lys Arg Leu Leu Val Arg Asn Trp Phe Ile Asn Lys Leu
    290                 295                 300

<210> SEQ ID NO 41
<211> LENGTH: 936
<212> TYPE: DNA
<213> ORGANISM: Homo sapiens

<400> SEQUENCE: 41
atggaaaaaa taaacaacgt aactgaattc attttctggg gtctttctca gagcccagag      60
attgagaaag tttgttttgt ggtgtttttct ttcttctaca taatcattct tctgggaaat    120
ctcctcatca tgctgacagt ttgcctgagc aacctgttta agtcacccat gtatttcttt    180
ctcagcttct tgtcttttgt ggacattgt tactcttcag tcacagctcc caagatgatt    240
gttgacctgt tagcaaagga caaaaccatc tcctatgtgg ggtgcatgtt gcaactgttt    300
ggagtacatt tctttggttg cactgagatc ttcatcctta ctgtaatggc ctatgatcgt    360
tatgtggcta tctgtaaacc cctacattat atgaccatca tgaaccggga gacatgcaat    420
aaaatgttat tagggacgtg ggtaggtggg ttcttacact ccattatcca agtggctctg    480
gtagtccaac tacccttttg tggacccaat gagatagatc actactttg tgatgttcac    540 cctgtgttga aacttgcctg cacagaaaca tacattgttg gtgttgttgt gacagccaac    600
agtggtacca ttgctctggg gagttttgtt atcttgctaa tctcctacag catcatccta    660
gtttccctga aaagcagtc agcagaaggc aggcgcaaag ccctctccac ctgtggctcc    720
cacattgcca tggtcgttat cttttccggc ccctgtactt ttatgtacat gcgccctgat    780
acgacctttt cagaggataa gatggtggct gtatttttaca ccattatcac tcccatgtta    840
aatcctctga tttatacact gagaaatgca gaagtaaaga atgcaatgaa gaaactgtgg    900
ggcagaaatg ttttcttgga ggctaaaggg aaatag                              936

<210> SEQ ID NO 42
<211> LENGTH: 311
<212> TYPE: PRT
<213> ORGANISM: Homo sapiens

<400> SEQUENCE: 42

Met Glu Lys Ile Asn Val Thr Glu Phe Ile Phe Trp Gly Leu Ser
1               5                   10                  15

Gln Ser Pro Glu Ile Glu Lys Val Cys Phe Val Phe Ser Phe Phe
            20                  25                  30

Tyr Ile Ile Ile Leu Leu Gly Asn Leu Leu Ile Met Leu Thr Val Cys
            35                  40                  45

Leu Ser Asn Leu Phe Lys Ser Pro Met Tyr Phe Phe Leu Ser Phe Leu
50                  55                  60

Ser Phe Val Asp Ile Cys Tyr Ser Ser Val Thr Ala Pro Lys Met Ile
65                  70                  75                  80

Val Asp Leu Leu Ala Lys Asp Lys Thr Ile Ser Tyr Val Gly Cys Met
                85                  90                  95

Leu Gln Leu Phe Gly Val His Phe Phe Gly Cys Thr Glu Ile Phe Ile
            100                 105                 110

Leu Thr Val Met Ala Tyr Asp Arg Tyr Val Ala Ile Cys Lys Pro Leu
            115                 120                 125

His Tyr Met Thr Ile Met Asn Arg Glu Thr Cys Asn Lys Met Leu Leu
            130                 135                 140

Gly Thr Trp Val Gly Gly Phe Leu His Ser Ile Ile Gln Val Ala Leu
145                 150                 155                 160

Val Val Gln Leu Pro Phe Cys Gly Pro Asn Glu Ile Asp His Tyr Phe
            165                 170                 175

Cys Asp Val His Pro Val Leu Lys Leu Ala Cys Thr Glu Thr Tyr Ile
            180                 185                 190

Val Gly Val Val Thr Ala Asn Ser Gly Thr Ile Ala Leu Gly Ser
            195                 200                 205

Phe Val Ile Leu Leu Ile Ser Tyr Ser Ile Ile Leu Val Ser Leu Arg
210                 215                 220

Lys Gln Ser Ala Glu Gly Arg Arg Lys Ala Leu Ser Thr Cys Gly Ser
225                 230                 235                 240

His Ile Ala Met Val Val Ile Phe Phe Gly Pro Cys Thr Phe Met Tyr
            245                 250                 255

Met Arg Pro Asp Thr Thr Phe Ser Glu Asp Lys Met Val Ala Val Phe
            260                 265                 270

Tyr Thr Ile Ile Thr Pro Met Leu Asn Pro Leu Ile Tyr Thr Leu Arg
            275                 280                 285

Asn Ala Glu Val Lys Asn Ala Met Lys Lys Leu Trp Gly Arg Asn Val
            290                 295                 300

Phe Leu Glu Ala Lys Gly Lys
305                 310

<210> SEQ ID NO 43
<211> LENGTH: 24
<212> TYPE: DNA
<213> ORGANISM: Artificial Sequence
<220> FEATURE:
<223> OTHER INFORMATION: FLAG tag

<400> SEQUENCE: 43
gattacaagg acgacgacga taag                                          24

<210> SEQ ID NO 44
<211> LENGTH: 8
<212> TYPE: PRT
<213> ORGANISM: Artificial Sequence
<220> FEATURE:
<223> OTHER INFORMATION: FLAG tag

<400> SEQUENCE: 44

Asp Tyr Lys Asp Asp Asp Lys
1               5

<210> SEQ ID NO 45
<211> LENGTH: 60
<212> TYPE: DNA
<213> ORGANISM: Artificial Sequence
<220> FEATURE:
<223> OTHER INFORMATION: Rho tag

<400> SEQUENCE: 45
atgaacggga ccgagggccc aaacttctac gtgcctttct ccaacaagac gggcgtggtg    60

<210> SEQ ID NO 46
<211> LENGTH: 20
<212> TYPE: PRT
<213> ORGANISM: Artificial Sequence
<220> FEATURE:
<223> OTHER INFORMATION: Rho tag

<400> SEQUENCE: 46

Met Asn Gly Thr Glu Gly Pro Asn Phe Tyr Val Pro Phe Ser Asn Lys
1               5                   10                  15

Thr Gly Val Val
            20

<210> SEQ ID NO 47
<211> LENGTH: 51
<212> TYPE: DNA
<213> ORGANISM: Artificial Sequence
<220> FEATURE:
<223> OTHER INFORMATION: Lucy tag

<400> SEQUENCE: 47
atgagacccc agatcctgct gctcctggcc ctgctgaccc taggcctggc t              51

<210> SEQ ID NO 48
<211> LENGTH: 17
<212> TYPE: PRT
<213> ORGANISM: Artificial Sequence
<220> FEATURE:
<223> OTHER INFORMATION: Lucy tag

<400> SEQUENCE: 48

Met Arg Pro Gln Ile Leu Leu Leu Ala Leu Leu Thr Leu Gly Leu
1               5                   10                  15

Ala

<210> SEQ ID NO 49
<211> LENGTH: 1376
<212> TYPE: DNA
<213> ORGANISM: Homo sapiens

<400> SEQUENCE: 49
atgggtctgt gctacagtct gcggccgctg cttttcgggg cccaggggga cgacccctgc    60
gcggcctcgg agccgccggt ggaggacgcg cagccccgcc cggccccggc cctggcccca   120
gtccgggcgg ccgcaaggga cacggcccgg accctgctcc ctcggggcgg cgaagggagc   180
ccggcatgcg ctcggcccaa agcagacaag ccgaaggaga gcggcagcg caccgagcag   240 cttagtgccg aggagcgcga ggcggccaag gagcgcgagg cggtcaagga ggcgaggaaa   300

-continued

```
gtgagccggg gcatcgaccg catgctgcgc gaccagaagc gcgacctgca gcagacgcac      360
cggctcctgc tgctcgggc tggtgagtct gggaaaagca ctatcgtcaa acagatgagg      420
atcctgcacg tcaatgggtt taatcccgag gaaaagaaac agaaaattct ggacatccgg      480
aaaaatgtta agatgctat cgtgacaatt gtttcagcaa tgagtactat aatacctcca      540
gttccgctgg ccaaccctga aaccaatttt cgatcagact acatcaagag catagcccct      600
atcactgact ttgaatattc ccaggaattc tttgaccatg tgaaaaaact ttgggacgat      660
gaaggcgtga aggcatgctt tgagagatcc aacgaatacc agctgattga ctgtgcacaa      720
tacttcctgg aaagaatcga cagcgtcagc ttggttgact acacacccac agaccaggac      780
ctcctcagat gcagagttct gacatctggg attttgaga cgattccaa gtggacaaag      840 taaacttcca catgtttgat gttggtggcc agagggatga gaggagaaaa tggatccagt      900
gctttaacga tgtcacagct atcatttacg tcgcagcctg cagtagctac aacatggtga      960
ttcgagaaga taacaacacc aacaggctga gagtccct ggatcttttt gaaagcatct     1020
ggaacaacag gtggttacgg accatttcta tcatcttgtt cttgaacaaa caagatatgc     1080
tggcagaaaa agtcttggca gggaaatcaa aaattgaaga ctatttccca gaatatgcaa     1140
attatactgt tcctgaagac gcaacaccag atgcaggaga agatcccaaa gttacaagag     1200
ccaagttctt tatccgggac ctgtttttga ggatcagcac ggccaccggt gacggcaaac     1260
attactgcta cccgcacttc acctgcgccg tggacacaga gaacatccgc agggtgttca     1320
acgactgccg cgacatcatc agcggatgc acctcaagca gtatgagctc ttgtga          1376
```

<210> SEQ ID NO 50
<211> LENGTH: 458
<212> TYPE: PRT
<213> ORGANISM: Homo sapiens

<400> SEQUENCE: 50

```
Met Gly Leu Cys Tyr Ser Leu Arg Pro Leu Phe Gly Gly Pro Gly
1               5                   10                  15

Asp Asp Pro Cys Ala Ala Ser Glu Pro Pro Val Glu Asp Ala Gln Pro
            20                  25                  30

Ala Pro Ala Pro Ala Leu Ala Pro Val Arg Ala Ala Arg Asp Thr
        35                  40                  45

Ala Arg Thr Leu Leu Pro Arg Gly Gly Glu Gly Ser Pro Ala Cys Ala
    50                  55                  60

Arg Pro Lys Ala Asp Lys Pro Lys Glu Lys Arg Gln Arg Thr Glu Gln
65                  70                  75                  80

Leu Ser Ala Glu Glu Arg Glu Ala Ala Lys Glu Arg Glu Ala Val Lys
                85                  90                  95

Glu Ala Arg Lys Val Ser Arg Gly Ile Asp Arg Met Leu Arg Asp Gln
            100                 105                 110

Lys Arg Asp Leu Gln Gln Thr His Arg Leu Leu Leu Leu Gly Ala Gly
        115                 120                 125

Glu Ser Gly Lys Ser Thr Ile Val Lys Gln Met Arg Ile Leu His Val
    130                 135                 140

Asn Gly Phe Asn Pro Glu Glu Lys Lys Gln Lys Ile Leu Asp Ile Arg
145                 150                 155                 160

Lys Asn Val Lys Asp Ala Ile Val Thr Ile Val Ser Ala Met Ser Thr
                165                 170                 175

Ile Ile Pro Pro Val Pro Leu Ala Asn Pro Glu Asn Gln Phe Arg Ser
            180                 185                 190
```

```
Asp Tyr Ile Lys Ser Ile Ala Pro Ile Thr Asp Phe Glu Tyr Ser Gln
        195                 200                 205

Glu Phe Phe Asp His Val Lys Lys Leu Trp Asp Glu Gly Val Lys
210                 215                 220

Ala Cys Phe Glu Arg Ser Asn Glu Tyr Gln Leu Ile Asp Cys Ala Gln
225                 230                 235                 240

Tyr Phe Leu Glu Arg Ile Asp Ser Val Ser Leu Val Asp Tyr Thr Pro
                245                 250                 255

Thr Asp Gln Asp Leu Leu Arg Cys Arg Val Leu Thr Ser Gly Ile Phe
                260                 265                 270

Glu Thr Arg Phe Gln Val Asp Lys Val Asn Phe His Met Phe Asp Val
                275                 280                 285

Gly Gly Gln Arg Asp Glu Arg Arg Lys Trp Ile Gln Cys Phe Asn Asp
290                 295                 300

Val Thr Ala Ile Ile Tyr Val Ala Ala Cys Ser Ser Tyr Asn Met Val
305                 310                 315                 320

Ile Arg Glu Asp Asn Asn Thr Asn Arg Leu Arg Glu Ser Leu Asp Leu
                325                 330                 335

Phe Glu Ser Ile Trp Asn Asn Arg Trp Leu Arg Thr Ile Ser Ile Ile
                340                 345                 350

Leu Phe Leu Asn Lys Gln Asp Met Leu Ala Glu Lys Val Leu Ala Gly
                355                 360                 365

Lys Ser Lys Ile Glu Asp Tyr Phe Pro Glu Tyr Ala Asn Tyr Thr Val
370                 375                 380

Pro Glu Asp Ala Thr Pro Asp Ala Gly Glu Asp Pro Lys Val Thr Arg
385                 390                 395                 400

Ala Lys Phe Phe Ile Arg Asp Leu Phe Leu Arg Ile Ser Thr Ala Thr
                405                 410                 415

Gly Asp Gly Lys His Tyr Cys Tyr Pro His Phe Thr Cys Ala Val Asp
                420                 425                 430

Thr Glu Asn Ile Arg Arg Val Phe Asn Asp Cys Arg Asp Ile Ile Gln
                435                 440                 445

Arg Met His Leu Lys Gln Tyr Glu Leu Leu
450                 455

<210> SEQ ID NO 51
<211> LENGTH: 1125
<212> TYPE: DNA
<213> ORGANISM: Homo sapiens

<400> SEQUENCE: 51
atggcccggt cgctgacctg gcgctgctgc ccctggtgcc tgacggagga tgagaaggcc      60
gccgcccggg tggaccagga gatcaacagg atcctcttgg agcagaagaa gcaggaccgc     120
ggggagctga agctgctgct tttgggccca ggcgagagcg gaagagcac cttcatcaag      180 cagatgcgga tcatccacgg cgccggctac tcggaggagg agcgcaaggg cttccggccc     240
ctggtctacc agaacatctt cgtgtccatg cgggccatga tcgaggccat ggagcggctg     300
cagattccat tcagcaggcc cgagagcaag caccacgcca gctggtcat gagccaggac     360 ccctataaag tgaccacgtt tgagaagcgc tacgctgcgg ccatgcagtg gctgtggagg     420
gatgccggca tccgggcctg ctatgagcgt cggcgggaat tccacctgct cgattcagcc     480
gtgtactacc tgtcccacct ggagcgcatc accgaggagg gctacgtccc cacagctcag     540
gacgtgctcc gcagccgcat gcccaccact ggcatcaacg agtactgctt ctccgtgcag     600
```

```
aaaaccaacc tgcggatcgt ggacgtcggg ggccagaagt cagagcgtaa gaaatggatc    660
cattgtttcg agaacgtgat cgccctcatc tacctggcct cactgagtga atacgaccag    720
tgcctggagg agaacaacca ggagaaccgc atgaaggaga gcctcgcatt gtttgggact    780
atcctggaac taccctggtt caaaagcaca tccgtcatcc tctttctcaa caaaaccgac    840
atcctggagg agaaaatccc cacctcccac ctggctacct atttccccag tttccagggc    900
cctaagcagg atgctgaggc agccaagagg ttcatcctgg acatgtacac gaggatgtac    960
accgggtgcg tggacggccc cgagggcagc aagaagggcg cacgatcccg acgcctcttc    1020
agccactaca catgtgccac agacacacag aacatccgca aggtcttcaa ggacgtgcgg    1080
gactcggtgc tcgcccgcta cctggacgag atcaacctgc tgtga                   1125
```

<210> SEQ ID NO 52
<211> LENGTH: 374
<212> TYPE: PRT
<213> ORGANISM: Homo sapiens

<400> SEQUENCE: 52

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr

```
                275                 280                 285
Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
                325                 330                 335

Arg Arg Leu Phe Ser His Tyr Thr Cys Ala Thr Asp Thr Gln Asn Ile
            340                 345                 350

Arg Lys Val Phe Lys Asp Val Arg Asp Ser Val Leu Ala Arg Tyr Leu
        355                 360                 365

Asp Glu Ile Asn Leu Leu
    370

<210> SEQ ID NO 53
<211> LENGTH: 10
<212> TYPE: PRT
<213> ORGANISM: Artificial Sequence
<220> FEATURE:
<223> OTHER INFORMATION: Protein motif

<400> SEQUENCE: 53

Met Ala Tyr Asp Arg Tyr Val Ala Ile Cys
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Protein motif

<400> SEQUENCE: 54

Phe Ser Thr Cys Ser Ser His
1               5

<210> SEQ ID NO 55
<211> LENGTH: 8
<212> TYPE: PRT
<213> ORGANISM: Artificial Sequence
<220> FEATURE:
<223> OTHER INFORMATION: Protein motif

<400> SEQUENCE: 55

Pro Met Leu Asn Pro Phe Ile Tyr
1               5
```